US011008342B2

(12) United States Patent
Fisher et al.

(10) Patent No.: US 11,008,342 B2
(45) Date of Patent: May 18, 2021

(54) CRYSTALLINE POLYMORPHS OF A MUSCARINIC ACETYLCHOLINE RECEPTOR AGONIST

(71) Applicant: NSC Therapeutics GmbH, St. Radegund (AT)

(72) Inventors: Abraham Fisher, Holon (IL); Nira Bar-Ner, Rishon LeZion (IL); Manfred Windisch, St. Radegund (AT)

(73) Assignee: NSC Therapeutics GmbH, St. Radegund (AT)

( * ) Notice: Subject to any disclaimer, the term of this patent is extended or adjusted under 35 U.S.C. 154(b) by 0 days.

(21) Appl. No.: 16/338,930

(22) PCT Filed: Oct. 5, 2017

(86) PCT No.: PCT/EP2017/075373
§ 371 (c)(1),
(2) Date: Apr. 2, 2019

(87) PCT Pub. No.: WO2018/065529
PCT Pub. Date: Apr. 12, 2018

(65) Prior Publication Data
US 2020/0040007 A1 Feb. 6, 2020

(30) Foreign Application Priority Data
Oct. 5, 2016 (EP) .................... 16192494

(51) Int. Cl.
*C07D 513/10* (2006.01)
*A61P 27/02* (2006.01)
(52) U.S. Cl.
CPC ............ *C07D 513/10* (2013.01); *A61P 27/02* (2018.01); *C07B 2200/13* (2013.01)

(58) Field of Classification Search
None
See application file for complete search history.

(56) References Cited

FOREIGN PATENT DOCUMENTS

| WO | 199503303 A2 | 2/1995 |
|---|---|---|
| WO | 2003092580 A2 | 11/2003 |

OTHER PUBLICATIONS

International Search Report and Written Opinion dated Nov. 24, 2017 in International (PCT) Application No. PCT/EP2017/075373 (13 pages).
Byrn et al., "Pharmaceutical solids: A strategic approach to regulatory considerations," Pharmaceutical Research, vol. 12, No. 7, Jul. 1, 1995, pp. 945-954.
Brittain, "Spectral Methods for the characterization of polymorphs and solvates," Journal of Pharmaceutical Sciences, vol. 86, No. 4, Apr. 1, 1997.
Seymour et al., Decision T 0777/08 of the Boards of Appeal of the European Patent Office, Jul. 8, 2011, pp. 1-3 and 1-14.

*Primary Examiner* — Noble E Jarrell
(74) *Attorney, Agent, or Firm* — Clark & Elbing LLP; Susan M. Michaud

(57) ABSTRACT

Provided are novel crystalline forms of a spiro-compound which acts as a muscarinic acetylcholine receptor agonist. In particular, isolated crystalline polymorphs of (S)-2-ethyl-8-methyl-1-thia-4,8-diazaspiro[4.5]decane-3-one are described which have favorable properties in pharmaceutical manufacture. Also provided are methods to prepare said crystalline polymorphs, and to convert them into each other as well as methods for preparing medicaments containing the same which are suitable for use in the treatment of diseases and disorders that respond to modulation of the muscarinic acetylcholine receptor.

24 Claims, 17 Drawing Sheets

CRYSTALLINE POLYMORPHS OF A MUSCARINIC ACETYLCHOLINE RECEPTOR AGONIST

RELATED APPLICATIONS

This application is the National Stage application under 35 U.S.C. 371 of PCT International Application No. PCT/EP2017/075373, filed on Oct. 5, 2017, which claims priority from European Patent Application No. EP 16192494.9, filed on Oct. 5, 2016, the contents of which are hereby incorporated by reference in their entirety.

FIELD OF THE INVENTION

The present invention relates to crystalline polymorphs of a spiro-compound, pharmaceutical compositions containing the polymorphs, and their use in the treatment of acetylcholine-mediated diseases.

BACKGROUND OF THE INVENTION

The degeneration of cholinergic neurons and cholinergic hypofunction are pathologies associated with Alzheimer's disease (AD). Muscarinic acetylcholine receptors (mAChRs) mediate acetylcholine-induced neurotransmission and five mAChR subtypes (M1-M5) have been identified. Among them, M1 receptor is widely expressed in the central nervous system (CNS) and has been implicated in many physiological and pathological brain functions. In addition, M1 receptor is postulated to be an important therapeutic target for AD and several other neurodegenerative diseases; see for review, e.g., Jiang et al., Neurosci. Bull. 30 (2014), 295-307. Xanomeline, an orthosteric muscarinic agonist with modest selectivity for M1 and M4, was one of the first compounds that displayed improvements in behavioral disturbances in AD patients and efficacy in schizophrenics. Meanwhile, further compounds that display improved selectivity for M1 receptor are tried to be developed; see for review, e.g., Melancon et al., Drug Discovery Today 18 (2013), 1185-1199. However, in all clinical studies xanomeline and other related muscarinic agonists have displayed an unacceptable safety margin with respect to cholinergic adverse events, including nausea, gastrointestinal pain, diarrhea, diaphoresis (excessive sweating), hypersalivation (excessive salivation), syncope and bradycardia.

Thus, there remains a need for compounds that are capable of selectively modulating the activity of the M1 receptor, have no adverse effects seen from stimulation of other muscarinic receptors, which are safe and tolerable in humans and amenable to drug manufacturing processes which comply with current Good Manufacturing Practice (cGMP) regulations.

This problem is solved by the present invention in accordance with the embodiments as characterized in the claims and described further below.

SUMMARY OF THE PRESENT INVENTION

The present invention generally relates to novel crystalline forms of (S)-2-ethyl-8-methyl-1-thia-4,8-diazaspiro[4.5]decan-3-one (Compound A)

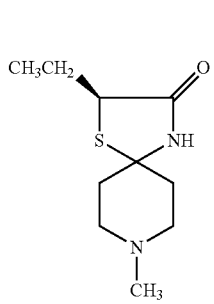

Compound A wherein said polymorph is selected from the group consisting of:
Form I which is a monohydrate of Compound A that exhibits a powder x-ray diffraction (XRPD) pattern substantially the same as the pattern shown in FIG. 1; differential scanning calorimetry (DSC) curves substantially the same as the curves shown in FIGS. 3A and 3B, respectively; a solid-state CP/MAS $^{13}$C NMR spectra substantially the same as the spectra shown in FIG. 9B; and an ATR FT-IR spectra substantially the same as the spectra shown in FIG. 10A;
Form II which is an anhydrous form of Compound A that exhibits an XRPD pattern substantially the same as the pattern shown in FIGS. 6A and 6B, respectively; differential scanning calorimetry (DSC) curves substantially the same as the curves shown in FIGS. 7A and 7B, respectively; a thermogravimetric analysis (TGA) curve substantially the same as the curve shown in FIGS. 8A and 8B, respectively; a solid-state CP/MAS $^{13}$C NMR spectra substantially the same as the spectra shown in FIG. 9A; and an ATR FT-IR spectra substantially the same as the spectra shown in FIGS. 10A and 10B, respectively; and
Form III which is a monohydrate of Compound A that exhibits an XRPD pattern substantially the same as the pattern shown in FIG. 2; DSC curves substantially the same as the curves shown in FIGS. 4A and 4B; a TGA curve substantially the same as the curve shown in FIG. 5; and a solid-state CP/MAS $^{13}$C NMR spectra substantially the same as the spectra shown in FIG. 9C.

The crystalline polymorph forms are useful in a variety of pharmaceutical applications, e.g. for stimulating the M1 muscarinic receptor. The present invention is illustrated in FIGS. 1 to 16 and relates to individual aspects, in particular illustrated in the Examples, which represent the essential characteristics of the crystalline polymorph forms of the subject Compound A of the present invention.

Compound A [(S)-2-ethyl-8-methyl-1-thia-4,8-diazaspiro[4.5]decan-3-one], is known to be a selective M1 muscarinic receptor agonist and has been described in U.S. Pat. Nos. 7,439,251 and 7,049,321 and in the corresponding international application WO03/092580 as "AF267B" with the following chemical structure:

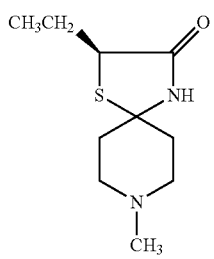

AF267B has been shown to increase αAPPs, decrease Aβ levels and tau hyperphosphorylation, and block Aβ-induced neurotoxicity in vitro via M1 receptor mediated modulation of kinases (e.g. PKC, MAPK and GSK3β); see for review, e.g., Fisher, Curr. Alzheimer Res. 4 (2007), 577-580 and Fisher, J. Neurochem. 120 (2012), 22-33. AF267B was found to improve spatial memory in 3×Tg-AD mice and was associated with reduced Aβ and tau pathologies in the hippocampus and cortex [Caccamo et al., Neuron. 49 (2006), 671-682]. Previously, Compound A (AF267B) formulated as a drug coined NGX-267 had been in phase II clinical trials for the treatment of Xerostomia and also in phase I clinical trials for the treatment of Alzheimer's disease and cognitive deficits in schizophrenia. In this context, the actual process of manufacture of AF267B/NGX-267 used in the clinical trials had not been disclosed but seemed to be different from the lab scale process described in the Examples of international application WO03/092580. However, despite encouraging results in the clinical trials in 2009 all clinical researches on this drug candidate were discontinued and had not been resumed.

Experiments performed in accordance with the present invention now surprisingly revealed that three distinct crystalline polymorphs of Compound A were found to exist, two of a monohydrate of Compound A herein referred to as Form I and Form III, and one anhydrous Compound A herein referred to as Form II. The three crystalline forms can be referred to as polymorphs. Each of the three polymorphs are not salt form. The anhydrous Form II and monohydrate Form III of Compound A were found to have substantially similar activity as described for NGX-267 ("AF267B"). Since the intended use of this compound is as a therapeutically active drug, the most stable pharmaceutically acceptable forms of the monohydrate of Compound A will be of great interest.

Hence, provided are novel crystal forms, in particular anhydrous Form II and monohydrate Form III of Compound A [(S)-2-ethyl-8-methyl-1-thia-4,8-diazaspiro[4.5]decane-3-one], which have favorable properties in pharmaceutical manufacture. Also provided are methods to prepare said novel forms, and to convert Form II into crystalline Form I or Form III, and Form I or Form III into Form II as well as methods for preparing medicaments containing said novel crystalline Forms which are suitable for use in the treatment of diseases and disorders that respond to modulation of M1 muscarinic receptor.

In one embodiment, the invention encompasses crystalline polymorph forms of Compound A that exhibit a certain powder diffraction pattern. In one embodiment, the crystalline polymorph forms are substantially free of solvates. In a preferred embodiment, these crystalline polymorph forms are substantially free of water, i.e., they are substantially anhydrous. In another embodiment the crystalline polymorph forms contain solvates. In a preferred embodiment, the crystalline polymorph forms contain fixed amounts of water.

In one embodiment, the invention encompasses methods to produce crystalline polymorph forms of Compound A that do not contain solvates; in a preferred embodiment, the crystalline polymorph forms are free of water (anhydrous).

In one embodiment, the present invention provides a crystalline polymorph form (Form II) of Compound A free of solvent and free of water, characterized by the following single crystal X-ray data: P2(1) a=8.1416(13), (α=90°), b=7.9811(12) (β=90.761(2)°, c=17.878(3), (γ=90°), Å, T=173(1)K. In one embodiment of the invention, the crystalline form is further characterized by the following data: Volume=1161.6 (3) Å 3, Z=4, F(000)=464, Calculated density, Dc=1.226 Mg/m$^3$, Absorption coefficient, μ=0.251 mm$^{-1}$.

In another embodiment, the method of the present invention produces crystalline polymorph forms of Compound A that contain solvates; more preferably such crystalline polymorph forms contain water. Even more preferably, the crystalline polymorph forms are monohydrates of Compound A.

In yet another embodiment, the present invention encompasses methods that convert different crystalline polymorphs of the present invention into each other; more preferably the method converts anhydrous and monohydrate crystalline polymorphs of the present invention into each other.

More specifically, as mentioned above, the present invention provides three crystalline polymorph forms of Compound A: one novel crystalline polymorph form of anhydrous Compound A, which for purposes of convenience will be referred to herein as Form II; and two crystalline polymorph forms of Compound A which contain one molecule of water for each molecule of Compound A (Form I and Form III).

In addition, the present invention encompasses various methods of preparing crystalline Forms I, II, and III of Compound A.

In yet another set of embodiments the present invention encompasses methods and compositions for preparing and administering pharmaceutical compositions that treat in a mammal diseases or conditions which are responsive to stimulation of the M1 muscarinic receptor; the methods comprising administering to a subject in need thereof an amount of a compound or a mixture of compounds comprising crystalline polymorph forms of Compound A (and/or pharmaceutically acceptable salts thereof) and a pharmaceutically acceptable carrier, diluent or excipient, efficacious to stimulate the M1 muscarinic receptor. In a preferred embodiment the crystalline polymorph forms are substantially free of water. In a more preferred embodiment the crystalline form is Form II of Compound A. In another preferred embodiment the crystalline polymorph forms contain one molecule of water for each molecule of Compound A and is Form III.

Still another embodiment encompasses pharmaceutical compositions comprising crystalline polymorph forms of Compound A as disclosed herein, e.g. crystalline polymorph forms that exhibit a X-ray powder diffraction pattern comprising at least one peak at a diffraction angle 2θ selected from the group consisting of 9.9°, 10.8° and 11.8°±0.2, and a pharmaceutically acceptable carrier, diluent or excipient therefor.

In one embodiment of the present invention, the pharmaceutical compositions contemplated herein further comprise additional forms of Compound A in a crystalline, solvate or amorphous form. In a particular embodiment, the additional form of Compound A is a monohydrate form. In another particular embodiment, the pharmaceutical compositions comprise at least 70% by weight of said crystalline polymorph form based on the total weight of Compound A in the composition, preferably 80%, 90%, 95% or 99% by weight of said crystalline polymorph form.

The embodiments of the present invention are characterized in the items below and will be further described in detail by way of the accompanying Figures and Examples.

DEFINITIONS

Figure 1A:
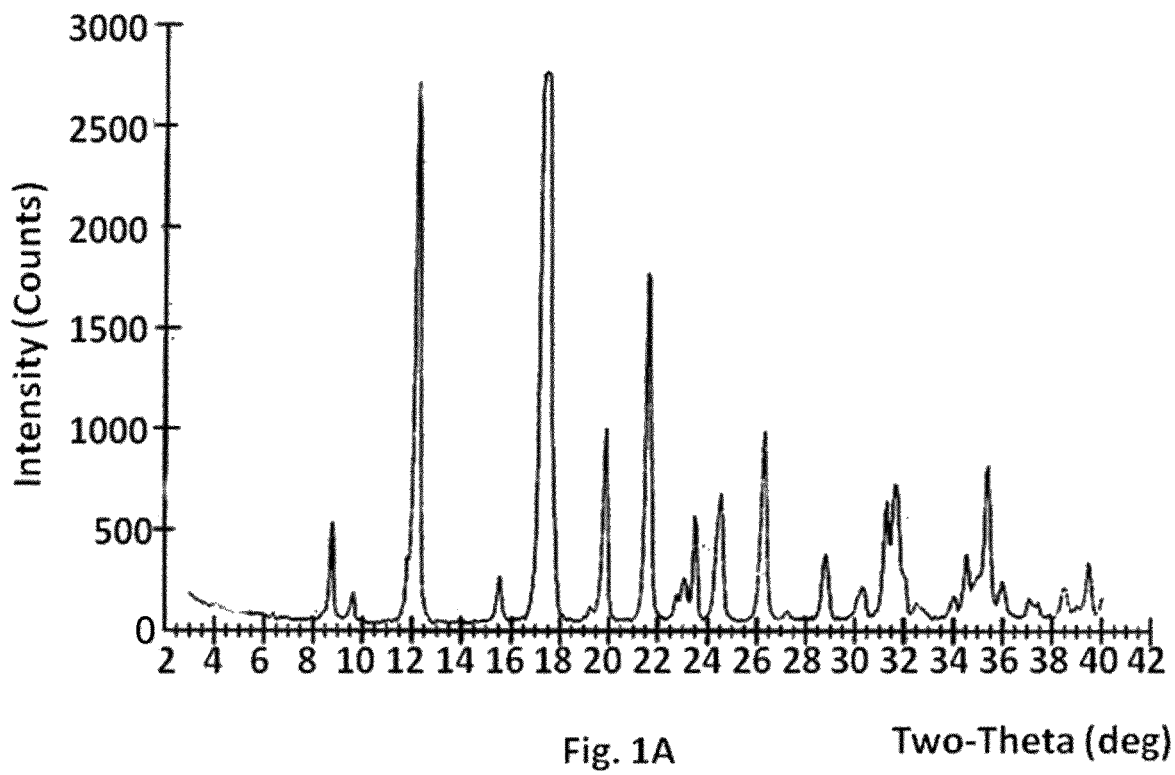
FIG. 1 shows X-ray powder diffraction patterns for Compound A crystalline Form I crystallized from ethyl acetate (A); and slow evaporation from water (B).

Throughout the present description and claims, terms which are defined as they are introduced retain those definitions throughout the description and claims. In addition, the following definitions apply throughout the present description and claims.

The terms "Crystalline form" and "Polymorph" refer to a particular chemical compound in a particular crystalline state, irrespective of whether that chemical compound is solvated or not. Thus, for example, a chemical compound which is shown to crystallize in two different non-solvated forms and one solvated form will be said to crystallize in three different crystalline polymorph forms or polymorphs. Furthermore, "Polymorph" means a crystalline form of a substance that is distinct from another crystalline form but that shares the same chemical formula.

Regarding "Polymorph Purity", preferably, the crystalline polymorphs Forms I-III of Compound A are substantially free of chemical impurities (e.g., by-products generated during the preparation of the polymorphs) and of other polymorphic crystalline forms. "Substantially free" of chemical impurities for the purposes of this invention means less than or equal to about 5% w/w of chemical impurities, preferably, less than or equal to about 3% w/w of chemical impurities, more preferably, less than or equal to about 2% w/w of chemical impurities, and even more preferably, less than or equal to about 1% w/w of chemical impurities. The term "purified" or "in purified form" for a polymorph refers to the physical state of said polymorph after being obtained from a purification process or processes described herein or well known to the skilled artisan, in sufficient purity to be characterizable by standard analytical techniques described herein or well known to the skilled artisan.

Purified forms of the crystalline polymorph Forms I-III of the monohydrate of Compound A are substantially free of chemical impurities.

The term "treating or preventing" when used in connection with the disorders and conditions listed herein means amelioration, prevention or relief from the symptoms and/or effects associated with these disorders or conditions. The term "preventing" as used herein refers to administering a medicament prophylactically. The person of ordinary skill in the medical art recognizes that the term "prevent" is not an absolute term. In the medical art it is understood to refer to the prophylactic administration of a drug to substantially diminish the likelihood or seriousness of a condition, and this is the sense intended in the claims. "Patient" includes both human and other animals. "Mammal" includes humans and other mammalian animals.

As used herein, "pharmaceutically acceptable" refers to materials and compositions that are physiologically tolerable and do not typically produce an allergic or similar untoward reaction, such as gastric upset, dizziness and the like, when administered to a human. Typically, as used herein, the term "pharmaceutically acceptable" means approved by a regulatory agency of the Federal or a state government or listed in the U.S. Pharmacopeia or other generally recognized pharmacopeia for use in animals, and more particularly in humans.

The phrase "pharmaceutically acceptable salt(s)," as used herein includes, but is not limited to, salts of acidic or basic groups that may be present in compounds used in the present compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions including, but not limited to, sulfuric, citric, maleic, acetic, oxalic, hydrochloride, hydrobromide, hydroiodide, nitrate, sulfate, bisulfate, phosphate, acid phosphate, isonicotinate, acetate, lactate, salicylate, citrate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts. Compounds included in the present compositions that include an amino moiety may form pharmaceutically acceptable salts with various amino acids, in addition to the acids mentioned above.

As used herein, the term "pharmaceutically acceptable carriers" can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material. In powders, the carrier is a finely divided solid which is in a mixture with the finely divided active component. In tablets, the active component or components is mixed with the carrier having the necessary binding properties in suitable proportions and compacted in the shape and size desired. Liquid form preparations include solutions, suspensions, and emulsions, for example, water or water propylene glycol solutions. For parenteral injection liquid preparations can be formulated in solution in aqueous polyethylene glycol solution. Aqueous solutions suitable for oral use can be prepared by dissolving the active component in water and adding suitable colorants, flavors, stabilizing and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

As used herein, the term "binders" or "excipients" refers to agents used to impart cohesive qualities to the powdered material. Binders, or "granulators" as they are sometimes known, impart cohesiveness to the tablet formulation, which insures the tablet remaining intact after compression, as well as improving the free-flowing qualities by the formulation of granules of desired hardness and size. Materials commonly used as binders include starch; gelatin; sugars, such as sucrose, glucose, dextrose, molasses, and lactose; natural and synthetic gums, such as acacia, sodium alginate, extract of Irish moss, panwar gum, ghatti gum, mucilage of isapol husks, carboxymethylcellulose, methylcellulose, polyvinylpyrrolidone, Veegum, microcrystalline cellulose, microcrystalline dextrose, amylose, and larch arabinogalactan, and the like. "Excipient" means an essentially inert substance used as a diluent or to give form or consistency to a formulation In general, excipients may be defined as the constituents of the pharmaceutical form that is taken by or administered to the patient, other than the active substance; see, e.g., Annex of Directive 2001/83/EC. Certain excipients can also serve as disintegrants, i.e., they assist the dispersion of solid pharmaceutical compositions upon exposure to body fluids.

As used herein, "diluents" are inert substances added to increase the bulk of the formulation to make the tablet a practical size for compression. Commonly used diluents include calcium phosphate, calcium sulfate, lactose, kaolin, mannitol, sodium chloride, dry starch, powdered sugar, silica, and the like.

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus <10% of the particular term and "substantially" and "significantly" will mean plus or minus >10% of the particular term.

It will be appreciated that when using NMR data to describe a material, NMR peaks may be reported in terms of absolute chemical shift values with reference to a standard (e.g. tetramethylsilane), or alternatively the material may be described in terms of differences between the chemical shift values of peaks. Thus, for example, a material may be described as having an NMR spectrum with peaks at 170.0 and 130.0 ppm, or the material may be described as having an NMR spectrum with a ppm difference between the peak of the greatest chemical shift value and another peak of 40.0 ppm. The later method of reporting is useful in that it is unaffected by systemic errors that may arise in the reporting of the absolute chemical shift values of the material. It will also be appreciated that in utilizing NMR spectra to identify a material, peak shape may help identify the material. Thus, for example, although two crystalline polymorph forms of the same molecule may have an NMR peak at approximately the same chemical shift value, in the spectrum of one of the materials the peak may be much sharper or higher than in the spectrum of the other crystalline polymorph form, thus facilitating identification of one or the other crystalline polymorph form. The same is true, mutatis mutandis, for other analytical methods.

DETAILED DESCRIPTION OF THE INVENTION—EXAMPLES

The subject matter of the present invention and its various aspects and embodiments as characterized above will now be illustrated by way of reference to the following Figures and Examples. Unless indicated otherwise, the terms used are understood according to the definitions given herein.

Furthermore, the disclosure content of the foregoing description in the background of the invention as far as applicable forms part of the disclosure of the present invention. It is to be understood that this invention is not limited to the particular methodology, protocols, cell lines, excipients, carriers, and reagents described herein as such. It is also to be understood that the terminology used herein is for the purpose of describing particular embodiments only, and is not intended to limit the scope of the present invention, which will be limited only by the appended claims. The embodiments of the present invention are summarized in the following items [1] to [40]. Accordingly, in its broadest aspect, the present invention relates to

[1] A crystalline polymorph of Compound A of the formula

Figure 1B:
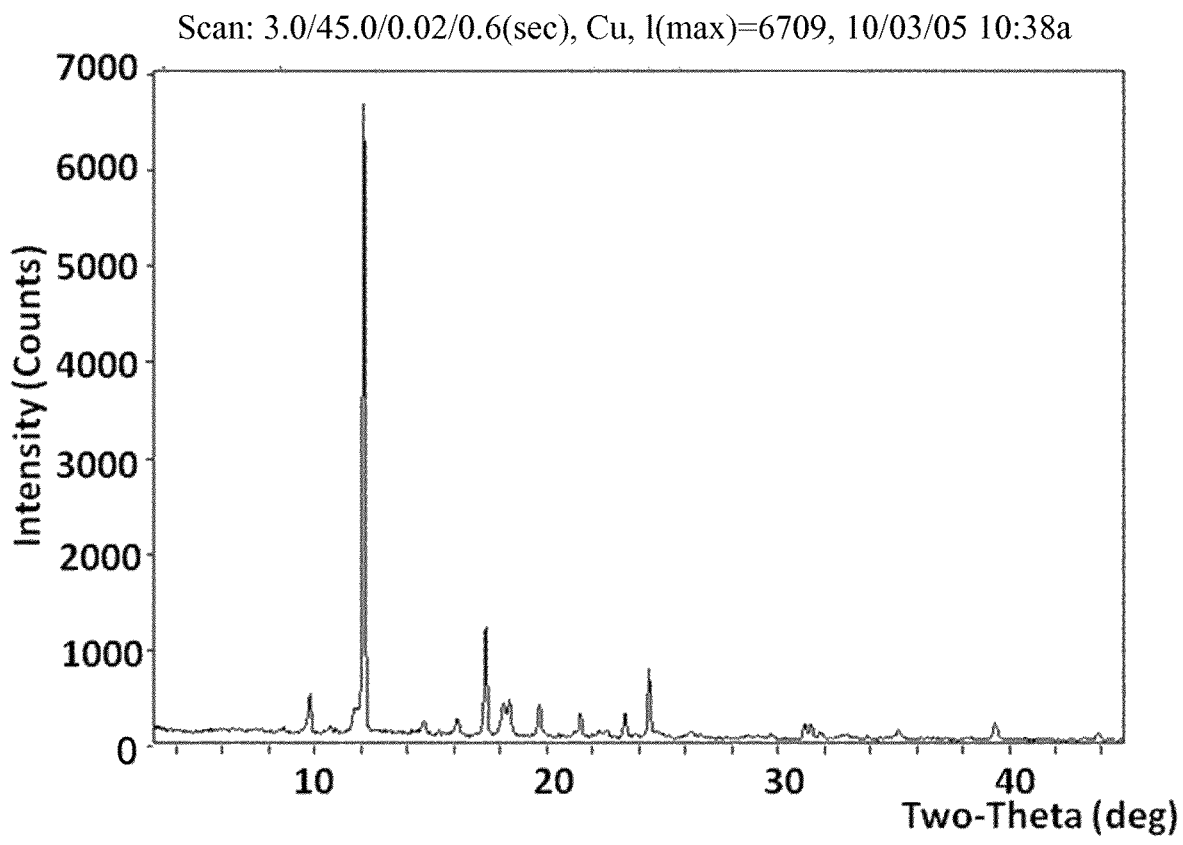
Figure 3A:
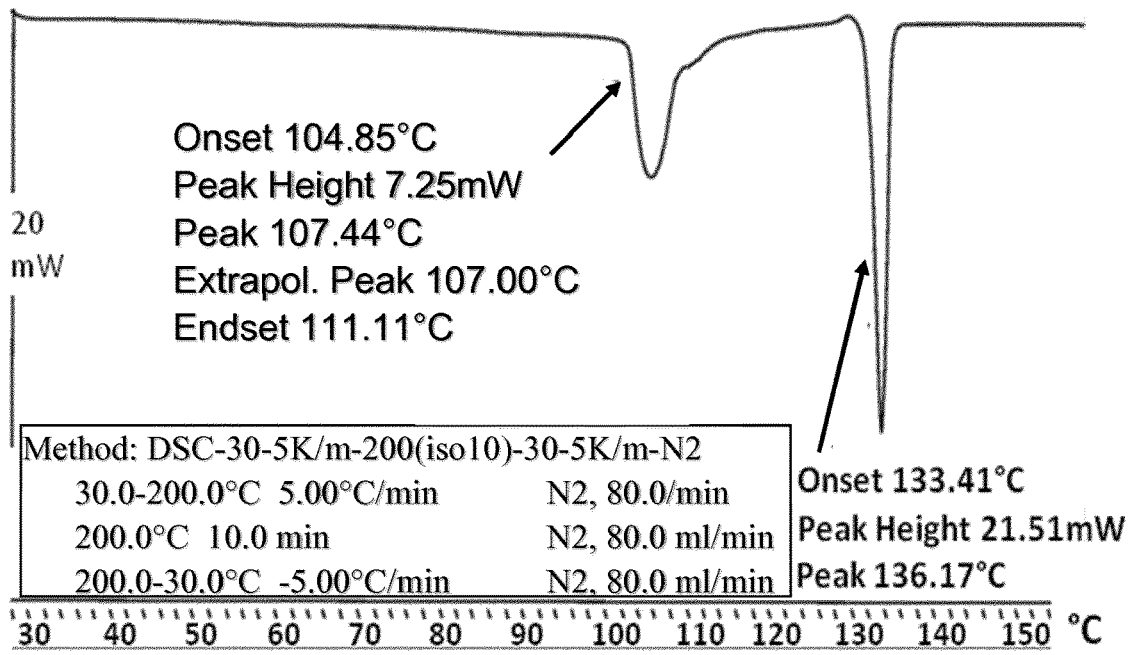
FIG. 3 presents differential scanning calorimetry (DSC) curves for a monohydrate crystalline polymorph form of Compound A (Form I): crystallized from ethyl acetate (A); and slow evaporation from water (B). The DSC indicates two endothermic peaks, one at about 107° C. and the other at about 136.17° C.
Figure 4A:
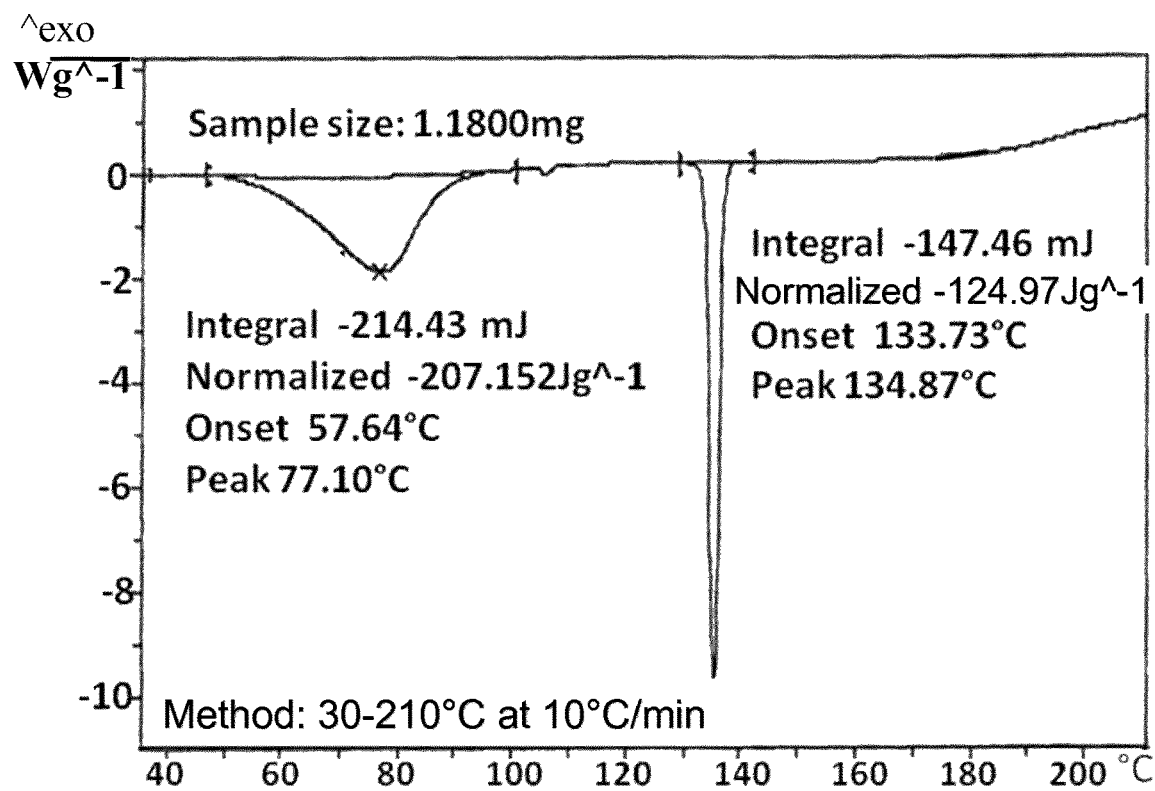
FIG. 4 presents differential scanning calorimetry (DSC) curves for a monohydrate crystalline polymorph form of Compound A (Form III); A) from a re-slurry in water. The DSC indicates two endothermic peaks, one at about 77.10° C. and the other at about 134.87° C.; B) the cGMP active pharmaceutical ingredient (API), prepared by crystallization from acetone and 1.3 equivalent of water. The DSC indicates two endothermic peaks, one at about 61.18° C. and the other at about 133.75° C.

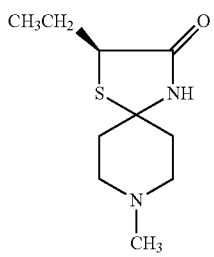

wherein said polymorph is selected from the group consisting of monohydrate Form I (i) having an X-ray powder diffraction pattern containing at least one of the following 2-theta values (±0.2) as measured using $CuK_\alpha$ radiation: 8.8, 12.3, 17.5, 19.9, 21.6 23.5, 24.5, 26.3, 28.8, 31.6, but lacks at least one of the following 2-theta values 17.3, 17.9, 21.9, 24.9, 29.3, 30.8 and 33.4; see also FIG. 1;

(ii) wherein the ZnSe ATR-FT-IR absorption spectrum of the crystalline form contains at least one absorption peak having a value selected from 1352, 1369 and 1387 $cm^{-1}$; and/or (iii) wherein the crystalline form exhibits an endothermic peak at 107.1° C. (onset at 104.85° C.) and 136.17° C. (onset at 133.41° C.) as measured by differential scanning calorimetry (DSC); and optionally; see also FIG. 3;

(iv) wherein the $^{13}C$ solid-state NMR of the crystalline form contains at least one resonance having one of the following chemical shift values as expressed in ppm relative to TMS: 67.09, 54.08, 46.59, 40.97, 30.15 and 13.27; and/or (v) wherein the $^{13}C$ solid-state NMR of the crystalline form contains a difference in chemical shift between the resonance having the largest chemical shift and another resonance of 107.3, 120.3, 127.8, 133.4, 144.2 or 161.1, anhydrous Form II (i) that exhibits a single crystal X-ray characterized by the following single crystal X-ray data: P2(1) a=8.1416 (13), (α=90°), b=7.9811(12) (β=90.761(2)°, c=17.878 (3), (γ=90°), Å, T=173(1)K; see also FIG. 11;

(ii) having an X-ray powder diffraction pattern containing at least one of the following 2-theta values (±0.2) as measured using $CuK_\alpha$ radiation: 9.9, 10.8, 11.8, 11.9, 14.8, 16.2, 18.2, 18.5, 19.8, 21.3, 22.4, 23.9, 29.2, 29.7 and 33.1; see also Table 1;

(iii) wherein the ZnSe ATR-FT-IR absorption spectrum of the crystalline form contains at least one absorption peak having a value selected from 1906, 1340, 1447, 2869, 2901, 2951, and 3006-3012 $cm^{-1}$;

(iv) wherein the $^{13}C$ solid-state NMR of the crystalline form contains at least one resonance having one of the following chemical shift values as expressed in ppm relative to TMS: 175.0; 65.3, 64.0; 45.8, 45.0; 49.3, 43.6, 39.5; 38.8; 28.9, 26.0; 15.4, 14.8; see also Table 5;

(v) wherein the $^{13}C$ solid-state NMR of the crystalline form contains a difference in chemical shift between the resonance having the largest chemical shift and another resonance of 109.7 or 111; 129.2 or 130.0; 122.7; 125.7; 131.4; 135.5; 136.2; 146.1 or 149.0; and 159.6 or 160.2; and/or (vi) wherein the crystalline form has an endothermic peak with an onset at 134.2° C. and peak at 135.4° C.±0.2° C. and substantially no endothermic peak between 106° C. and 110° C., lacking an endotherm peak in the range of about 50° C. to about 120° C., as measured by DSC; see also FIG. 7, or monohydrate Form III (i) (i) having an X-ray powder diffraction pattern containing at least one of the following 2-theta values (±0.2) as measured using $CuK_\alpha$ radiation: 12.3, 17.3, 17.5, 19.9, 21.6, 24.4, 26.3, and 35.4, and substantially free of peaks having 2-theta values in the range of 10.8-11.9; see also Table 2;

(ii) wherein the $^{13}C$ solid-state NMR of the crystalline form contains at least one resonance having one of the following chemical shift values as expressed in ppm relative to TMS: 67.56, 54.60, 47.97, 41.49, 30.70 and 13.77; see also Table 5;

(iii) wherein the $^{13}C$ solid-state NMR of the crystalline form contains a difference in chemical shift between the resonance having the largest chemical shift and another resonance of 107.3, 120.3, 127.0, 133.4, 144.2 or 161.1;

(iv) wherein the ZnSe ATR-FT-IR absorption spectrum of the crystalline form contains at least one absorption peak having a value selected from 1039, 1353, 1369, 1369, 1388, 2918, 2974 and 3088 $cm^{-1}$; and/or (v) wherein the crystalline form exhibits a very broad endothermic peak at 58-94° C. and an endothermic peak with an onset at 133.7° C. and a peak at 134.9° C. as measured by DSC; see also FIG. 4 and Table 3.

Compound A is disclosed in international application WO 03/092580 A2 as (2S)-2-ethyl-8-methyl-1-thia-4,8-diazaspiro[4.5]decan-3-one ("AF267B"), which reflect the following chemical structure:

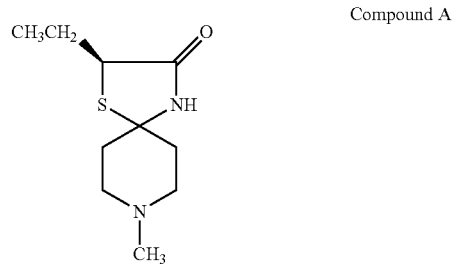

Compound A

That document also describes the chiral separation of R- and S-forms of Compound A by elution in an 85:15 mixture of acetonitrile/ethanol, followed by further addition of ethanol and evaporation to dryness to remove residual acetonitrile. However, the method disclosed in WO03/092580 and associated patents for preparing Compound A is uncontrolled with respect to a particular polymorphic crystalline form for which reason hitherto the polymorphic form(s) of Compound A were unknown. Furthermore, Compound A as prepared according to the method disclosed in WO03/092580 has not been proved to be suitable as a drug for pharmaceutical compositions. Therefore, in one embodiment the present invention does not relate to Compound A and its method of preparation disclosed in U.S. Pat. Nos. 7,439,251 and 7,049,321 and in the corresponding international application WO03/092580.

As mentioned, an essential part of the present invention is based on the unexpected observation that three distinct crystalline polymorphs of Compound A were found to exist, two of a monohydrate of Compound A herein referred to as Forms I and III, and one anhydrous Compound A herein referred to as Form II.

It is known that active pharmaceutical ingredients often occur in polymorphic forms which can be attributed to different crystalline forms, or to the lack of a crystalline state. As a result of differences in the order of the molecules in the crystal lattice, such polymorphic forms of a compound will differ in terms of melting point, X-ray diffraction patterns, infrared absorption fingerprints, and solid-state NMR spectra. Accordingly, these are solids that share the same molecular formula, yet differ in quantifiable features that are commonly used to characterize solids.

Polymorphism may also affect physical parameters that are important in pharmaceutical formulation and drug product manufacturing, such as storage stability, compressibility and density. For example, one form might be more likely to form desired or undesired solvates, or might be difficult to filter and wash free of impurities due to different particle shape and size distribution of one form relative to another. As a result of differences in the order of the molecules in the crystal lattice, polymorphism could also have a direct pharmaceutical effect by influencing dissolution rates in physiological fluids, which can change an orally active agent's absorption, pharmacokinetics and/or bioavailability. Ultimately, even the required dosage strength in the drug formulation necessary to obtain the ideal drug efficacy might be different for different polymorphs. If the drug can crystallize as two or more crystalline forms differing in bioavailability, the optimal dose will depend on the crystalline form present in the formulation. Polymorphism may also affect pharmaceutical parameters such as storage stability, compressibility and density which are important in formulation and product manufacturing. One form might be more likely to form desired or undesired solvates or might be difficult to filter and wash free of impurities due to different particle shape and size distribution of one form relative to another.

The present invention relates to crystalline forms, i.e. polymorphs of the compound (S)-2-ethyl-8-methyl-1-thia-4,8-diazaspiro[4.5]decan-3-one (Compound A), processes for preparing them and uses thereof. There are provided in accordance with embodiments of the present invention three crystalline forms of Compound A: one crystalline form of anhydrous Compound A, which for purposes of convenience will be referred to herein as Form II; and two distinct crystalline forms of Compound A which contain one molecule of water for each molecule of Compound A, which for purposes of convenience will be referred to herein as Forms I and III, respectively.

According to the present invention, crystalline forms of Compound A can be characterized in a variety of ways, e.g., Form II can readily be distinguished from Forms I and III, inter alia, by virtue of the presence or absence of water, using techniques such as those known in the current art, such as differential scanning calorimetry (DSC) and thermogravimetric analysis (TGA). Forms can also readily be distinguished by virtue of physical parameters or groups of physical parameters which are present in one form but not in the other form, including but not limited to physical parameters obtained through one or more of the following techniques: X-ray powder diffraction (XRPD), solid-state carbon-13 nuclear magnetic resonance using cross-polarization magic-angle spinning ($^{13}C$ CP-MAS NMR), Attenuated Total Reflection Fourier Transform Infrared spectroscopy (ATR-FT-IR), DSC and TGA.

Figure 9:
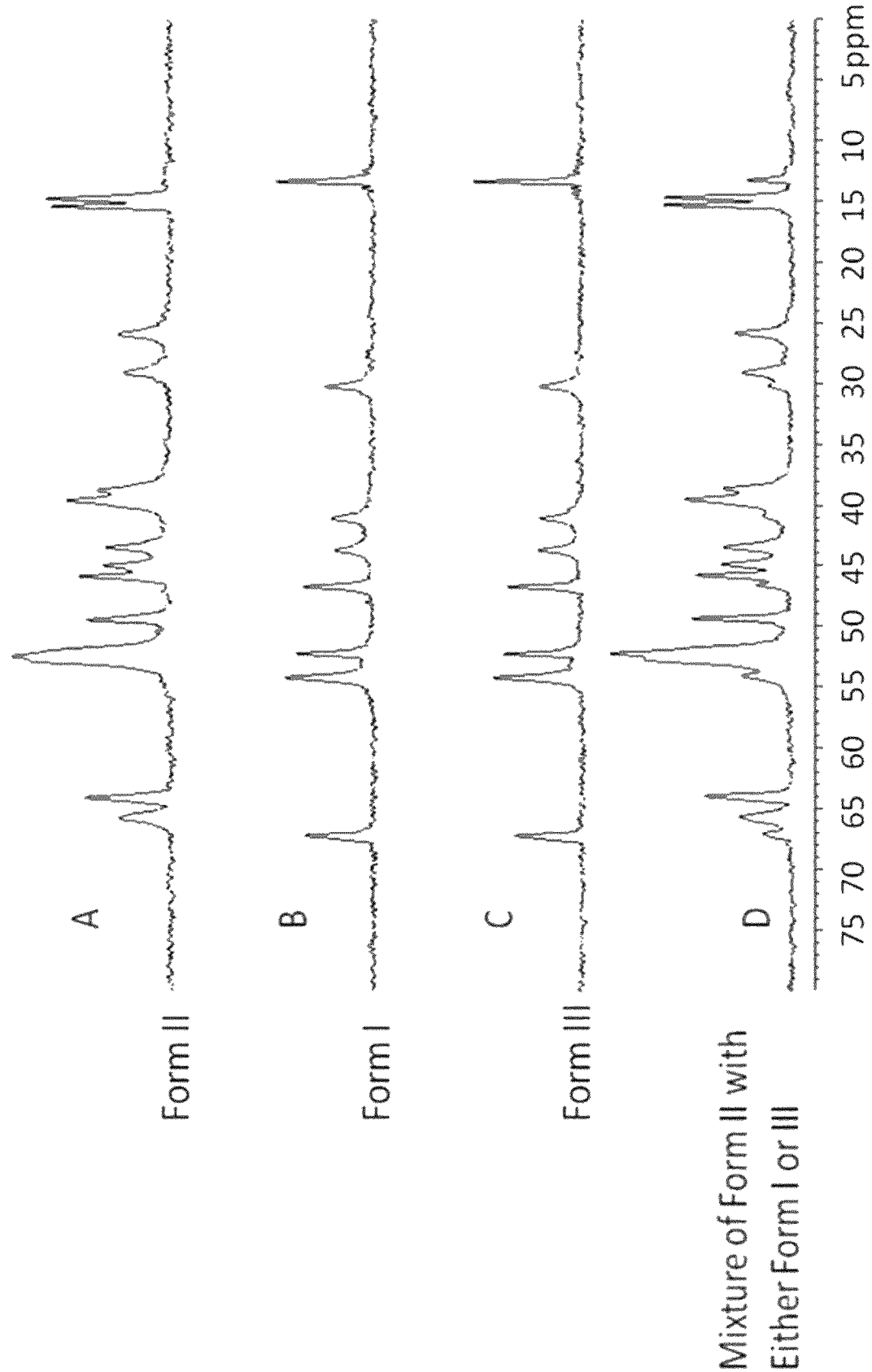
FIG. 9 is a representative solid-state CP/MAS $^{13}$C NMR spectra of crystalline Forms I and II of Compound A. Form III has an identical CP/MAS $^{13}$C NMR spectrum to Form I.
Figure 10A:
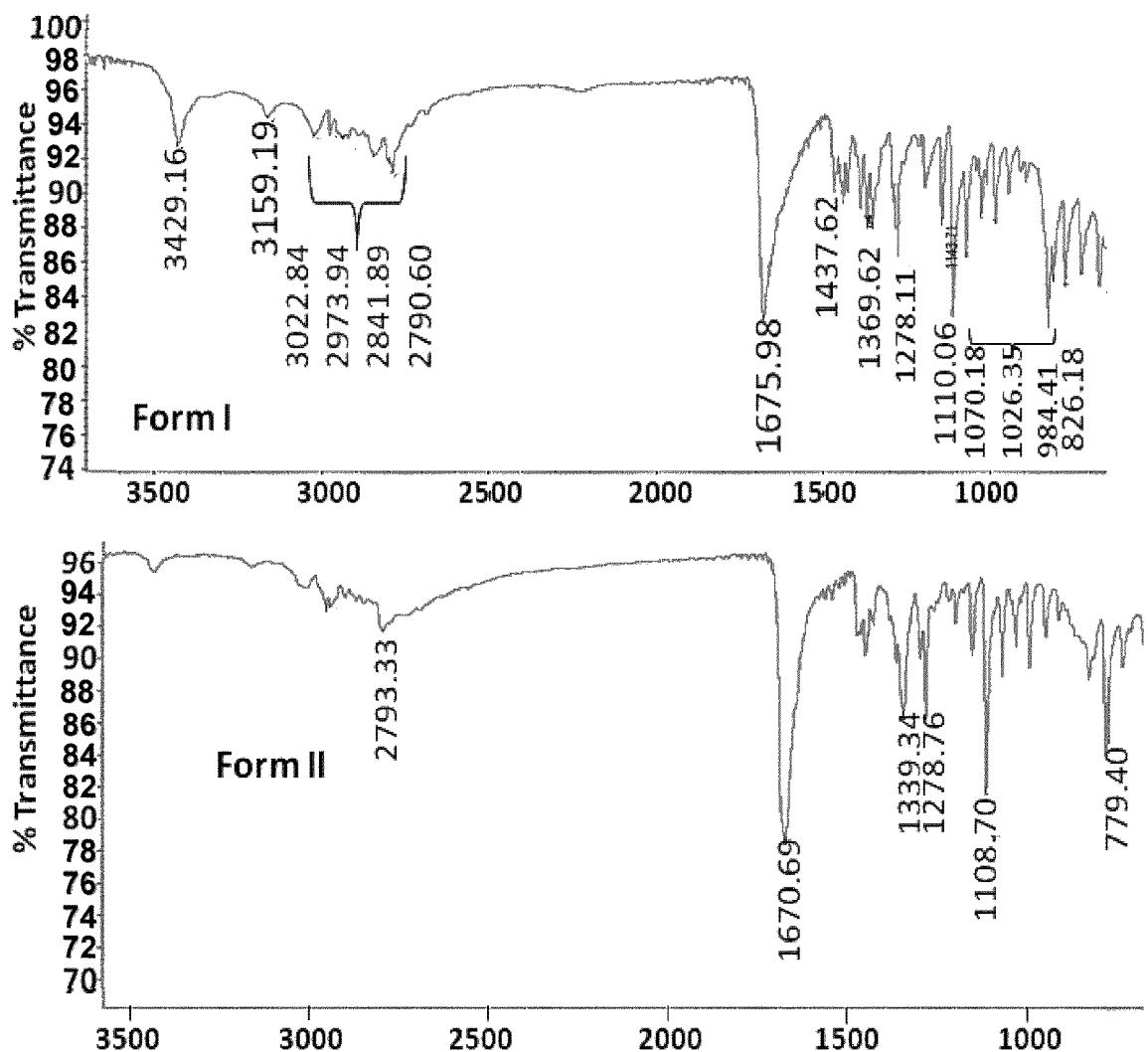
FIG. 10: A) Representative ATR FT-IR spectra of crystalline Form I (crystallized from ethyl acetate) and Form II (crystallized from dioxane) of Compound A. Recognizable difference of some absorption peaks was observed. 1340-1390 cm-1 region of the spectrum differentiates each form and can be used for the identification of the polymorphs. For crystal Form I—the relative shapes and intensities of absorption peaks at 1352, 1369 and 1387 cm$^{-1}$ can be used for diagnostic purposes. For crystal Form II—the relative shapes and intensities of absorption peaks at 1340-1362 cm$^{-1}$ can be used for diagnostic purposes. B) The cGMP API crystal Form II.
Figure 10B:
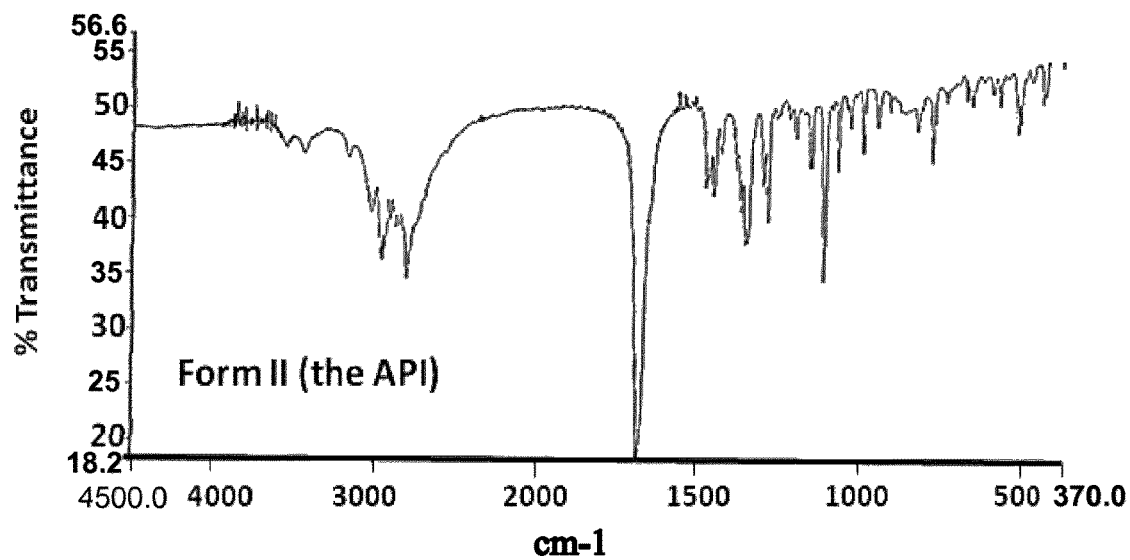

In one embodiment of the present invention, said polymorph is monohydrate Form I as characterized in item [1], supra, and illustrated in FIGS. 3, 9 and 10, respectively.

Form I is the monohydrate form that is preferentially obtained by directly crystallizing Compound A from water-miscible organic solvents that contain traces of water (ethanol, ethyl acetate, isopropanol, tert-butylmethylether, tetrahydrofuran) or water (Examples 1-6); The DSC indicates two endothermic peaks, one at about 107° C. and the other at about 136.17° C. (FIG. 3). Form I is crystalline polymorph as characterized by its XRPD peaks (FIG. 1). Form I can be transformed to the anhydrous Form II by heating the substance to 90° C. (Example 17). Form I can be transformed to the anhydrous Form II by heating the substance to 160° C. and leaving the molten mass to crystallize at room temperature (Example 18).

In a particular preferred embodiment, the present invention relates to crystalline polymorph form of Compound A which proved to be particular suitable to be manufactured according to cGMP, i.e. the present invention relates to

[2] The crystalline polymorph of [1], wherein the polymorph is the polymorph Form II.

Figure 11:
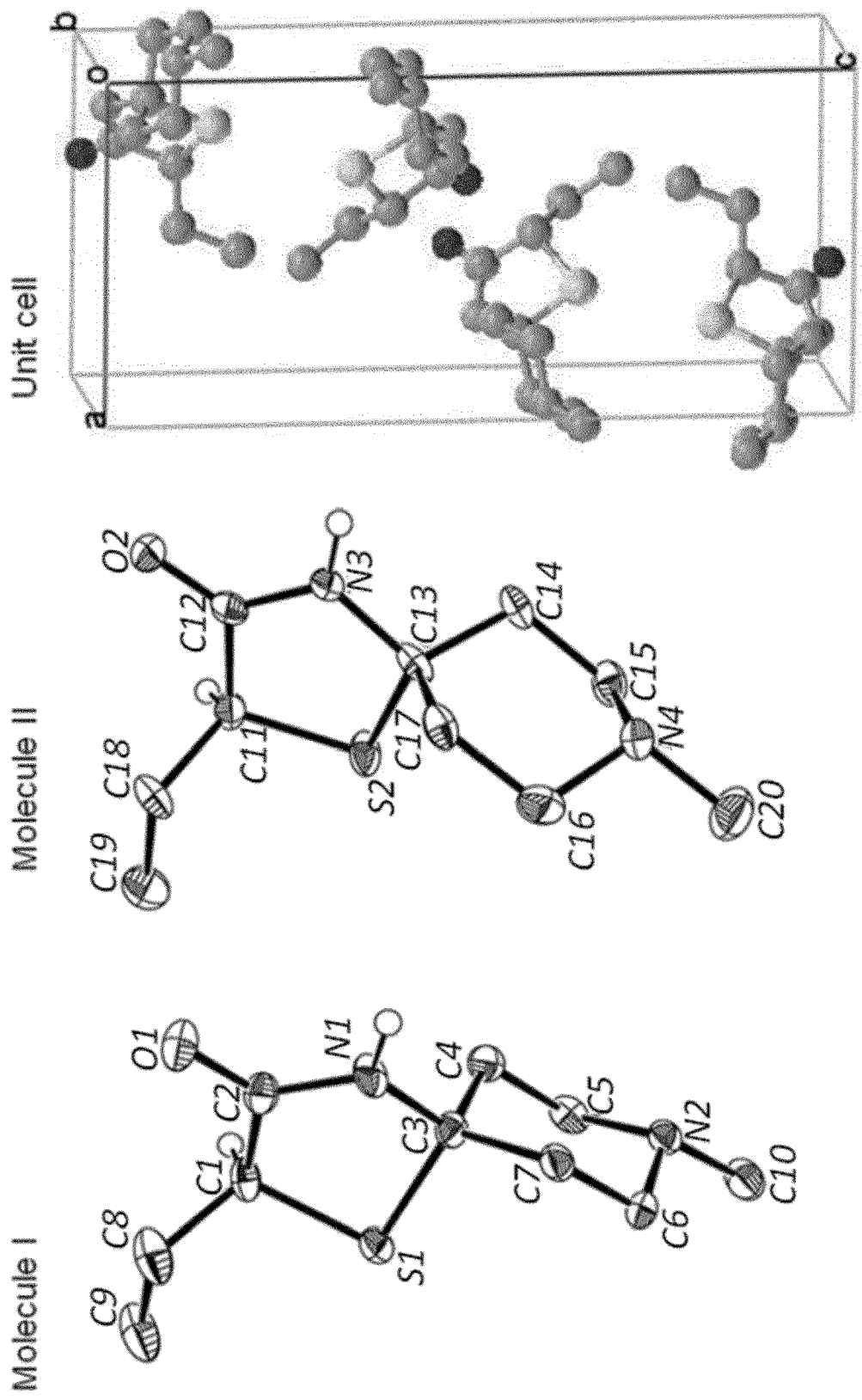
FIG. 11 presents the single crystal structure of Compound A anhydrous crystal (Form II, crystallized from acetonitrile) that shows two conformationally different molecules of the asymmetric unit and the arrangement in the unit cell.

There is provided in accordance with an embodiment of the invention a crystalline polymorph form of Compound A substantially free of water (hereinafter referred to as "Form II"), characterized by the following single crystal X-ray data: P2(1) a=8.1416(13), ($\alpha$=90°), b=7.9811(12) ($\beta$=90.761 (2)°, c=17.878(3), ($\gamma$=90°), Å, T=173(1)K. In an embodiment of the invention, the crystalline form is further characterized by the following data: Volume=1161.6 (3) Å 3, Z=4, F(000)=464, Calculated density, Dc=1.226 Mg/m$^3$, Absorption coefficient, $\mu$=0.251 mm$^{-1}$ (Example 26; FIG. 11).

Figure 6A:
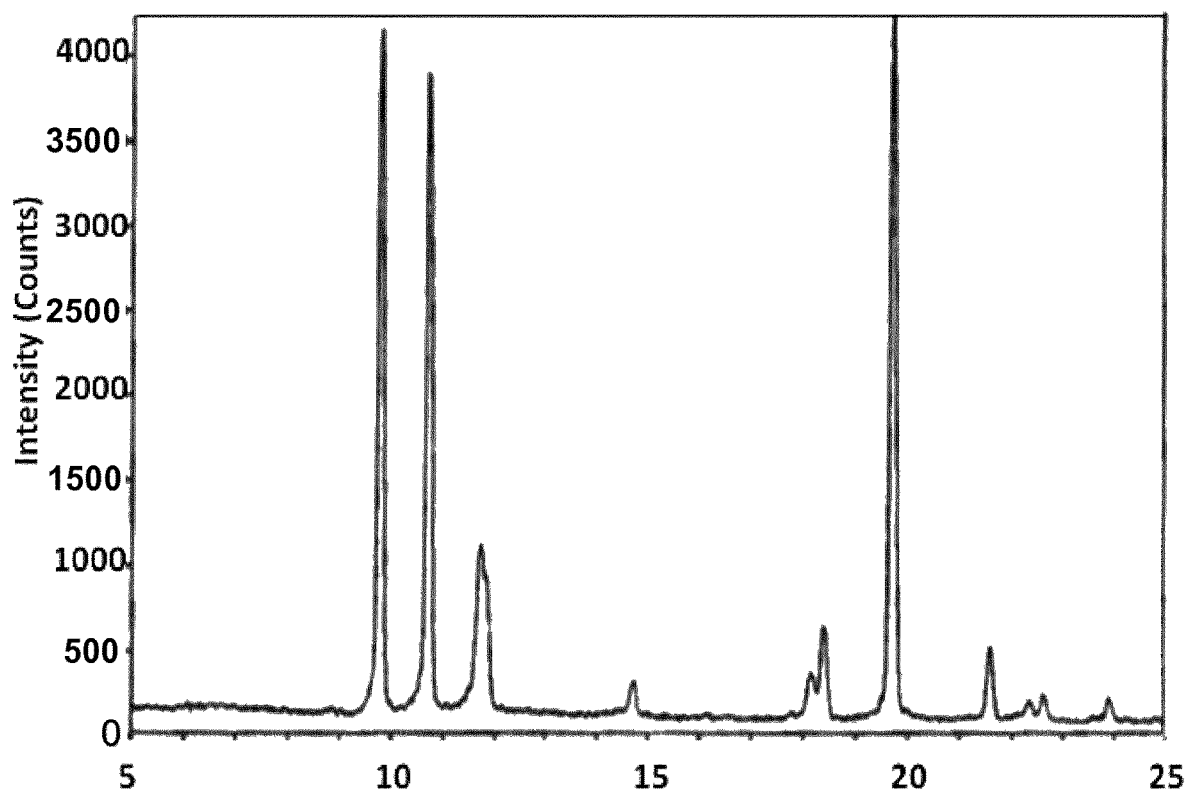
FIG. 6 presents the X-ray powder diffraction pattern for the anhydrous crystalline Form II of Compound A: A) re-crystallized from acetone; B) the cGMP API.
Figure 6B:
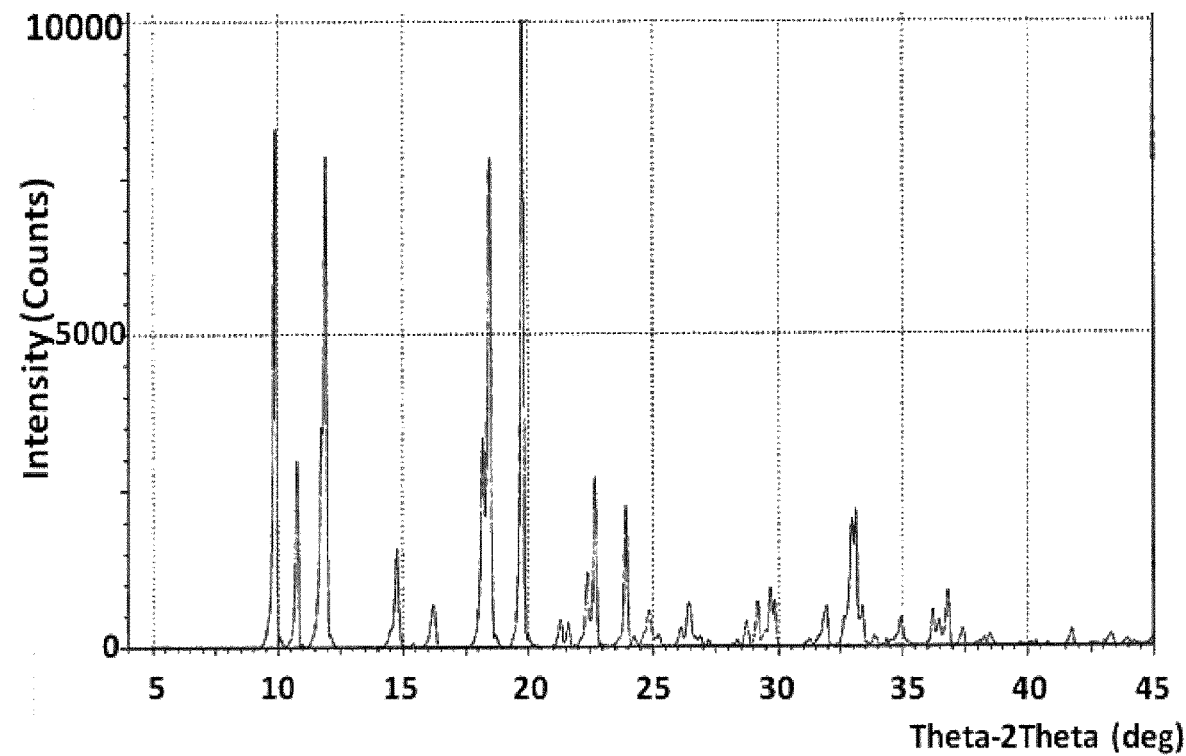

Anhydrous crystalline Form II is obtained by recrystallizing Compound A directly from solvents such as acetonitrile, acetone, hexane, dioxane, cyclohexane, diethylether, all solvents preferable water-free; phase equilibration of a suspension Compound A in hexane (Examples 7-13). Form II is a crystalline polymorph as shown by its XRPD (FIG. 6A and FIG. 6B, respectively). A variety of solvents could be used to produce Form II with good recovery. However, many of these solvents were not suitable for scaling due to the fact that the final product, long needle-like crystals, stuck to the sides of the flask. These sticky solids required manual scraping to remove them. Acetone emerged as the one solvent that produced a white material with a minimum loss of solids to the sides of the flask. Form II can reproducibly precipitate and crystallize from acetone with high purity and in high yields (88-93%) in a process that is scalable to the kilogram range and was validated according to current Good Manufacturing Practices (cGMP). The anhydrous crystalline Form II is stable under dry conditions but transforms to monohydrate Form I when exposed to ambient humidity at room temperature for three months (Example 20a), and transforms to Form III when exposed to 95% relative humidity for one week (Example 15). The API Form II transforms to Form I after exposure at 90% relative humidity for 3 hours (Example 20b) and to a mixture of Form I and Form III when exposed to ambient humidity at room temperature for four months (Example 20c). The API Form II can be obtained with high reproducibility and consistency when crystallized and dried according to well defined and controlled conditions. The API Form II is highly stable under dry storage conditions for at least two years and was tested in preclinical investigations and clinical trials. In a further embodiment, the present invention relates to

[4] The crystalline polymorph Form II of [2] or [3] having an X-ray powder diffraction pattern containing at least two, three, four, five, six, seven, eight, nine, ten, eleven or all of the following 2-theta values as measured using CuK$_\alpha$ radiation: 9.9, 10.8, 11.8, 11.9, 14.8, 16.2, 18.2, 18.5, 19.8, 21.3, 22.4, 23.9, 29.2 and 29.7, 33.0, 33.1.

According to the present invention, crystalline polymorphs of Compound A can be characterized in a variety of ways, e.g., in one embodiment, the crystalline polymorph of Compound A exhibits an XRPD pattern comprising at least one peak at a diffraction angle 2θ selected from the group consisting of 9.9°, 10.8° and 11.8°±0.2. In a related embodiment, the crystalline form of Compound A exhibits a XRPD pattern comprising 2θ values of 9.9° and 10.8°. In another related embodiment, the crystalline form of Compound A exhibits a XRPD pattern comprising 2θ values of 9.9° and 11.8°. In yet another related embodiment, the crystalline polymorph of Compound A exhibits a XRPD pattern comprising 2θ values of 10.8° and 11.8°. In still another related embodiment, the crystalline form of Compound A exhibits a XRPD pattern comprising 2θ values of 9.9°, 10.8° and 11.8°.

In one embodiment of the present invention, the X-ray powder diffraction pattern of the crystalline form of Compound A further exhibits at least one additional peak at a diffraction angle 2θ selected from the group consisting of 14.8° and 19.8°±0.2. In a related embodiment, the X-ray powder diffraction pattern of the crystalline form of Compound A further exhibits additional peaks at diffraction angles 2θ of both 14.8° and 19.8°±0.2.

In another embodiment of the present invention, the XRPD pattern of the crystalline form of Compound A further comprises at least one additional peak at a diffraction angle 2θ selected from the group consisting of 18.2° and 18.5°±0.2. In a related embodiment, the XRPD pattern of the crystalline polymorph of Compound A further comprise additional peaks at diffraction angles 2θ of both 18.2° and 18.5°±0.2. Thus, in one embodiment, the present invention relates to

[5] The crystalline polymorph Form II of any one of [2] to [4], wherein the X-ray powder diffraction pattern thereof comprises at least one additional peak at a diffraction angle 2θ selected from the group consisting of 14.8° and 19.8° and/or selected from the group consisting of 18.2° and 18.5°.

In a still further embodiment, the present invention relates to

[6] The crystalline polymorph Form II of any one of [2] to [5], wherein the ZnSe ATR-FT-IR absorption spectrum of the crystalline form contains at least two, three, four, five, six or all absorption peaks having a value selected from 906, 1340, 1447, 2869, 2901, 2951, and 3006-3012 cm$^{-1}$.

[7] The crystalline polymorph Form II of any one of [2] to [6], wherein the $^{13}$C solid-state NMR of the crystalline form contains resonances having at least two, three, four, five, six, seven or all of the following chemical shift values as expressed in ppm relative to TMS: 175.0; 65.3, 64.0; 45.8, 45.0; 49.3, 44.0, 39.5; 38.8; 28.9, 26.0; 15.4, 14.8.

In a further embodiment of the present invention, the $^{13}$C solid state NMR spectrum of invention crystalline polymorph Form of Compound A comprises at least one peak with chemical shift selected from the group consisting of approximately 64.0, 45.0, 38.8 and 26.0±0.2 ppm. In a related embodiment, crystalline polymorph Form II of Compound A comprise peaks with chemical shift of approximately 64.0 and 45.0±0.2 ppm. In another related embodiment, crystalline polymorph Form II of Compound A comprises peaks with chemical shifts of approximately 64.0 and 38.8±0.2 ppm. In yet another related embodiment, crystalline polymorph Form II of Compound A comprises peaks with chemical shifts of approximately 64.0 and 26.0±0.2 ppm. In still another related embodiment, crystalline polymorph Form II of Compound A comprise peaks with chemical shifts of approximately 45.0 and 38.8±0.2 ppm. In a further related embodiment, crystalline polymorph Form II of Compound A comprises peaks with chemical shifts of approximately 45.0 and 26.0±0.2 ppm. In yet another related embodiment, crystalline polymorph Form II of Compound A comprises peaks with chemical shifts of approximately 38.8 and 26.0±0.2 ppm.

In still another related embodiment, crystalline polymorph Form II of Compound A comprises peaks with chemical shifts of approximately 64.0, 45.0 and 38.8±0.2 ppm. In yet another related embodiment, crystalline polymorph Form II of Compound A comprises peaks with chemical shifts of approximately 64.0, 45.0 and 26.0±0.2 ppm. In a further related embodiment, crystalline polymorph Form II of Compound A comprises peaks with chemical shifts of approximately 64.0, 38.8 and 26.0±0.2 ppm. In yet another related embodiment, crystalline polymorph Form II of Compound A comprises peaks with chemical shifts of approximately 45.0, 38.8 and 26.0±0.2 ppm. In still another related embodiment, crystalline polymorph Form II of Compound A comprises peaks with chemical shifts of approximately 64.0, 45.0, 38.8 and 26.0±0.2 ppm. In a particular preferred embodiment, the present invention relates to

[8] The crystalline polymorph Form II of any one of [2] to [7] having an X-ray powder diffraction pattern containing the following 2-theta values: 9.9, 10.8, 18.5, 19.8±0.2; and wherein the $^{13}$C solid-state NMR of the crystalline form contains resonance having the following chemical shift values as expressed in ppm relative to TMS: 14.8, 15.4, 26.0, 28.9, 64.0, 65.3; and wherein the ZnSe ATR-FT-IR absorption spectrum of the crystalline form contains absorption peak having a value selected in the range of from 1340-1362 cm$^{-1}$±5 cm$^{-1}$.

[9] The crystalline polymorph Form II of any one of [2] to [8] having at least one of the following: an X-ray powder diffraction pattern substantially as shown in FIG. 6; a solid state $^{13}$C NMR spectrum substantially as shown in FIG. 9; an ATR-FT-IR spectrum substantially as shown in FIG. 10; and a DSC pattern substantially as shown in FIG. 7.

In another embodiment, the differential scanning calorimetry thermogram of the crystalline polymorph form of Compound A of the present invention has an endotherm peak in the range of about 133° C. to about 136° C., but lacks an endotherm peak in the range of about 50° C. to about 110° C.; see also FIG. 7. In a particular embodiment, the crystalline form further exhibits less than 1% weight loss [as determined by thermogravimetric analysis (TGA)] when subjected to heating from about room temperature up to about 110° C. at a heating rate of about 3° C. per minute; see also FIG. 8. Thus, in one embodiment, the present invention relates to

[10] The crystalline polymorph Form II of any one of [2] to [9], wherein the form exhibits less than 1% weight loss as determined by thermogravimetric analysis (TGA) up to a temperature of about 110° C. at a heating rate of about 3° C. per minute.

[11] The crystalline polymorph of [1], wherein the polymorph is the polymorph Form III.

There is provided in accordance with a preferred embodiment of the present invention a crystalline monohydrate form of Compound A (hereinafter referred to as "Form III"). Form III is similar to Form I in XRPD; $^{13}$CP/MAS $^{13}$C NMR; ATR-FT-IR patterns as described above but differs entirely from Form I in its DSC pattern, and has a very shallow and broad loss of water in the range of ca. 60-80° C. for Form III without the 104° C. DSC/TGA peak which is characteristic for Form I (re FIG. 4 vs. FIG. 3). Form I and Form III are two different polymorphs as shown by DSC/TGA. Without wishing to be bound by theory, inventors believe that, while the crystal matrices of Forms I and III are identical, water might be hydrogen-bonded in Form I crystals (re FIG. 14) while it might be physically absorbed, probably in crystal pores, in Form III, leaving the specific water-binding site of the crystal substantially unoccupied.

Monohydrate Form III can reproducibly precipitate and crystallize in high yields (92%) from a solution of Compound A in a mixture of acetone with 1.3 equivalent of water, without any impurities of Form II or Form I, in a process that is scalable to the kilogram range and was validated according to current Good Manufacturing Practices (cGMP); Example 14. Like Form II, Form III is less sticky than Form I, and therefore easier to filter, scrape and handle than previously known solid Compound A. Form III is stable under various storage conditions for at least two years and was tested in preclinical investigations and clinical trials.

Monohydrate Form III cannot be generated by exposing monohydrate Form I to 95% relative humidity (Example 21), nor does such treatment create another crystalline form that contains more than one molecule of water per Compound A molecule. Thus, in this aspect, the present invention inter alia relates to

[12] The crystalline polymorph Form III of [11] having an X-ray powder diffraction pattern containing at least two, three or all of the following 2-theta values as measured using CuK$_\alpha$ radiation: 8.8, 12.3, 17.3, 17.5, 17.8 and 23.0; see also Table 2.

[13] The crystalline polymorph Form III of [11] or [12], wherein said X-ray powder diffraction pattern also contains at least one of the following 2-theta values as measured using CuK$_\alpha$ radiation: 12.3, 19.9, 21.6, 24.6, 26.3, 31.6 and 35.4; see also Table 2.

[14] The crystalline polymorph Form III of any one of [12] to [13], wherein said X-ray powder diffraction pattern is substantially free of peaks having 2-theta values in the range of from 10.8-11.9.

Figure 2:
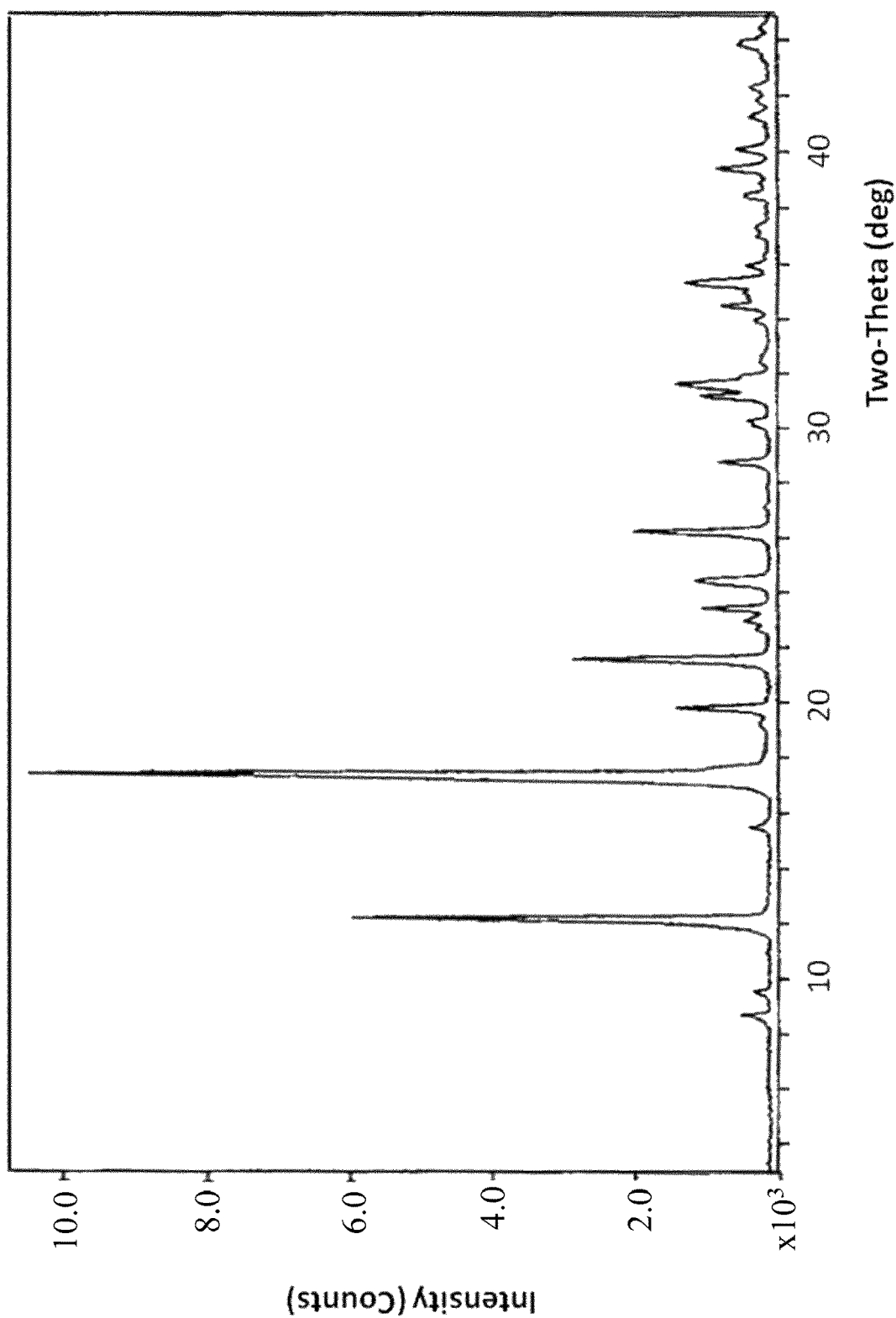
FIG. 2 presents X-ray powder diffraction patterns for a monohydrate crystalline polymorph form of Compound A (Form III).

[15] The crystalline polymorph Form III of any one of [11] to [14] having an X-ray powder diffraction pattern containing at least one of the following 2-theta values as measured using CuK$_\alpha$ radiation: 12.2, 17.3, 19.9, 21.6, 24.6, 26.3 and 31.6, and wherein said X-ray powder diffraction is substantially free of peaks having 2-theta values in the range of from 10.8-11.9; see also FIG. 2.

[16] The crystalline polymorph Form III of any one of [11] to [15], wherein said X-ray powder diffraction pattern contains at least two, three, four, five or all of the following 2-theta values as measured using CuK$_\alpha$ radiation 12.2, 17.3, 17.5, 19.9, 21.6, 24.6, 26.3. 31.2 and 35.4.

[17] The crystalline polymorph Form III of any one of [11] to [16], wherein the $^{13}$C solid-state NMR of the crystalline form contains resonances having at least two, three, four or all of the following chemical shift values as expressed in ppm relative to TMS: 67.56, 54.60, 47.07, 41.49, 30.70 and 13.77.

[18] The crystalline polymorph Form III of any one of [11] to [17], wherein the $^{13}$C solid-state NMR of the crystalline form contains at least two, three, four or all differences in chemical shift between the resonance having the largest chemical shift and other resonances selected from 107.3, 120.3, 127.9, 133.4, 144.2 and 161.1.

[19] The crystalline polymorph Form III of any one of [11] to [18], wherein the ZnSe ATR-FT-IR absorption spectrum of the crystalline form contains at least two, three, four, five, six or all absorption peaks having a value selected from 1039, 1353, 1369 1369, 1388, 2918, 2974 and 3088 cm$^{-1}$.

[20] A crystalline monohydrate form of the compound (S)-2-ethyl-8-methyl-1-thia-4,8-diazaspiro[4.5]decan-3-one having an X-ray powder diffraction pattern containing the following 2-theta values: 12.3, 17.3, 17.5, 19.9, 21.6±0.2; and wherein the $^{13}$C solid-state NMR of the crystalline form contains resonance having the following chemical shift values as expressed in ppm relative to TMS: 13.77, 30.70, 67.56; and wherein the ZnSe ATR-FT-IR absorption spectrum of the crystalline form contains an absorption peak having a value selected from 1353, 1369 and 1388±5 cm$^{-1}$; and wherein the crystalline form shows a very broad endotherm at 58-94° C. and an endotherm having an onset at 133.9° C.

Figure 5:
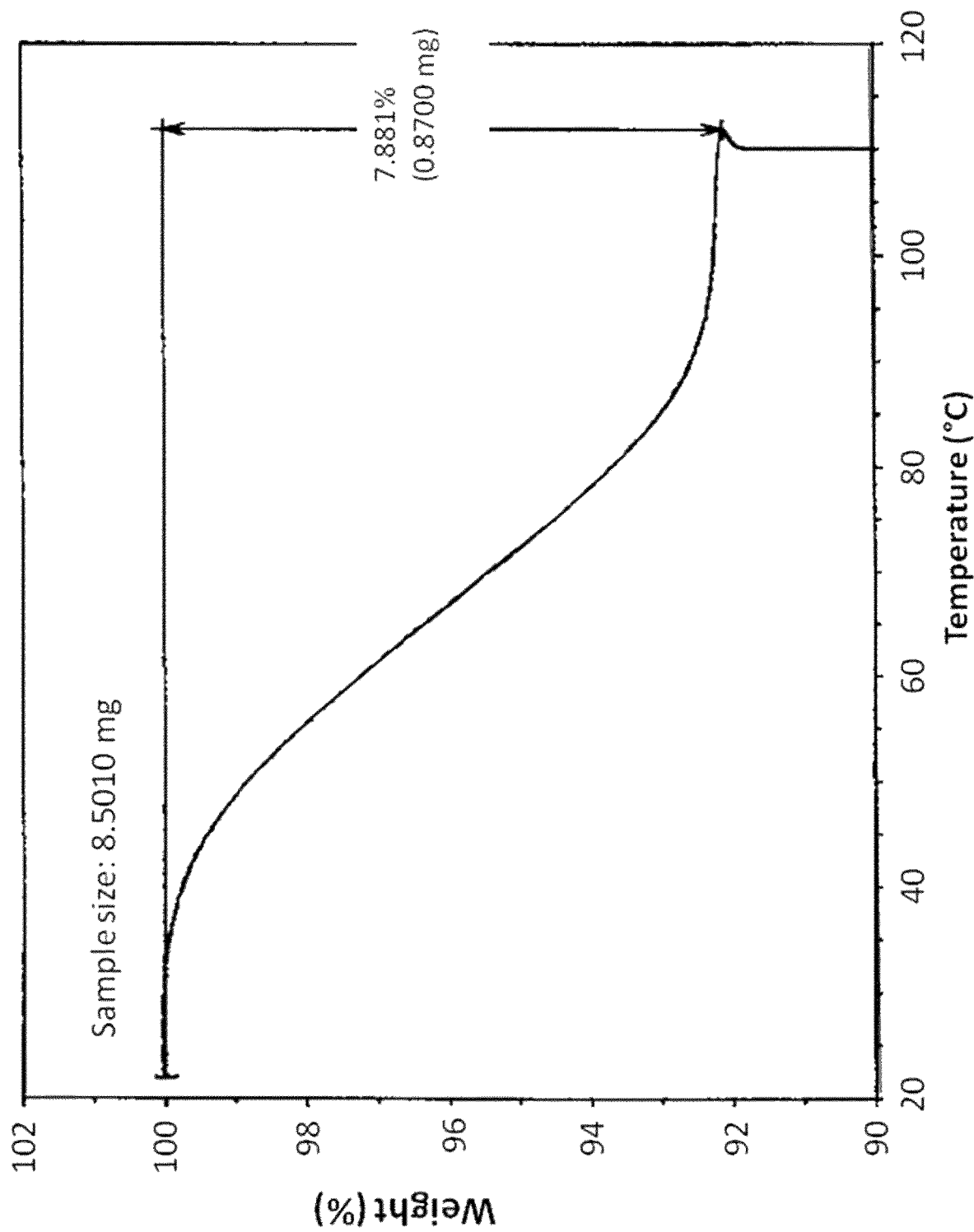
FIG. 5 presents the result of thermogravimetric analysis (TGA) for a monohydrate crystalline polymorph form of Compound A (Form III; the API). The TGA indicates a 7.8% weight loss when heated to a temperature up to about 110° C. Moisture by Karl Fischer analysis is 7.7% as expected from a stoichiometric monohydrate.

[21] The crystalline polymorph Form III of any one of [11] to [18], wherein the crystalline form contains one molecule of water per molecule of Compound A as shown in FIGS. 5 and 15.

Another embodiment of the present invention encompasses crystalline polymorphs of Compound A which are substantially free of solvate. In a presently preferred embodiment, the crystalline forms are substantially free of water.

In still another embodiment of the present invention, the crystalline polymorph forms of Compound A exhibit a XRPD pattern comprising at least one peak at a diffraction angle 2θ selected from the group consisting of 9.9°, 10.8° and 11.8°±0.2, wherein the Form is substantially free of water. In a particular embodiment, the form contains less than about 2% by weight water. In a further embodiment, the present invention relates to

[22] The crystalline polymorph Form of any one of I to III of any one of [1] to [21], whenever in substantially pure form, i.e. free of impurities and substantially consisting of one polymorph form only.

There are also provided, in accordance with embodiments of the invention, methods for preparing crystalline Forms I, II, and III of Compound A; for converting Form I into Form II and vice versa; and for converting Form II into Form III. There are also provided, in accordance with embodiments of the invention, pharmaceutical compositions comprising one or more of crystalline Form II or III Compound A and a pharmaceutically acceptable carrier.

Accordingly, in a further aspect the present invention relates to the following embodiments:

A process for preparing the crystalline polymorph Form of Compound A of any one of [1] to [22]:

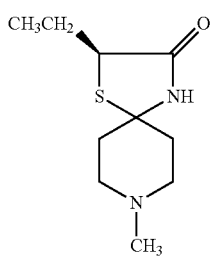

comprising the steps of:
(a) dissolving Compound A in appropriate solvent;
(b) if necessary, cooling the resulting solution;
(c) waiting sufficient time for the crystalline form to crystallize, until Form II crystals precipitate; and
(d) filtering said crystalline form.

The process of [23], wherein the crystalline Form is polymorph Form II of any one of [2] to [10] and the solvent is selected from the group consisting of acetone, acetonitrile, cyclohexane, hexane, dioxane and mixed solvents of ethanol and acetonitrile.

The process of [23], wherein the crystalline Form is polymorph Form III of any one of [11] to [20] and obtained by adding 1.3 moles of de-ionized water to the solution of Compound A in acetone.

The process of [23], wherein polymorph Form III is obtained by a re-slurry of Compound A and/or polymorph Form II in de-ionized water and filtration.

The process of [23], wherein the crystalline Form is polymorph Form I of [1] and obtained by crystallization from water-miscible organic solvents that contain traces of water (ethanol, ethyl acetate, isopropanol, tert-butylmethylether, tetrahydrofuran), water or slow evaporation of a solution of the compound dissolved either in water or ethyl acetate.

The process of [23], wherein the crystalline Form is a mixture of a crystalline polymorph Forms I and II and the solvent is selected from the group consisting of toluene, dichloromethane, 1-butanol, or diethyl ether.

A process for converting polymorph Form II into polymorph Form III, comprising maintaining the crystalline polymorph Form II of any of [2] to [10] at room temperature and at least 95% relative humidity for a time sufficient for conversion to a crystalline polymorph Form III of any of [11] to [20]; see also FIG. 15.

A process for converting polymorph Form I into polymorph Form II of any of [2] to [10] comprising one of the following:
(a) maintaining a crystalline Form I at an elevated temperature below the melting point of the crystalline form for a sufficient time to convert the crystalline Form into said crystalline polymorph Form II;
(b) suspending a crystalline polymorph Form I in a solvent selected from the group consisting of acetonitrile, cyclohexane, hexane, dioxane and mixed solvents of ethanol and acetonitrile, waiting sufficient time for the crystalline form of any of [2] to [10] to crystallize, and filtering said crystalline form; and
(c) heating the crystalline polymorph Form I above its melting point to form a molten mass and cooling the molten mass.

The present invention encompasses several crystalline polymorph forms of Compound A that can readily be distinguished from one another, inter alia, by virtue of the presence or absence of solvate, using techniques such as those known in the art, such as single crystal X-ray, X-ray powder diffraction (XRPD), differential scanning calorimetry (DSC), thermogravimetric analysis (TGA) and solid-state cross-polarization magic angle spinning nuclear magnetic resonance (CP/MAS $^{13}$C NMR), ATR FT-IR as well as analytical techniques developed in the future. Thus, in one embodiment the present invention relates to The process of any one of [23] to [30], wherein the resultant crystalline polymorph Form I, II or III is selected by identifying the polymorph according its X-ray powder diffraction pattern of 2-theta values as measured using CuK$_\alpha$ radiation, ZnSe ATR-FT-IR absorption spectrum endothermic peaks as measured by DSC, TGA and/or resonance as measured by $^{13}$C solid-state NMR.

A process for stably maintaining a crystalline polymorph Form II of any one of [2] to [10] comprising maintaining said crystalline at room temperature in a dry atmosphere.

Another embodiment of the present invention encompasses pharmaceutical compositions comprising crystalline polymorph forms of Compound A which are substantially free of solvate, and a pharmaceutically acceptable carrier, diluent or excipient therefor. In some embodiments, pharmaceutical compositions contemplated herein further comprise additional forms of Compound A in a crystalline, solvate or amorphous form. Thus, in a further embodiment, the present invention relates to A pharmaceutical composition comprising a crystalline polymorph of any one of [1] to [22] and at least one pharmaceutically acceptable excipient or carrier.

In a particular embodiment, the crystalline polymorph form of Compound A is an anhydrous form. In another particular embodiment, the pharmaceutical composition comprises at least 70% by weight of the crystalline Form II based on the total weight of Compound A in the composition, preferably 80%, 90%, 95% or 99% by weight of the crystalline form. In a particular embodiment, an additional monohydrate polymorph form of Compound A is present. In another particularly preferred embodiment, the pharmaceutical composition comprises at least 70% by weight of the crystalline Form III based on the total weight of Compound A in the composition, preferably 80%, 90%, 95% or 99% by weight of the crystalline form.

Pharmaceutical compositions according to the present invention that are intended for parenteral administration can include crystalline polymorph form of Compound A for dissolution or suspension in aqueous or non-aqueous media that are suitable for use in sterile injection or infusion solution. These pharmaceutical compositions containing Compound A polymorph forms, or the media intended for their dissolution or suspension, may contain pharmaceutically acceptable antioxidants, buffers, and compounds which render the ready-to-use formulation substantially isotonic with the blood of the intended recipient. The pharmaceutical compositions may also contain preserving agents, such as e.g. bacteriostatic or antibacterial compounds; solubilizing agents, stabilizing agents, colorants, and odorants. They may also contain one or more adjuvant(s) and/or therapeutically active agent(s) in addition to the crystalline polymorph forms of the present invention. The compositions may be presented in unit-dose or multi-dose containers, for example sealed ampoules and vials. In a further embodiment, the present invention relates to The pharmaceutical composition of [33], wherein the polymorph Form II or Form III is present in an amount of between 1 mg and 100 mg and preferably between 10 mg and 50 mg in the formulation, preferably wherein the formulation is granulated.

Pharmaceutical compositions intended for oral administration may be presented as discrete units such as capsules or tablets; or as powders or granules. Suitable excipients for tablets or hard gelatine capsules include lactose, maize starch or derivatives thereof, stearic acid or salts thereof. Suitable excipients for use with soft gelatine capsules include for example vegetable oils, waxes, fats, semi-solid, or liquid polyols etc.

In one embodiment of the invention, oral tablets can be manufactured by direct compression of Compound A anhydrous crystalline Form II. It is known generally that the advantages of direct compression include few manufacturing steps involved, physical stability and elimination of heat and moisture. Direct-compression tablets according to the invention can additionally contain binders, disintegrants, and colorants such as are familiar to those knowledgeable in the art. In another embodiment, pre-manufactured oral capsules contain Compound A crystalline Form III along with excipients. Following compression of the tablets, or closure of the capsules, pharmaceutically acceptable coatings can be applied to these presentations of the invention in order to further modify release characteristics of the active agent in the gastrointestinal tract. The selection of the optimal release site depends on the type of disease, the intended plasma peak concentrations, the intended plasma time/concentration-profile and the intended time/concentration profile at the target site. In a further embodiment, the present invention relates to A process for preparing a medicament based on a formulation of crystalline polymorph Form II of any one of [2] to [10], which is suitable for oral administration, wherein the formulation is directly compressed into tablets.

A process for preparing a medicament based on a formulation of crystalline polymorph Form III of any one of [11] to [22], which is suitable for oral administration, wherein it is mixed with one or more excipient(s) (pregelatinized starch, microcrystalline cellulose, colloidal silicon dioxide, and stearic acid) and the mixture is filled in size 4, white opaque, hard gelatin, two-piece capsules to provide 5 mg or 10 mg polymorph Form III per capsule, which can be used as an oral formulation for immediate release in the gastrointestinal tract.

According to the invention, the daily dose of Compound A crystal forms can vary between 1 mg and 100 mg. In a preferred embodiment of the invention, the daily dose can vary between 5 mg and 80 mg. In a more preferred embodiment, the daily dose varies between 10 mg and 50 mg. The exact amount of single doses, the frequency and schedule of administration of the compounds, and the duration of treatment will be determined according to the judgment of the attending physician considering such factors as age, condition and size of the subject as well as severity of the symptoms being treated, and the observed undesired effects of treatment.

Another embodiment of the present invention encompasses use of any crystalline polymorph forms of Compound A, or a pharmaceutical composition comprising such crystalline polymorph form, and pharmaceutically acceptable salts thereof in the preparation of a pharmaceutical composition for stimulating the M1 muscarinic acetylcholine receptor subtype 1 (the "M1 receptor"), so that diseases or conditions that are related to impaired cholinergic function (specifically, an understimulation of M1 receptors) can be treated, ameliorated, or prevented. Thus, in a further embodiment, the present invention relates to A crystalline polymorph Form of any of [1] to [22] for use in treating a medical condition that is responsive to treatment, amelioration, or prevention with a muscarinic receptor agonist, preferably wherein the daily doses is about 10 mg and 50 mg.

The crystalline polymorph Form for use in accordance with [37], wherein the condition is include diseases or conditions associated with impaired cholinergic function, diseases or conditions in which there is an imbalance in cholinergic function, diseases or conditions associated with impaired activity of acetylcholine receptors, and diseases or conditions associated with impaired activity of M1 receptors. Such diseases and conditions include, but are not limited to: senile dementia of Alzheimer's type; Alzheimer's disease (AD); Lewy body dementia, mixed Alzheimer's and Parkinson's disease; atrophy; multi-infarct dementia (MID), fronto-temporal dementia; vascular dementia; stroke/ischemia, MID combined with stroke/ischemia/head injury; combined MID and AD; human head injury; traumatic brain injury; age-associated memory impairments; transient global amnesia syndrome; mild cognitive impairment (MCI); MCI conducive to AD; cognitive dysfunction (including forgetfulness, acute confusion disorders, attention-deficit disorders, focus and concentration disorders); hallucinatory-paranoid states, emotional and attention disorders; sleep disorders; post-operative delirium; adverse effects of tricyclic antidepressants, adverse effects of certain drugs used in the treatment of schizophrenia and Parkinson's disease; xerostomia, anomia, memory loss and/or confusion; psychosis; schizophrenia, schizophrenia comorbid with AD, late onset schizophrenia, paraphrenia, schizophreniform disorders; anxiety, bipolar disorders, mania; mood stabilization; cognitive impairments after removal of certain gliomas; synucleinopathies (Parkinson's disease, dementia with Lewy bodies, multiple system atrophy); tauopathies (primary age-related tauopathy; chronic traumatic encephalopathy; Pick's disease; progressive supranuclear palsy; corticobasal degeneration), tardive dyskinesia; oxidative stress during oxygen therapy (e.g., retinopathy of prematurity); aphasia; postencephalitic amnesic syndrome; sepsis-associated encephalopathy; sepsis-induced delirium; AIDS-related dementia; memory impairments in autoimmune diseases including lupus, multiple sclerosis, Sjogren's syndrome, chronic fatigue syndrome, and fibromyalgia, splenomegaly, memory impairments in atypical depression or schizophrenia; chemotherapy-induced cognitive deficit; alcoholic dementia, cognitive deficits following bypass surgery and grafting, hypothyroidism-related dementia, autism related cognitive impairment, Down's syndrome, cognitive disorders due to drug abuse or drug withdrawal including nicotine, cannabis, amphetamine, cocaine, Attention Deficit Hyperactivity Disorder (ADHD), pain, rheumatism, arthritis and terminal illness; xerophthalmia, vaginal dryness, skin dryness; immune dysfunctions; neurocrine disorders and dysregulation of food intake, including bulimia and anorexia; obesity; congenital ornithine transcarbamylase deficiency; olivopontocerebellar atrophy; alcohol withdrawal symptoms; substance abuse including withdrawal symptoms and substitution therapy, Huntington's chorea; progressive supranuclear palsy; Pick's disease; Friedreich's ataxia; Gilles de la Tourette disease; Down's syndrome; prion diseases; glaucoma; presbyopia; autonomic disorders including dysfunction of gastrointestinal motility and function such as inflammatory bowel disease, irritable bowel syndrome, diarrhea, constipation, gastric acid secretion and ulcers; urinary urge incontinence, asthma, COPD; central or peripheral nervous system disease states due to dysfunction in one or more of the following: brain, nervous system, cardiovascular system, immune system, neurocrine system, gastrointestinal system, or endocrine and exocrine glands, eye, cornea, lungs, prostate, or other organs where the cholinergic function is mediated by muscarinic receptor subtypes, wherein said dysfunction involves: brain amyloid-mediated disorders; glycogen synthase kinase (GSK3-beta)-mediated disorders; tau protein hyperphosphorylation-mediated damages, dysfunctions or diseases; CNS and PNS hypercholesterolemia- and/or hyperlipidemia-mediated damages, dysfunctions or diseases; Wnt-mediated signaling abnormalities; impairment of neuroplasticity; hyperglycemia; diabetes; endogenous growth factors-mediated diseases, or combination of additional risk factors; or disease states that involve apolipoprotein E; or disturbances in which a cholinergic dysfunction has been implicated, including: senile dementia of Alzheimer's type, Alzheimer's disease (AD), delay of onset of AD symptoms in a patient at risk for developing AD, Lewy body dementia, Lewy body disease, cerebral amyloid angiopathy (CAA), cerebral amyloidosis, fronto-temporal dementia, vascular dementia, hyperlipidemia, hypercholesterolemia, multi-infarct dementia (MID), stroke ischemia, MID combined with stroke/ischemia/head injury, combined MID and Alzheimer's disease, human head injury, age-associated memory impairments, mild cognitive impairment (MCI), MCI conducive to AD, bipolar disorder, mania, schizophrenia, non-affective schizophrenia, paraphrenia, immune dysfunctions, neurocrine disorders and dysregulation of food intake, including bulimia and anorexia, weight control, obesity, and inflammation; with special attention being given to the support of immunotherapy for inflammatory disorders.

The pharmaceutical composition of [33] or [34], which also comprises at least one additional pharmacologically active compound preferably selected from the group consisting of: cholinesterase inhibitors, nicotinic agonists, cholinergic precursors and cholinergic enhancers, nootropics, peripheral antimuscarinc drugs, M2 muscarinic antagonists, M4 antagonists, benzodiazepine inverse agonists, sigma-1 agonists, antidepressants, tricyclic antidepressants or antimuscarinic drugs used in treatment of Parkinson's disease (PD) or depression, antipsychotic and antischizophrenic agents, glutamate antagonists and modulators, metabotropic glutamate receptor agonists, NMDA antagonists, AMPA agonists, acetyl-L-carnitine, MAO-B inhibitors, peptides and growth factors, cholesterol-lowering agents, antioxidants, GSK-3 beta inhibitors, Wnt-ligands, PKC-activators, beta- or gamma-secretase inhibitors, beta-amyloid degrading agents, activators of enzymes involved in degradation of beta-amyloid such as activators of neprilysin, insulin degrading enzyme or endothelin converting enzyme, beta-amyloid anti-aggregation agents, chelating agents, antibodies and immunotherapeutic compounds against beta-amyloids, antibodies and immunotherapeutic compounds against tau protein pathology, antibodies and immunotherapeutic compounds against alpha-synuclein pathology, compounds that bind to amyloids, cyclooxygenase (COX)-2 inhibitors, non-steroidal antiinflammatory drugs, estrogenic agents, estrogenic receptor modulators, steroidal neuroprotectants, and spin trapping pharmaceuticals.

In accordance with the present invention, pharmaceutical compositions based on crystalline polymorphs of Compound A that can be used to treat or prevent the above-mentioned diseases and disorders which are responsive to stimulation of the M1 muscarinic receptor may be prepared in different presentations, and may be administered using different routes of administration. Guidance regarding formulations that are suitable for various types of administration can be found for example in Remington: The Science and Practice of Pharmacy (2000) by the University of Sciences in Philadelphia, ISBN 0-683-306472. Therefore, the present invention also provides methods for administering drugs to treat or prevent diseases or conditions which are responsive to agonistic stimulation of the M1 muscarinic receptor. Thus, in a further embodiment, the present invention relates to A method of treating subject, i.e. patient suffering from a medical condition as defined in [37] or [38] comprising administering a therapeutically effective amount of a crystalline polymorph Form of any one of [1] to [22] or a pharmaceutical composition of [33], [34], [38] or [39] to a subject in need thereof.

The crystalline polymorph Forms of the present invention and its various aspects and embodiments as characterized above will now be illustrated by way of reference to the following Figures and Examples. Furthermore, the disclosure content of the foregoing description in the background of the invention as far as applicable forms part of the disclosure of the present invention. It is to be understood that this invention is not limited to the particular methodology, protocols, cell lines, excipients, carriers, and reagents described herein as such. It is also to be understood that the terminology used herein is for the purpose of describing particular embodiments only, and is not intended to limit the scope of the present invention, which will be limited only by the appended claims.

EXAMPLES

The following Examples help illustrate embodiments of the invention. It will be appreciated that the invention is not intended to be limited by the foregoing description, which is meant to help illustrate embodiments of the invention.

Methodology:

Materials

Compound A (m.p. 134° C.; purity by HPLC (achiral) 99.9%; purity by HPLC (chiral) 99.7-100% was used in the crystallization studies.

The water was de-ionized and passed through an ion-exchange system.

All solvents and reagents were analytical grade.

Melting points were recorded on an Electrothermal 9100 capillary melting point apparatus and are uncorrected.

Measurement Method and Conditions for X-Ray Powder Diffraction (XRPD)

Apparatus: Philips model PW-1050/70 X-ray Diffractometer

Graphite monochromator

Voltage: 40 kv

Current: 28 mA

Slit: receiving slit 0.2 mm, scattering slit 1 mm

Two-Theta Min: 3.00

Two-Theta Max: 40.00

Step size: 0.05

Count time: 0.50 sec

Radiation source: $CuK_\alpha$

Unless noted otherwise, the 2-theta values are listed rounded to the nearest 0.1, ±0.2.

For the API crystal forms XRPD was also performed in compliance with USP <941>.

The person skilled in the art will appreciate that the XRPD patterns of the same sample (taken on the same or different instruments) may exhibit variations in peak intensity at the different 2θ values. The person skilled in the art will appreciate that the XRPD patterns of different samples of the same polymorph (taken on the same or different instruments) may also exhibit variations in peak intensity at the different 2θ values. XRPD patterns can be substantially the same pattern even though they have corresponding 2θ signals that vary in their peak intensities.

Thermal Analyses:

Measurement Method and Condition for Differential Scanning Calorimetry (DSC) and Thermogravimetric Analysis (IGA)

Apparatus: METTLER TG50
Software: METTLER TOLEDO STAR® System
Range: 30-200° C.
Heating rate: 5° C./min
Pan: Aluminum Standard 40 µl
Purge gas: nitrogen at flow rate 80 ml/min For the API the thermal properties of the tested crystal forms were characterized also by modulated differential scanning calorimetry (DSC Q 100, TA Instruments) and TGA (TGA Q500, TA Instruments) with data analysis performed via a thermal analyzer (Universal Analysis 2000, TA Instruments). A heating rate of 3° C./min and a modulated cooling rate of 1° C./min were employed over temperature ranges of 35-200° C. for DSC and a heating rate of 10° C./min was employed to 110° C. and held for 250-360 minutes for TGA. The TGA analysis of the API sample was performed with a heating rate of 10° C./min to a final temperature of 175° C. and analyzed at 115° C.

Measurement Method and Conditions for ZnSe ATR-FT-IR Absorption Spectrum

Spectrometer: Nicolet 380
Detector: DTGS KBr
Smart Accessory: Smart Multi-Bounce ZnSe HATR
Number of sample scans: 36
Resolution: 4.000

Unless noted otherwise, IR absorption peaks are listed in terms of $cm^{-1} \pm 5\ cm^{-1}$.

Measurement Method and Conditions for Solid-State CP/MAS $^{13}$C NMR

Spectrometer: Bruker Advance-500
Spectra were measured in a 4 mm CP-MAS probe head at 125.76 MHz.
All spectra were referenced to tetramethyl silane (TMS) using the carbonyl carbon of glycine (176.03) as a secondary reference.
The rotor frequency was 5.0 kHz.
Two-pulse phase modulation (TPPM) was used for proton decoupling
The contact period was 1000 µs.
4 k of data points were acquired in 40 ms.
Recycle delays for all experiments were 5.0 s.
Unless noted otherwise, NMR peaks are listed with chemical shifts in ppm relative to TMS rounded to the nearest 0.1±0.1.

Single Crystal X-Ray

A single crystal of the tested compound was attached to a glass fiber, with epoxy glue, and transferred to a Bruker SMART APEX CCD X-ray diffractometer equipped with a graphite-monochromator. The system was controlled by a pentium-based PC running the SMART software package[1]. Data were collected at 173K using MoKα radiation (λ=0.71073 Å). Immediately after collection, the raw data frames were transferred to a second PC computer for integration and reduction by the SAINT program package[2]. The structure was solved and refined by the SHELXTL software package[3].

1. SMART-NT V5.6, BRUKER AXS GMBH, D-76181 Karlsruhe, Germany, 2002.
2. SAINT-NT V5.0, BRUKER AXS GMBH, D-76181 Karlsruhe, Germany, 2002.
3. SHELXTL-NT V6.1, BRUKER AXS GMBH, D-76181 Karlsruhe, Germany, 2002.

Microscopic observations of the various crystals were made using Nikon TMS inverted light microscope. Photomicrographs were obtained using digital camera (Nikon Japan, MDC Lens). Crystals were imaged on a glass slide.

Scanning Electron Microscopy (SEM) of the various crystals was evaluated at 20 kV and magnification ranging from ×25 to ×3000.

Hygroscopicity

For the APIs the water uptake was evaluated in a dynamic moisture uptake experiment (SGA-100 Symmetric Vapor Sorption Analyzer, VTI Corporation). The dynamic moisture uptake profile for API (Form III) was completed in 10% increments with sorption from 40% to 90% RH, followed by desorption to 2% RH in 10% increments from 90% to 10% and 1% increments from 10% to 2%. The dynamic moisture uptake profile of API (Form II) was completed in 10% increments with sorption from 40% to 90% RH followed by desorption to 10%.

Moisture

The moisture of the API was determined on a Settler Toledo DL35 Karl Fischer Titrator.

Aqueous Solubility

Aqueous solubility was carried out by preparing 50 mg of API Monohydrate (Form III) in 2 ml of deionized water. The sample was prepared in triplicate and the preparations were rotated for 2 days at room temperature. Following rotation, the mixture remained undisturbed for 3 hours allowing any undissolved API to settle. The supernatant was filtered into scintillation vials using a 4 mm 0.45 microM PTFE filter. A 1 in 40 dilution was made by pipetting 25 microliter into 975 microliter of sample solvent. The resulting dilution was placed into vials for HPLC analysis.

Example 1: Crystalline Form I Compound A a) To Compound A (1.37 g) was added ethyl acetate (7 ml), and the mixture was heated to dissolve the compound. The clear solution was cooled at room temperature overnight. Solid material which appeared to the naked eye to be crystalline formed in the solution. This material was collected by filtration and dried at room temperature under vacuum to give 1.06 g of solid Compound A. X-ray powder diffraction, which yielded the following 2-theta values, d-spacings and relative intensities, confirmed that the material was crystalline (FIG. 1):

| 2θ (±0.1) | d (Å, unrounded) | I/I$_0$ |
| --- | --- | --- |
| 8.8 | 10.069 | 5.3 |
| 9.6 | 9.182 | 1.8 |
| 12.3 | 7.224 | 51.9 |
| 15.6 | 5.699 | 2.2 |
| 17.5 | 5.067 | 100.0 |
| 19.3 | 4.611 | 0.6 |
| 19.9 | 4.464 | 9.3 |
| 21.6 | 4.110 | 16.0 |
| 22.7 | 3.908 | 1.1 |
| 23.0 | 3.861 | 1.8 |
| 23.5 | 3.783 | 5.1 |
| 24.5 | 3.627 | 5.8 |
| 26.3 | 3.385 | 9.1 |
| 27.2 | 3.275 | 0.2 |
| 28.8 | 3.101 | 3.0 |
| 30.3 | 2.948 | 1.1 |

| 2θ (±0.1) | d (Å, unrounded) | I/I₀ |
|---|---|---|
| 31.3 | 2.858 | 5.4 |
| 31.6 | 2.826 | 5.9 |
| 32.5 | 2.756 | 0.6 |
| 34.0 | 2.636 | 0.8 |
| 34.5 | 2.598 | 3.0 |
| 35.4 | 2.537 | 7.0 |
| 36.0 | 2.495 | 1.8 |
| 37.1 | 2.426 | 0.7 |
| 37.4 | 2.403 | 0.6 |
| 38.5 | 2.337 | 1.4 |
| 39.0 | 2.310 | 0.4 |
| 39.4 | 2.283 | 2.6 |

Solid-state CP/MAS $^{13}$C NMR of the crystalline material yielded a spectrum having the following chemical shifts ($\delta_c$ in ppm, unrounded): 13.269, 30.147, 43.613, 40.968, 52.151, 54.081, 46.585, 67.088, 174.360.

ATR-FT-IR yielded a spectrum having the following absorption peaks (cm$^{-1}$, unrounded): 673, 724, 774, 808, 826, 945, 984, 1012, 1026, 1070, 1110, 1144, 1194, 1278, 1291, 1352, 1370, 1388, 1426, 1438, 1467, 1676, 2685, 2791, 2802, 2842, 2921, 2941, 2974, 3023, 3159, 3429. (FIG. 10)

DSC of Compound A crystal Form I (FIG. 3A) shows an endothermic peak at 107.1° C. (onset at 104.8° C.) corresponding to release of water physically occluded in the crystal structure and an endothermic peak at 134.6° C. (onset at 133.8° C.) corresponding to the melting point. After the melting, thermal decomposition occurred. The broad low temperature peak characteristic to Form III at 61-77° C. (re FIG. 4) was not observed in this case. Further information on crystal Form I is described in Example 27. The TGA of Form I showed a 5.2% % weight loss when heated to a temperature up to about 115° C. which indicates less than a stoichiometric percentage of water required for a full monohydrate of Compound A (for a stoichiometric monohydrate the theoretical number for the water is 7.76%).

b) Form I can be obtained by slow evaporation at 25° C. of Compound A dissolved in ethyl acetate. The XRPD shows that the compound is crystalline and has the XRPD pattern of Form I as shown in FIG. 1A, DSC shows only the characteristic endotherms of Form I at 106.9° C. (onset 104.9° C.), 135.8° C. (onset 133.9° C.).

Example 2: Crystalline Form I Compound A a) To Compound A (1.07 gr.) was added water (25 ml), and the mixture was heated to dissolve the compound. The clear solution was cooled at room temperature overnight and the precipitated crystals were collected by filtration. The resulted crystals were dried to give 0.82 gr. of Compound A. m.p. 134.7-135.2° C.

x-ray powder diffraction (XRPD): [2 Th, d (A), I/I0] (8.8, 10.052, 6), (9.6, 9.174, 4), (12.3, 7.223, 73.9), (15.6, 5.696, 4.9), (17.3, 5.126, 81.3), (17.5, 5.066, 100), (19.3, 4.6, 1.8), (19.9, 4.461, 20.3), (21.6, 4.106, 39.8), (23.1, 3.857, 5.6), (23.5, 3.782, 6.3), (24.5, 3.632, 12.2), (26.3, 3.388, 20.9), (27.2, 3.276, 0.5), (28.8, 3.097, 8.4), (30.3, 2.945, 3.6), (31.2, 2.865, 9.8), (31.6, 2.83, 14.1), (32.5, 2.751, 2.6), (34, 2.634, 3.3), (34.5, 2.597, 5.9), (35, 2.564, 4.8), (35.4, 2.533, 9.3), (36, 2.493, 5.9), (37.4, 2.405, 2.4), (38.5, 2.338, 4.1), (39.4, 2.285, 3.8).

Solid-state CP/MAS $^{13}$C NMR chemical shifts (δ, in ppm) 13.289, 30.148, 43.636, 41.037, 52.164, 54.139, 46.605, 67.082, 174.406.

ATR-FT-IR absorption peaks (cm$^{-1}$): 673, 724, 774, 808, 826, 890, 944, 984, 1012, 1026, 1070, 1110, 1144, 1193, 1278, 1290, 1352, 1369, 1388, 1426, 1438, 1467, 1681, 2685, 2790, 2841, 2888, 2920, 2940, 2974, 3021, 3159, 3424.

DSC: endotherms at 105.6° C. (onset 104.4° C.), 134.7° C. (onset 133.4° C.) with a very broad trace at 75-95° C.

Figure 3B:
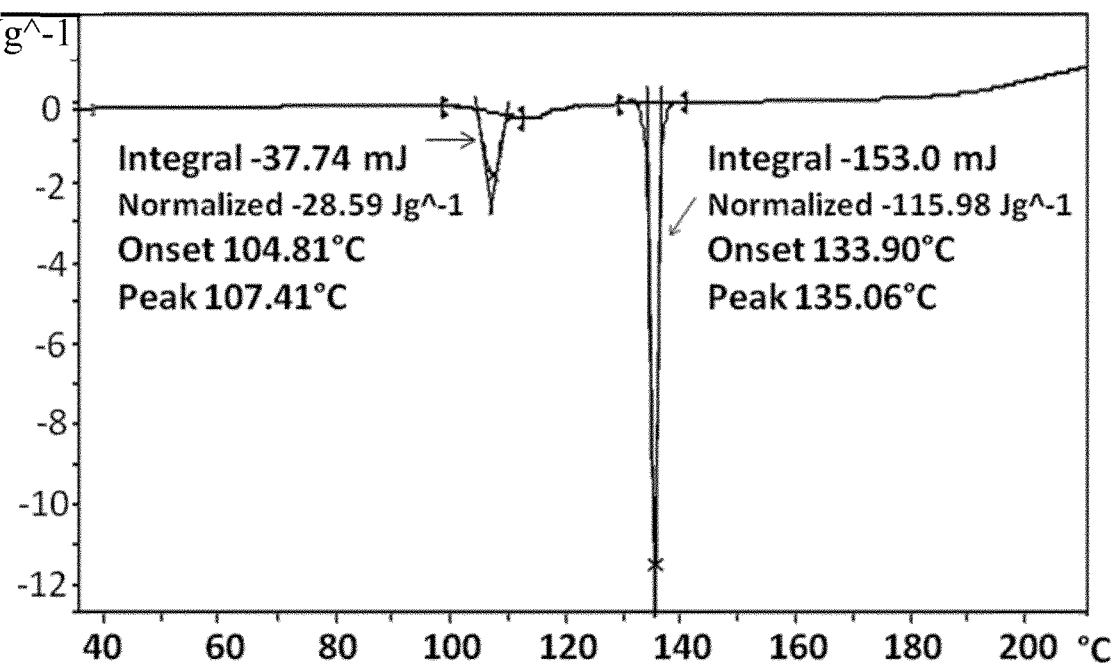

The TGA of this polymorphs showed a 5.2% weight loss when heated to a temperature up to about 120° C. which indicates less than a stoichiometric percentage of water required for a full monohydrate of Compound A. This form is defined as Form I with trace amounts of Form III because of characteristic peaks in DSC, XRPD, CP/MAS $^{13}$C NMR and ATR-FT-IR.

b) Form I can be obtained by slow evaporation at 50° C. of Compound A dissolved in water. The XRPD shows that the compound is crystalline, DSC shows only the characteristic endotherms of Form I at 107.4° C. (onset 104.8° C.) and 133.9° C. (onset 133.9° C.) (FIG. 3B).

Example 3: Crystalline Form I Compound A

To Compound A (1.0 g) was added isopropanol (3.5 ml), and the mixture was heated to dissolve the compound. The clear solution was cooled at room temperature overnight. Solid material which appeared to the naked eye to be crystalline formed in the solution. This material was collected by filtration and dried at room temperature under vacuum to give 0.5 g of solid Compound A.

Solid-state CP/MAS $^{13}$C NMR of the crystalline material yielded a spectrum having the following chemical shifts ($\delta_c$ in ppm, unrounded): 13.423, 30.301, 43.729, 41.122, 52.289, 54.237, 46.739, 67.222, 174.457.

ATR-FT-IR yielded a spectrum having the following absorption peaks (cm$^{-1}$, unrounded): 725, 775, 809, 827, 890, 945, 985, 1012, 1027, 1071, 1111, 1144, 1195, 1278, 1292, 1353, 1371, 1389, 1427, 1438, 1468, 1672, 2845, 3021, 3158, 3427.

This form is defined as Form I because of characteristic peaks in CP/MAS $^{13}$C NMR & ATR-FT-IR.

Example 4: Crystalline Form I Compound A

To Compound A (0.18 g) was added tetrahydrofuran (THF, 0.5 ml), and the mixture was heated to dissolve the compound. The clear solution was cooled at room temperature overnight. Solid material which appeared to the naked eye to be crystalline formed in the solution. This material was collected by filtration and dried at room temperature under vacuum to give solid Compound A.

Solid-state CP/MAS $^{13}$C NMR of the crystalline material yielded a spectrum having the following chemical shifts ($\delta_c$ in ppm, unrounded): 13.355, 30.227, 43.679, 41.090, 52.225, 54.170, 46.678, 67.153, 174.525.

ATR-FT-IR yielded a spectrum having the following absorption peaks (cm$^{-1}$, unrounded): 674, 726, 775, 809, 827, 985, 1027, 1071, 1111, 1144, 1195, 1278, 1292, 1353, 1371, 1388, 1426, 1438, 1468, 1676, 2791, 2850, 2920, 2940, 2974, 3023, 3159, 3430.

This form is defined as Form I because of characteristic peaks in CP/MAS $^{13}$C NMR & ATR-FT-IR.

Example 5: Crystalline Form I Compound A

To Compound A (0.11 g) was added ethanol (0.5 ml), and the mixture was heated to dissolve the compound. The clear solution was cooled at room temperature overnight. Solid material which appeared to the naked eye to be crystalline formed in the solution. This material was collected by filtration and dried at room temperature under vacuum to give solid Compound A.

Solid-state CP/MAS $^{13}$C NMR of the crystalline material yielded a spectrum having the following chemical shifts ($\delta_c$ in ppm, unrounded): 13.304, 30.191, 43.674, 40.999, 52.180, 54.138, 46.637, 67.100, 174.426.

ATR-FT-IR yielded a spectrum having the following absorption peaks (cm$^{-1}$, unrounded): 673, 724, 774, 808, 826, 985, 1027, 1046, 1070, 1110, 1278, 1291, 1353, 1370, 1388, 1426, 1438, 1467, 1669, 2790, 2842, 2887, 2920, 2940, 2974, 3022, 3161, 3426.

This form is defined as Form I because of characteristic peaks in CP/MAS $^{13}$C NMR & ATR-FT-IR.

Example 6: Crystalline Form I Compound A

To Compound A (0.11 g) was added tert-butyl methyl ether (1.3 ml), and the mixture was heated to dissolve the compound. The clear solution was cooled at room temperature overnight. Solid material which appeared to the naked eye to be crystalline formed in the solution. This material was collected by filtration and dried at room temperature under vacuum to give solid Compound A.

Solid-state CP/MAS $^{13}$C NMR of the crystalline material yielded a spectrum having the following chemical shifts ($\delta_c$ in ppm, unrounded): 13.134, 30.049, 43.479, 40.789, 53.979, 51.999, 46.448, 66.927, 174.217.

ATR-FT-IR yielded a spectrum having the following absorption peaks (cm$^{-1}$, unrounded): 725, 775, 809, 827, 985, 1027, 1071, 1111, 1144, 1195, 1278, 1292, 1353, 1371, 1388, 1427, 1438, 1468, 1670, 2790, 2842, 2974, 3021, 3157, 3430.

This form is defined as Form I because of characteristic peaks in CP/MAS $^{13}$C NMR & ATR-FT-IR.

Figure 7A:
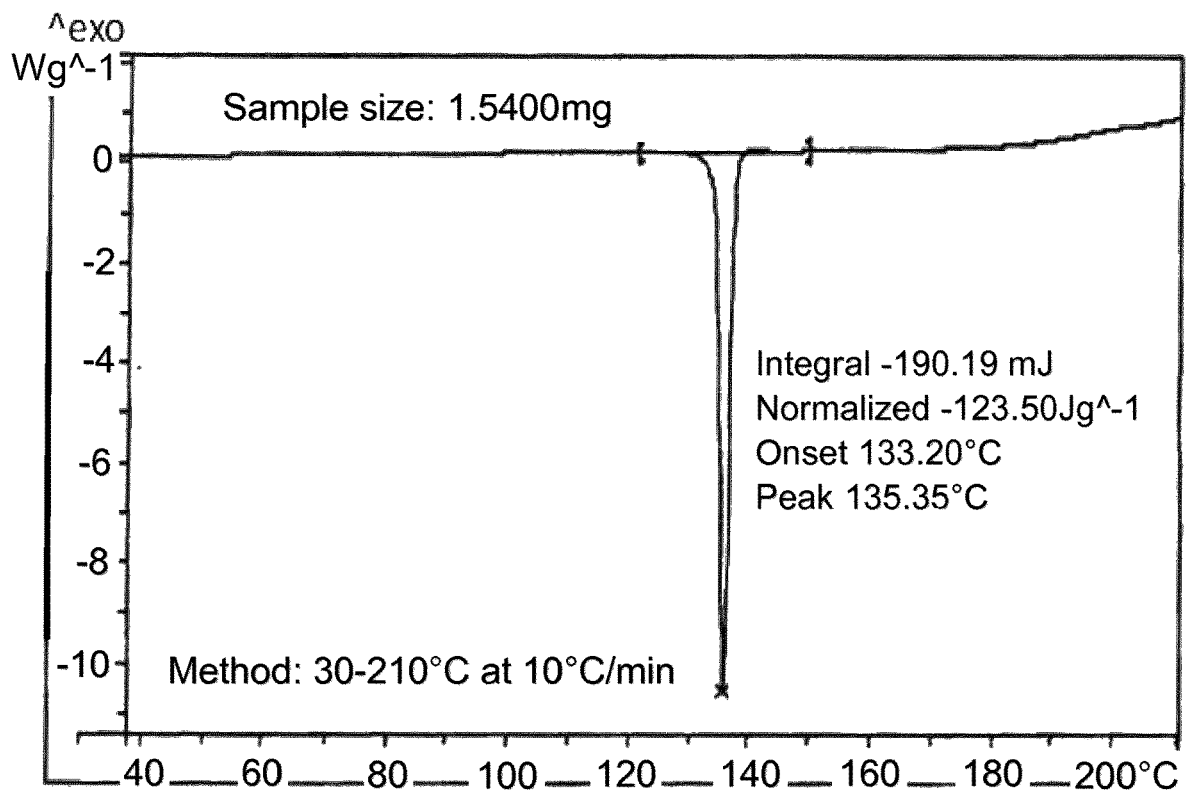
FIG. 7 presents DSC curves for the anhydrous crystalline Form II of Compound A: A) re-crystallized from acetone; B) the cGMP API. The DSC for A) and B) indicates only one endothermic peak at about 135.35° C. and 134.29° C., respectively.
Figure 7B:
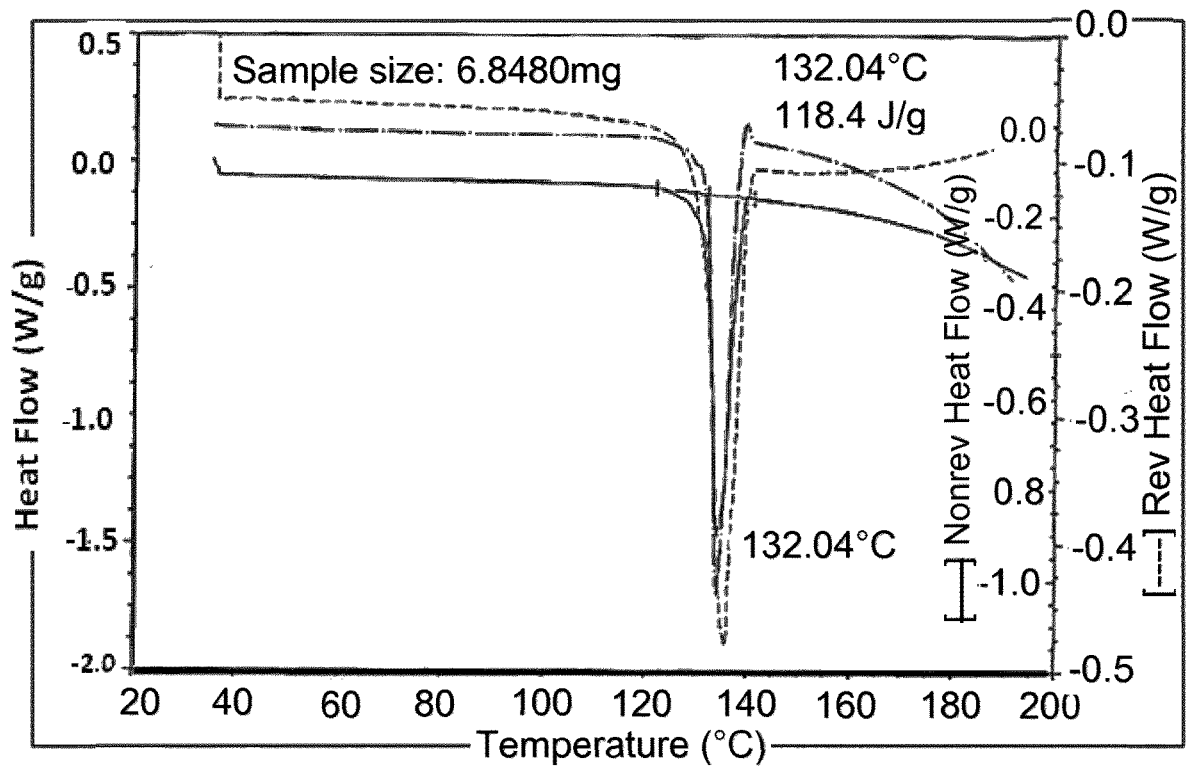
Figure 8A:
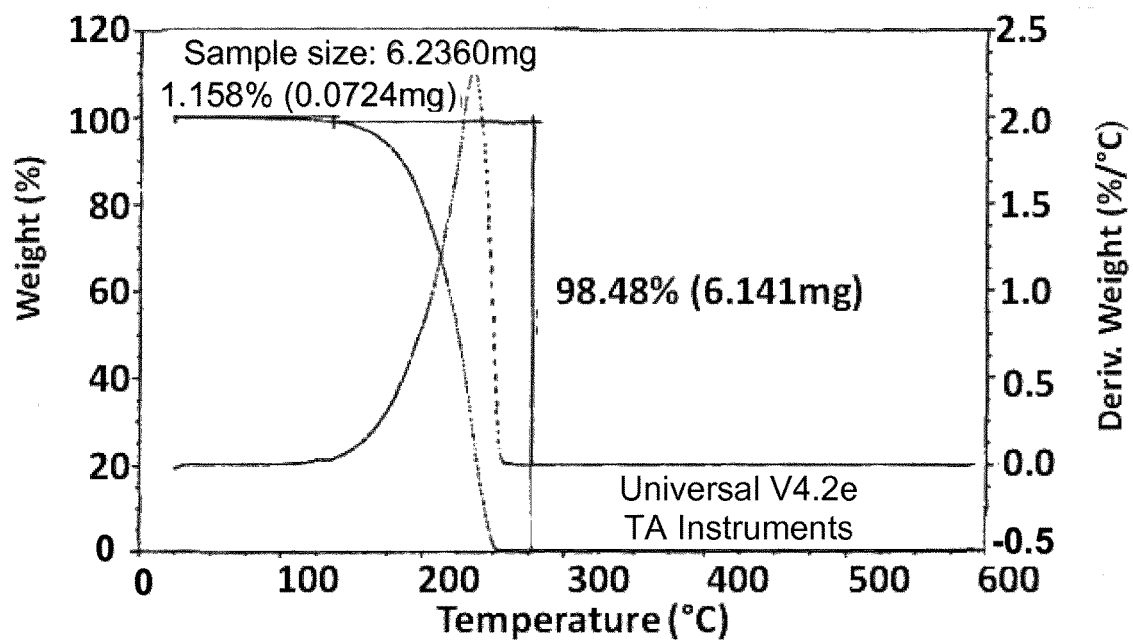
FIG. 8 presents the result of TGA for the anhydrous crystalline Form II of Compound A. A) re-crystallized from acetone (the TGA showed no significant weight loss up before 110° C.); B) the API (the TGA showed 0.73% weight loss at 115° C.).
Figure 8B:
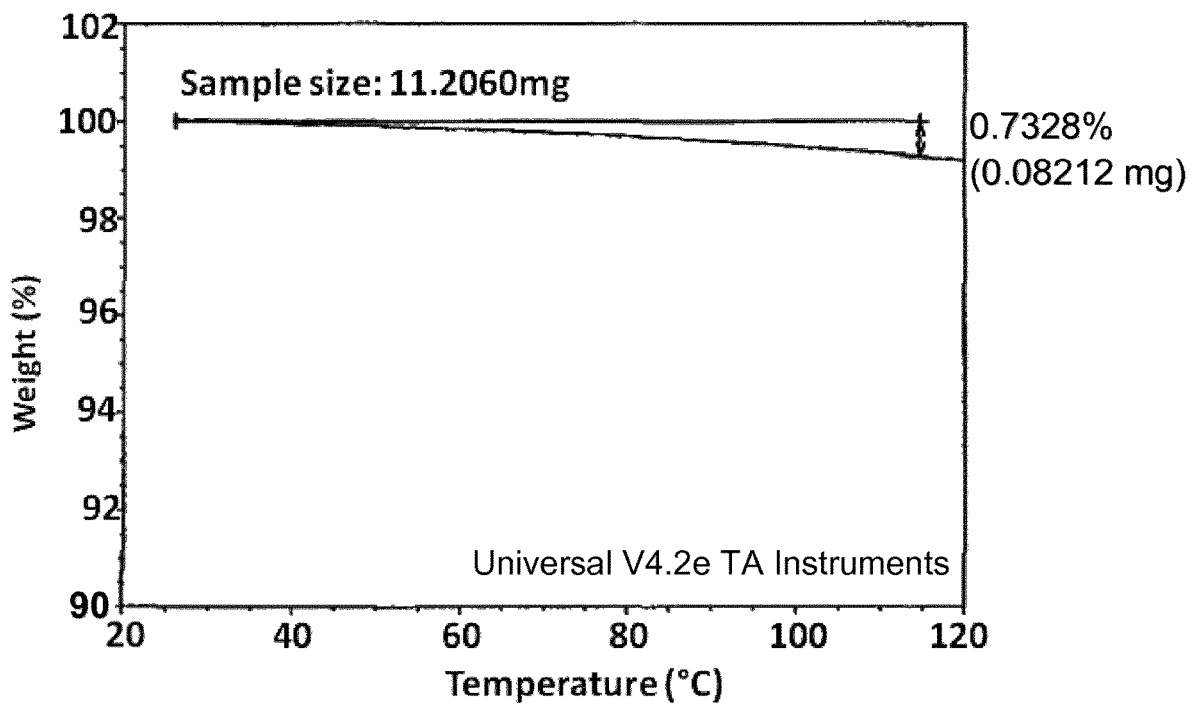

Example 7: Crystalline Form II Compound A; the API a) Pure Compound A Crystalline Form II can be formed by re-crystallization from acetone (FIGS. 6-8). The XRPD of Form II is shown in FIG. 6 and differs from the XRPD of Form I and Form III (FIGS. 1 and 2). DSC showed only one endothermic peak at 135.35° C. (onset 134.2° C.; FIG. 7A).

b) Pure crystalline Form II was also prepared as a cGMP compound in kgs quantities and used as the API in preclinical and clinical studies. This API is crystalline as shown by XRPD in FIG. 6B and Table 1. The DSC of this API showed an endothermic peak at 134.29° C. (FIG. 7B). TGA for the anhydrous crystalline Form II of Compound A showed no significant weight loss up before 110° C. (FIG. 8). Further information on Form II is described in Examples 25 and 26.

TABLE 1

X-ray powder diffraction of Form II: Listings of 2theta, d spacing, relative intensity, full width at half maximum (FWHM), peak counts and integrated peak count for each of the detected peaks

| | | | # Strongest 3 peaks | | | | |
|---|---|---|---|---|---|---|---|
| no. | peak no. | 2Theta (deg) | d (A) | I/II | FWHM (deg) | Intensity (Counts) | Integrated (Counts) |
| 1 | 9 | 19.7767 | 4.48556 | 100 | 0.12710 | 6060 | 46562 |
| 2 | 1 | 9.8897 | 8.93652 | 82 | 0.11770 | 4979 | 35872 |
| 3 | 4 | 11.9300 | 7.41237 | 78 | 0.12940 | 4715 | 31676 |

| | | # Peak Data List | | | | |
|---|---|---|---|---|---|---|
| peak no. | 2Theta (deg) | d (A) | I/II | FWHM (deg) | Intensity (Counts) | Integrated (Counts) |
| 1 | 9.8897 | 8.93652 | 82 | 0.11770 | 4979 | 35872 |
| 2 | 10.7921 | 8.19122 | 30 | 0.11250 | 1795 | 12577 |
| 3 | 11.7600 | 7.51913 | 31 | 0.13860 | 1884 | 19320 |
| 4 | 11.9300 | 7.41237 | 78 | 0.12940 | 4715 | 31676 |
| 5 | 14.7625 | 5.99590 | 16 | 0.17120 | 966 | 10620 |
| 6 | 16.1991 | 5.46725 | 7 | 0.22540 | 401 | 5035 |
| 7 | 18.2000 | 4.87044 | 33 | 0.19420 | 2024 | 22608 |
| 8 | 18.4592 | 4.80263 | 77 | 0.16100 | 4695 | 40314 |
| 9 | 19.7767 | 4.48556 | 100 | 0.12710 | 6060 | 46562 |
| 10 | 21.2729 | 4.17333 | 4 | 0.16250 | 255 | 2404 |
| 11 | 21.5904 | 4.11267 | 4 | 0.15390 | 235 | 2048 |
| 12 | 22.1000 | 4.01898 | 1 | 0.11480 | 80 | 428 |
| 13 | 22.3798 | 3.96936 | 12 | 0.14840 | 718 | 6890 |
| 14 | 22.7003 | 3.91404 | 27 | 0.14230 | 1633 | 12995 |
| 15 | 23.9292 | 3.71574 | 23 | 0.13200 | 1365 | 10904 |
| 16 | 24.2575 | 3.66619 | 2 | 0.12910 | 98 | 600 |
| 17 | 24.8370 | 3.58195 | 6 | 0.20850 | 352 | 6312 |
| 18 | 25.2800 | 3.52017 | 2 | 0.11260 | 93 | 485 |
| 19 | 26.1027 | 3.41106 | 3 | 0.14610 | 175 | 1203 |
| 20 | 26.4361 | 3.36879 | 7 | 0.21560 | 420 | 7835 |
| 21 | 26.9035 | 3.31132 | 2 | 0.11100 | 97 | 505 |
| 22 | 27.2103 | 3.27467 | 1 | 0.12060 | 57 | 339 |
| 23 | 28.3424 | 3.14639 | 1 | 0.10860 | 61 | 313 |
| 24 | 28.7210 | 3.10577 | 4 | 0.16110 | 241 | 2421 |
| 25 | 29.1497 | 3.06106 | 7 | 0.14910 | 433 | 4077 |
| 26 | 29.4845 | 3.02706 | 3 | 0.17520 | 154 | 1267 |
| 27 | 29.6800 | 3.00757 | 9 | 0.14740 | 561 | 5049 |
| 28 | 29.8400 | 2.99180 | 7 | 0.10460 | 441 | 2992 |

TABLE 1-continued

X-ray powder diffraction of Form II: Listings of 2theta, d spacing,
relative intensity, full width at half maximum (FWHM), peak counts
and integrated peak count for each of the detected peaks

| | | | | | | |
|---|---|---|---|---|---|---|
| 29 | 31.2386 | 2.86097 | 1 | 0.12450 | 70 | 414 |
| 30 | 31.8919 | 2.80384 | 6 | 0.22250 | 387 | 5169 |
| 31 | 32.6400 | 2.74126 | 5 | 0.16580 | 286 | 3185 |
| 32 | 32.9600 | 2.71538 | 20 | 0.22340 | 1226 | 11010 |
| 33 | 33.1000 | 2.70421 | 22 | 0.13580 | 1322 | 8576 |
| 34 | 33.3600 | 2.68373 | 6 | 0.13740 | 383 | 3789 |
| 35 | 33.9000 | 2.64220 | 1 | 0.16840 | 81 | 639 |
| 36 | 34.3800 | 2.60640 | 1 | 0.07660 | 47 | 173 |
| 37 | 34.6020 | 2.59019 | 1 | 0.39170 | 53 | 1011 |
| 38 | 34.7600 | 2.57878 | 2 | 0.18600 | 95 | 867 |
| 39 | 34.9400 | 2.56590 | 4 | 0.16800 | 271 | 3999 |
| 40 | 36.2200 | 2.47811 | 6 | 0.14000 | 360 | 2580 |
| 41 | 36.4419 | 2.46352 | 4 | 0.21520 | 252 | 2910 |
| 42 | 36.8052 | 2.44004 | 9 | 0.16820 | 530 | 4818 |
| 43 | 37.4600 | 2.39887 | 2 | 0.07620 | 119 | 431 |
| 44 | 38.2448 | 2.35143 | 1 | 0.14780 | 83 | 597 |
| 45 | 38.4896 | 2.33704 | 2 | 0.17750 | 106 | 891 |
| 46 | 41.7800 | 2.16028 | 2 | 0.07640 | 118 | 426 |
| 47 | 43.3200 | 2.08698 | 2 | 0.13640 | 100 | 644 |
| 48 | 43.9467 | 2.05866 | 1 | 0.14990 | 68 | 477 |

| # Measurement Condition X-ray tube | | Scanning | |
|---|---|---|---|
| target | Cu | drive axis | Theta-2Theta |
| voltage | 40.0 (kV) | scanrange | 4.0000-45.0000 (deg) |
| current | 35.0 (mA) | scan mode | Continuous Scan |
| | | scan speed | 2.0000 (deg/mim) |
| | | sampling pitch | 0.0200 (deg) |
| | | presettime | 0.60 (sec) |
| | | BetaAxis RotationSpeed | 60:00 (rpm) |

| Slits | |
|---|---|
| divergence slit | 1.00 (deg) |
| scatter slit | 1.00 (deg) |
| receiving slit | 0.30 (mm) | c) Pure anhydrous crystalline Form II can be obtained from a saturated solutions of Compound A prepared by adding Compound A to acetone at 30° C. to 50° C. These were quench cooled in an acetone/ice bath to induce precipitation. The solid formed was isolated and characterized by XRPD. The XRPD showed the characteristic peaks of Form II.

d) Pure anhydrous crystalline Form II can be obtained from a saturated solution of Compound A in acetone prepared at 30° C. and 50° C. that was cooled slowly in a programmed circulation bath. The formed slurry was then heated to 50° C. over 2 hours and then cooled to 25° C. over 2 hours. This process was repeated overnight and the solid was isolated for further analysis by XRPD. The XRPD showed the characteristic peaks of Form II.

Example 8: Crystalline Form II Compound A a) To Compound A (1.05 g) was added acetonitrile (9 ml), and the mixture was heated to dissolve the compound. The clear solution was cooled at room temperature overnight. Solid material which appeared to the naked eye to be crystalline formed in the solution. This material was collected by filtration and dried at room temperature under vacuum to give 0.71 g of solid Compound A. X-ray powder diffraction, which yielded the following 2-theta values, d-spacings and relative intensities, confirmed that the material was crystalline:

| 2θ (±0.1) | d (Å, unrounded) | I/I₀ |
|---|---|---|
| 9.9 | 8.894 | 100.0 |
| 10.8 | 8.16 | 12.7 |
| 11.8 | 7.482 | 33.0 |
| 12.2 | 7.225 | 11.3 |
| 14.8 | 5.971 | 24.0 |
| 15.5 | 5.729 | 2.9 |
| 16.2 | 5.458 | 15.0 |
| 17.3 | 5.120 | 18.9 |
| 18.2 | 4.861 | 59.4 |
| 18.5 | 4.792 | 63.7 |
| 19.8 | 4.476 | 81.4 |
| 21.3 | 4.164 | 9.5 |
| 21.6 | 4.107 | 11.6 |
| 22.4 | 3.960 | 12.2 |
| 22.7 | 3.909 | 19.0 |
| 24.0 | 3.704 | 5.4 |
| 24.7 | 3.605 | 8.2 |
| 26.3 | 3.39 | 8.4 |
| 28.8 | 3.100 | 6.9 |
| 29.2 | 3.058 | 6.3 |
| 29.7 | 3.002 | 9.1 |
| 31.3 | 2.859 | 3.7 |
| 32.0 | 2.801 | 7.7 |
| 32.9 | 2.717 | 7.5 |
| 34.0 | 2.637 | 2.8 |
| 35.0 | 2.563 | 5.2 |
| 36.5 | 2.460 | 6.6 |
| 36.9 | 2.436 | 9.5 |
| 37.4 | 2.402 | 2.1 |
| 38.3 | 2.348 | 3.3 |

Solid-state CP/MAS $^{13}$C NMR of the crystalline material yielded a spectrum having the following chemical shifts ($\delta_c$ in ppm, unrounded): 15.371, 14.834, 28.871, 26.010, 52.326, 49.327, 43.582, 39.487, 38.761, 45.773, 44.974, 65.289, 64.013, 175.005.

ATR-FT-IR yielded a spectrum having the following absorption peaks (cm$^{-1}$, unrounded): 729, 773, 822, 906, 944, 989, 1027, 1065, 1108, 1147, 1194, 1279, 1294, 1340, 1362, 1425, 1447, 1464, 1667, 2792, 2850, 2869, 2901, 2940, 2951, 3006, 3160, 3428.

DSC showed endotherms at 50-77° C. (very small and broad possibly due to the presence of trace amounts of Form III), 105.2° C. (onset at 104.5° C.; very small, possibly due to the presence of trace amounts of Form I) and 134.8° C. (onset 133.4° C.).

b) Pure anhydrous crystalline Form II can be obtained in dry acetonitrile (re Example 26 and FIG. 11), c) Pure anhydrous crystalline Form II can be obtained from a slurry of the monohydrate Form I and III in acetonitrile (re Example 22).

d) Pure anhydrous crystalline Form II can be obtained from a saturated solution of Compound A prepared by adding Compound A to acetonitrile at 30° C. to 50° C. and this was quench cooled in an acetone/ice bath to induce precipitation. The solid formed was isolated and characterized by XRPD and showed the characteristic peaks of Form II.

e) Pure anhydrous crystalline Form II can be obtained from a saturated solution of Compound A in acetonitrile prepared at 30° C. and 50° C. that was cooled slowly in a programmed circulation bath. The formed slurry was then heated to 50° C. over 2 hours and then cooled to 25° C. over 2 hours. This process was repeated overnight and the solid was isolated for further analysis by XRPD that showed the characteristic peaks of Form II.

Example 9: Crystalline Form II Compound A a) To Compound A (1.25 g) was added hexane (100 ml), and the mixture was heated to dissolve the compound. The clear solution was cooled at room temperature overnight. Solid material which appeared to the naked eye to be crystalline formed in the solution. This material was collected by filtration and dried at room temperature under vacuum to give 1.06 g of solid Compound A. X-ray powder diffraction confirmed that the material was crystalline Form II with trace amounts of Form I. This Form is defined a Form II because of characteristic peaks in CP/MAS $^{13}$C NMR & ATR-FT-IR:

Solid-state CP/MAS $^{13}$C NMR of the crystalline material yielded a spectrum having the following chemical shifts ($\delta_c$ in ppm, unrounded): 15.385, 14.829, 28.998, 25.945, 52.293, 49.345, 43.595, 39.504, 45.791, 45.014, 65.441, 64.086, 174.963 (re Table 6).

ATR-FT-IR yielded a spectrum having the following absorption peaks (cm$^{-1}$, unrounded): 730, 773, 805, 820, 854, 905, 944*, 988*, 1027*, 1064, 1108*, 1148, 1193, 1278, 1294, 1339, 1362, 1424, 1446, 1458, 1664, 2685, 2723, 2771, 2850, 2868, 2901, 2940, 2951, 3005 (*These peaks due to trace amounts of Form I in Form II of Compound A).

b) Pure anhydrous crystalline Form II can be obtained by phase equilibration of a suspension Compound A in hexane at 50° C.±1. After equilibration for 24 hours, the supernatant was filtered and the solid was collected and analyzed by XRPD. X-ray powder diffraction confirmed that the material was crystalline and yielded the characteristic peaks of 2-theta values, d-spacings and relative intensities of Form II.

Example 10: Crystalline Form II Compound A

To Compound A (1.48 g) was added dioxane (4 ml), and the mixture was heated to dissolve the compound. The clear solution was cooled at room temperature overnight. Solid material which appeared to the naked eye to be crystalline formed in the solution. This material was collected by filtration and dried at room temperature under vacuum to give 0.77 g of solid Compound A. The X-ray powder diffraction, which yielded the following 2-theta values, d-spacings and relative intensities, confirmed that the material was crystalline:

| 2θ (±0.1) | d (Å, unrounded) | I/I$_0$ |
|---|---|---|
| 9.9 | 8.906 | 100 |
| 10.8 | 8.181 | 18.1 |
| 11.8 | 7.498 | 27.7 |
| 12.2 | 7.238 | 5.4 |
| 14.8 | 5.973 | 16.2 |
| 15.5 | 5.731 | 1.7 |
| 16.2 | 5.458 | 10.4 |
| 17.31 | 5.124 | 10.5 |
| 18.2 | 4.866 | 38 |
| 18.5 | 4.801 | 36.2 |
| 19.8 | 4.479 | 72.7 |
| 21.3 | 4.169 | 5.6 |
| 21.6 | 4.106 | 6.4 |
| 22.4 | 3.968 | 9.3 |
| 22.7 | 3.908 | 14.4 |
| 24.0 | 3.712 | 5.3 |
| 24.9 | 3.578 | 5 |
| 26.4 | 3.38 | 4.7 |
| 28.8 | 3.105 | 4 |
| 29.2 | 3.06 | 4.4 |
| 29.8 | 2.993 | 5.4 |
| 31.9 | 2.805 | 4.8 |
| 32.9 | 2.718 | 9.4 |
| 35.0 | 2.563 | 3.1 |
| 36.8 | 2.44 | 4.1 |
| 38.5 | 2.337 | 1.8 |

As shown in FIG. 9 (Form II) solid-state CP/MAS $^{13}$C NMR of the crystalline material yielded a spectrum having the following chemical shifts ($\delta_c$ in ppm, unrounded): 15.359, 14.788, 28.926, 25.956, 52.311, 49.342, 43.462, 39.543, 45.806, 44.960, 65.557, 63.967, 174.965.

As shown in FIG. 10 (Form II), ATR-FT-IR yielded a spectrum having the following absorption peaks (cm$^{-1}$, unrounded): 729, 773, 822, 906, 944, 988, 1027, 1065, 1109, 1148, 1194, 1279, 1294, 1339, 1362, 1426, 1447, 1471, 1671, 2793, 2850, 2869, 2901, 2941, 2951, 3012, 3159, 3432.

DSC showed endotherms at 56-66° C. (very small, probably residue of solvent or trace amount of Form III) and 134.9° C. (onset at 133.7° C.).

This form is also defined as Form II because of characteristic peaks in CP/MAS $^{13}$C NMR and ATR-FT-IR.

Example 11: Crystalline Form II Compound A

To Compound A (0.19 g) was added diethylether (7 ml), and the mixture was heated to dissolve the compound. The clear solution was cooled at room temperature overnight. Solid material which appeared to the naked eye to be crystalline formed in the solution. This material was collected by filtration and dried at room temperature under vacuum to give solid Compound A.

Solid-state CP/MAS $^{13}$C NMR of the crystalline material yielded a spectrum having the following chemical shifts ($\delta_c$ in ppm, unrounded): 15.206, 14.629, 13.102*, 28.814, 25.747, 52.167, 49.182, 43.326, 39.323, 38.529, 45.610, 44.756, 66.827*, 65.310, 63.845, 174.863. (*The peaks at 13.102 and 66.827 may be due to the presence of a trace amount of Form I).

ATR-FT-IR yielded a spectrum having the following absorption peaks (cm$^{-1}$, unrounded): 728, 773, 822, 944, 987, 1027, 1065, 1108, 1147, 1278, 1293, 1339, 1362, 1425, 1445, 1459, 1664, 2787, 2847, 2869, 2902, 2921, 2951, 3006, 3147.

This form is defined as Form II because of characteristic peaks in CP/MAS $^{13}$C NMR and ATR-FT-IR.

Example 12: Crystalline Form II Compound A

Pure anhydrous crystalline Form II can be obtained from a saturated solution of Compound A in hexane prepared at 30° C. and 50° C. that was cooled slowly in a programmed circulation bath. The formed slurry was then heated to 50° C. over 2 hours and then cooled to 25° C. over 2 hours. This process was repeated overnight and the solid was isolated for further analysis by XRPD and showed the characteristic peaks of Form II.

Example 13: Crystalline Form II Compound A

To Compound A (0.10 g) was added cyclohexane (5 ml), and the mixture was heated to dissolve the compound. The clear solution was cooled at room temperature overnight. Solid material which appeared to the naked eye to be crystalline formed in the solution. This material was collected by filtration and dried at room temperature under vacuum to give solid Compound A.

Solid-state CP/MAS $^{13}$C NMR of the crystalline material yielded a spectrum having the following chemical shifts ($\delta_c$ in ppm, unrounded): 15.356, 14.775, 29.061, 25.940, 52.340, 49.360, 43.368, 39.70438.721, 45.819, 44.950, 65.646, 64.006, 175.093.

ATR-FT-IR yielded a spectrum having the following absorption peaks (cm$^{-1}$, unrounded): 668, 682, 707, 749, 774, 809, 824, 862, 945, 988, 1027, 1065, 1110, 1146, 1195, 1279, 1294, 1351, 1448, 1468, 1676, 2735, 2792, 2816, 2827, 2851, 2900, 2922, 2941.

This form is defined as Form II because of characteristic peaks in CP/MAS $^{13}$C NMR and ATR-FT-IR.

Example 14: Crystalline Polymorph Form III Compound A

Crystalline Form III Compound A can be produced from a re-slurry of Compound A in de-ionized water and filtration. The X-ray powder diffraction, confirmed that the material was crystalline (re FIG. 2).

Initial experiments attempted to identify a solvent to use to re-crystallize Compound A for large scale cGMP crystallization of the API showed that a variety of solvents could be used to produce the API with good recovery. However, many of these solvents (inter alia, ethyl acetate/heptane, ethanol, tetrahydrofuran, toluene, isobutyl acetate, methyl isobutyl ketone) were not suitable for scaling due to the fact that the final product, long needle-like crystals, stuck to the sides of the flask. These sticky solids required manual scraping to remove them. Acetone emerged as the one solvent that produced a white material with a minimum loss of solids to the sides of the flask. In this case re-crystallization from acetone produced the crystal Form II (FIGS. 6-8). Hydration of the final product was the last requirement needed to produce Form III. Experimentation showed that Compound A could pick up about 1 molar equivalent of water in an aqueous acetone solution, if stirred for approximately 0.5 h. Thus crystalline Form III Compound A was produced in large kg quantities as cGMP API by adding 1.3 moles of de-ionized water to the solution of Compound A in acetone. Since Compound A (Form II) could easily pick up water, a drying method need to be developed which would remove acetone without removing water. Oven drying experiments proved to be an impractical way of doing this. Drying the material overnight under full house vacuum at 40° C. almost completely removes all the water as shown by Karl Fisher analysis. Even at 20-25° C., under full house vacuum, water could be removed from the molecule. It was later discovered that if the relative humidity fell below 10% water would be removed. Conversely, if the relative humidity were above 60% the product would regain that water, eventually becoming a full hydrate. From this data, two methods of hydration were developed. Both methods first involve forming the hydrate by adding 1.3 moles of water to the homogeneous crystallization solution; filtering the hydrated material; analyzing by Karl Fisher; and drying that material on the filter with vacuum and a nitrogen stream. This removes acetone without dehydrating the molecule. The other method would have involved removing the acetone using a vacuum oven at ambient temperature, then re-hydrating the material by increasing the relative humidity in the oven to between 60-90%. 15.11 Acetone, 1 kg of Compound A were charged to a vessel and the solution was brought to an atmospheric reflux. The solution is then held at reflux to ensure complete dissolution of the solids. The solution is then cooled to between 35-45° C. and passed through an in-line filter to remove any particulates. Now the solution is heated and atmospherically distilled down to between 7.4-7.6 l. 0.1 l deionized water is added and the solution is cooled to −5 to −10° C. over 3-4 hours. The solution is then held at −5 to −10° C. for not less than 1 hour. An in-process control is taken at this point, the filtered solids are analyzed for water content, if the Karl Fisher analysis is above 7.5% the process is moved forward. The solids are then filtered and dried on the filter with vacuum and N$_2$ flow for a minimum of 4 hours. The crystallization yields about 1.0 kg of Compound A monohydrate, Form III as the API (~93% yield); (re FIG. 4B, FIG. 5, and Example 24).

X-ray powder diffraction confirmed that the material so obtained was crystalline (Table 2 and FIG. 2):

TABLE 2

X-ray powder diffraction of Form III: Listings of 2theta, d spacing, relative intensity, full width at half maximum (FWHM), peak counts and integrated peak count for each of the detected peaks

| # Strongest 3 Peaks | | | | | | |
|---|---|---|---|---|---|---|
| no. | peak no. | 2Theta (deg) | D (A) | I/I1 | FWHM (deg) | Intensity (Counts) | Integrated (Counts) |
| 1 | 6 | 17.51 | 5.06 | 100 | 0.1821 | 8489 | 75983 |
| 2 | 3 | 12.25 | 7.21 | 33 | 0.1710 | 2810 | 29889 |
| 3 | 5 | 17.26 | 513 | 28 | 0.1622 | 2419 | 31649 |

| # Peak List | | | | | |
|---|---|---|---|---|---|
| peak no. | 2Theta (deg) | D (A) | I/I1 | FWHM (deg) | Intensity (Counts) | Integrated (Counts) |
| 1 | 8.80 | 10.03792 | 3 | 0.11770 | 4979 | 35872 |
| 2 | 9.67 | 9.13934 | 1 | 0.11250 | 1795 | 12577 |
| 3 | 12.25 | 7.21045 | 33 | 0.13860 | 1884 | 19320 |
| 4 | 15.62 | 5.65862 | 1 | 0.12940 | 4715 | 31676 |
| 5 | 17.26 | 5.13352 | 28 | 0.17120 | 966 | 10620 |
| 6 | 17.51 | 5.06193 | 100 | 0.22540 | 401 | 5035 |

TABLE 2-continued

X-ray powder diffraction of Form III: Listings of 2theta, d spacing, relative intensity, full width at half maximum (FWHM), peak counts and integrated peak count for each of the detected peaks

| | | | | | | |
|---|---|---|---|---|---|---|
| 7  | 17.80 | 4.97898 | 5  | 0.19420 | 2024 | 22608 |
| 8  | 19.28 | 4.59999 | 1  | 0.16100 | 4695 | 40314 |
| 9  | 19.89 | 4.46131 | 10 | 0.12710 | 6060 | 46562 |
| 10 | 21.64 | 4.10292 | 19 | 0.16250 | 255  | 2404  |
| 11 | 22.72 | 3.91069 | 1  | 0.15390 | 235  | 2048  |
| 12 | 23.08 | 3.85050 | 2  | 0.11480 | 80   | 428   |
| 13 | 23.53 | 3.77803 | 5  | 0.14840 | 718  | 6890  |
| 14 | 24.44 | 3.63922 | 5  | 0.14230 | 1633 | 12995 |
| 15 | 24.56 | 3.62171 | 6  | 0.13200 | 1365 | 10904 |
| 16 | 26.31 | 3.38435 | 12 | 0.12910 | 98   | 600   |
| 17 | 27.23 | 3.27210 | 1  | 0.20850 | 352  | 6312  |
| 18 | 28.80 | 3.09728 | 4  | 0.11260 | 93   | 485   |
| 19 | 30.22 | 2.95504 | 1  | 0.14610 | 175  | 1203  |
| 20 | 30.38 | 2.93848 | 2  | 0.21560 | 420  | 7835  |
| 21 | 31.27 | 2.85797 | 5  | 0.11100 | 97   | 505   |
| 22 | 31.62 | 2.82733 | 7  | 0.12060 | 57   | 339   |
| 23 | 31.76 | 2.81518 | 6  | 0.10860 | 61   | 313   |
| 24 | 32.06 | 2.78952 | 2  | 0.16110 | 241  | 2421  |
| 25 | 32.54 | 2.74976 | 1  | 0.14910 | 433  | 4077  |
| 26 | 32.78 | 2.72988 | 1  | 0.17520 | 154  | 1267  |
| 27 | 32.92 | 2.71859 | 1  | 0.14740 | 561  | 5049  |
| 28 | 34.03 | 2.63228 | 1  | 0.10460 | 441  | 2992  |
| 29 | 34.57 | 2.59259 | 3  | 0.12450 | 70   | 414   |
| 30 | 34.86 | 2.57168 | 2  | 0.22250 | 387  | 5169  |
| 31 | 35.05 | 2.55833 | 2  | 0.16580 | 286  | 3185  |
| 32 | 35.39 | 2.53399 | 8  | 0.22340 | 1226 | 11010 |
| 33 | 35.50 | 2.52670 | 4  | 0.13580 | 1322 | 8576  |
| 34 | 36.03 | 2.49088 | 2  | 0.13740 | 383  | 3789  |
| 35 | 36.50 | 2.45949 | 1  | 0.16840 | 81   | 639   |
| 36 | 37.11 | 2.42099 | 1  | 0.07660 | 47   | 173   |
| 37 | 37.36 | 2.40531 | 1  | 0.39170 | 53   | 1011  |
| 38 | 38.50 | 2.33632 | 2  | 0.18600 | 95   | 867   |
| 39 | 39.10 | 2.30208 | 1  | 0.16800 | 271  | 3999  |
| 40 | 39.50 | 2.27966 | 3  | 0.14000 | sso  | 2580  |
| 41 | 40.18 | 2.24253 | 2  | 0.21520 | 252  | 2910  |
| 42 | 41.30 | 2.18378 | 1  | 0.16820 | 530  | 4818  |
| 43 | 41.90 | 2.15414 | 1  | 0.07620 | 119  | 431   |
| 44 | 42.16 | 2.14147 | 1  | 0.14780 | 83   | 597   |
| 45 | 42.39 | 2.13069 | 1  | 0.17750 | 106  | 891   |
| 46 | 43.41 | 2.08284 | 1  | 0.07640 | 118  | 426   |
| 47 | 43.70 | 2.06971 | 1  | 0.13640 | 100  | 644   |
| 48 | 43.94 | 2.05880 | 2  | 0.14990 | 68   | 477   |

(Experimental details as for Table 1).

FIG. 4 presents differential scanning calorimetry (DSC) curves for a monohydrate crystalline form of Compound A (Form III); A) from a re-slurry in water. The DSC indicates two endothermic peaks, one at about 77.10° C. and the other at about 134.87° C.; and B) the cGMP active pharmaceutical ingredient (API), prepared by crystallization from acetone and 1.3 equivalent of water. The DSC indicates two endothermic peaks, one at about 61.18° C. and the other at about 133.75° C.

FIG. 5 presents the result of thermogravimetric analysis (TGA) for a monohydrate crystalline form of Compound A (Form III; the API). The TGA indicates a 7.8% weight loss when heated to a temperature up to about 110° C. Moisture by Karl Fischer analysis is 7.7% as expected from a stoichiometric monohydrate.

Example 15: Transformation of Form II to Form III

Figure 15A:
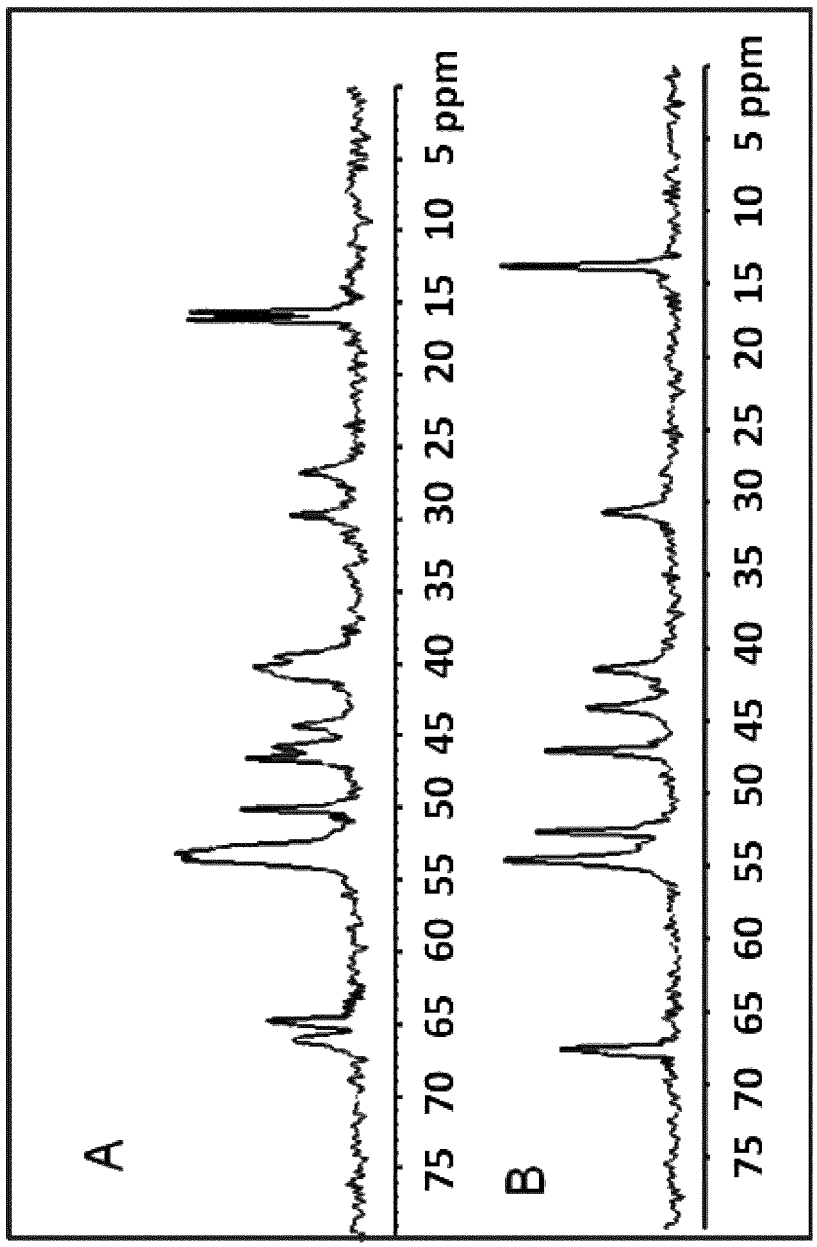
FIG. 15 presents transformation at 95% RH of Form II to Form III. A) CP/MAS $^{13}$C NMR solid state NMR. Compound A anhydrous crystal (A) dry; and (B) after storage for one week at room temperature at 95% RH. B) Compound A anhydrous crystal was completely converted to pure monohydrate crystal, Form III, as shown by CP/MAS $^{13}$C-solid state NMR, DSC and TGA.
Figure 15B:
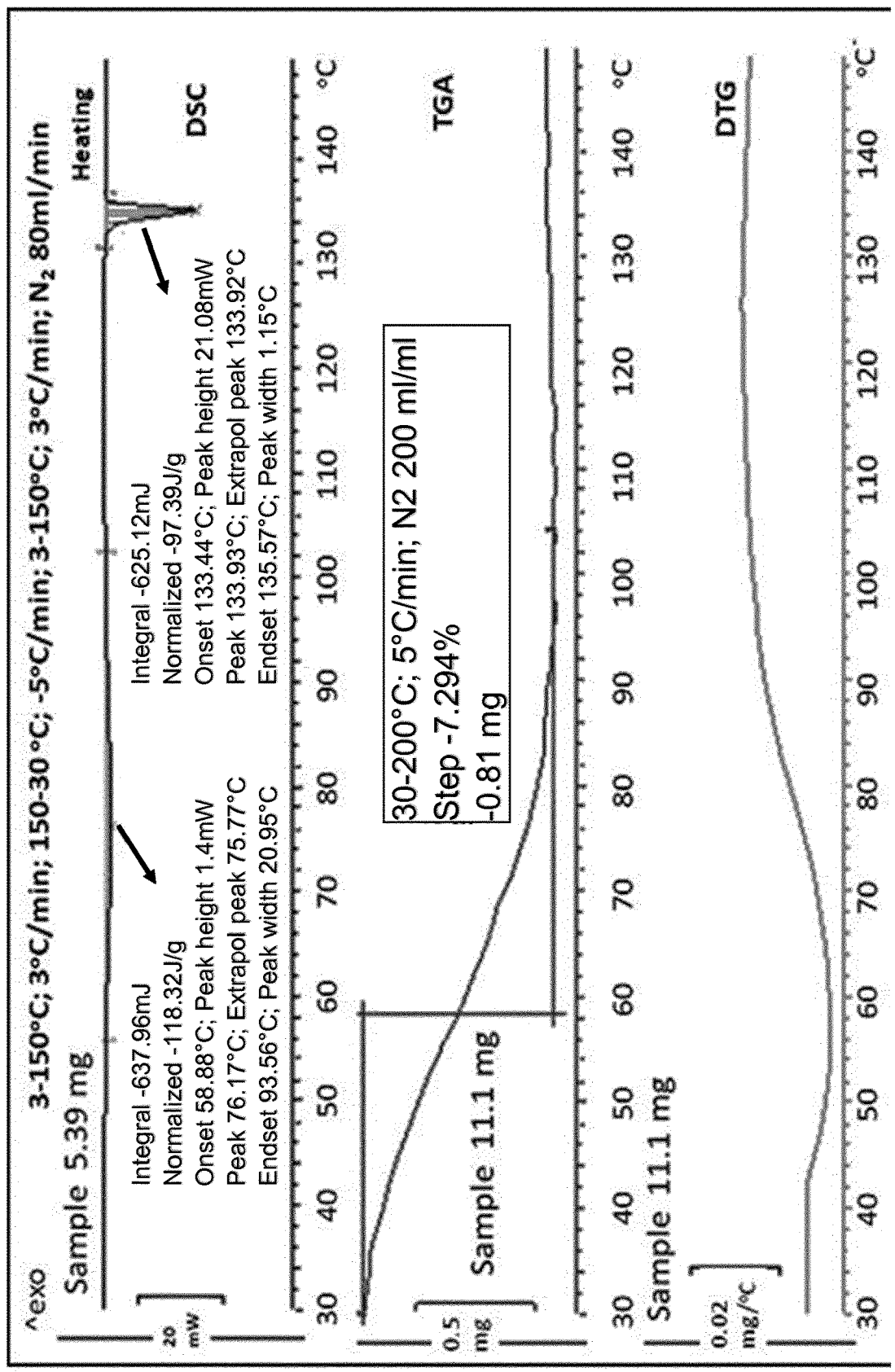

Compound A Crystalline Form II (0.4631 g; crystallized from acetonitrile) was placed in a desiccator at 95% relative humidity (saturated solution of $Na_2HPO_4$) at room temperature for one week (FIG. 15A). Analysis of the crystalline material by X-ray powder diffraction, ATR FT-IR, CP-MAS solid state $^{13}C$ NMR, DSC and TGA indicated that the material was neither crystalline Form I nor Form II Compound A, but Form III (re FIG. 15B). It will be appreciated that the X-ray powder diffraction, ATR FT-IR and $^{13}C$ NMR characteristics of Form III are similar to those of Form I. However, examination of the DSC showed endotherms at 58-94° C. (very broad) and 133.9° C. (onset 133.4° C.), and the TGA curve showed loss of 7.3% of weight between 58° C. and 94° C., indicating the presence of one molecule of water for each molecule of Compound A, which are both characteristic features of Form III (FIG. 15). Notably, such a continuous dehydration behavior with onset at relatively low temperature is common for channel-type hydrates as attributed also to Form III (re also Mirza et al., *AAPS Pharma Sci.* 5(2): 2003). X-ray powder diffraction confirmed that the material so obtained was crystalline:

| 2θ (±0.2) | d (Å, unrounded) | I/I₀ |
|---|---|---|
| 8.8  | 10.338 | 2.6  |
| 9.6  | 9.439  | 1.9  |
| 12.2 | 7.360  | 40.4 |
| 15.5 | 5.786  | 6.6  |
| 17.3.| 5.187  | 100.0|
| 17.5 | 5.091  | 61.5 |
| 19.3 | 4.645  | 2.3  |
| 19.9 | 4.512  | 26.2 |
| 21.6 | 4.147  | 40.1 |
| 22.8 | 3.944  | 4.0  |
| 23.1 | 3.895  | 5.9  |
| 23.5 | 3.815  | 4.2  |
| 24.5 | 3.673  | 12.5 |
| 26.3 | 3.414  | 21.8 |
| 28.8 | 3.121  | 8.4  |
| 30.3 | 2.967  | 4.5  |
| 31.2 | 2.882  | 7.1  |
| 31.6 | 2.849  | 13.8 |
| 32.5 | 2.772  | 2.8  |
| 34.0 | 2.651  | 3.7  |
| 34.6 | 2.611  | 5.3  |
| 35.0 | 2.576  | 7.4  |
| 35.4 | 2.550  | 7.6  |
| 36.0 | 2.510  | 6.8  |
| 37.4 | 2.418  | 2.4  |
| 38.5 | 2.353  | 4.2  |
| 39.5 | 2.294  | 3.1  |

Solid-state CP/MAS $^{13}C$ NMR of the crystalline material yielded a spectrum having the following chemical shifts ($\delta_c$ in ppm, unrounded): 13.771, 30.702, 44.121, 41.489, 54.598, 52.647, 47.073, 67.559, 174.932.

ATR-FT-IR yielded a spectrum having the following absorption peaks ($cm^{-1}$, unrounded): 725, 774, 808, 827, 985, 1039, 1070, 1110, 1144, 1194, 1277, 1291, 1353, 1369, 1388, 1426, 1438, 1467, 1659, 2789, 2835, 2918, 3088, 3144, 3422.

Example 16: Mixture of Forms I and II

To Compound A (0.12 gr.) was added dichloromethane (0.2 ml), and the mixture was heated to dissolve the compound. The clear solution was cooled at room temperature overnight.

Solid material which appeared to the naked eye to be crystalline formed in the solution. This material was collected by filtration and dried at room temperature under vacuum to give solid Compound A.

Solid-state CP/MAS $^{13}C$ NMR of the crystalline material yielded a spectrum having the following chemical shifts ($\delta_c$ in ppm, unrounded): 14.708, 14.581, 13.122, 30.010, 25.692, 53.942, 52.012, 49.300, 43.437, 40.832, 46.449, 66.949, 65.522, 63.884, 174.237.

This form is defined as a mixture of Forms I and Form II because of characteristic peaks in CP/MAS $^{13}$C NMR & ATR-FT-IR.

Example 17: Mixture of Forms I and II

To Compound A (0.12 gr.) was added toluene (0.5 ml), and the mixture was heated to dissolve the Compound A. The clear solution was cooled at room temperature overnight. Solid material which appeared to the naked eye to be crystalline formed in the solution. This material was collected by filtration and dried at room temperature under vacuum to give solid Compound A.

Solid-state CP/MAS $^{13}$C NMR of the crystalline material yielded a spectrum having the following chemical shifts ($\delta_c$ in ppm, unrounded): 15.331, 14.724, 13.275, 30.157, 29.055, 25.906, 54.082, 52.728, 52.228, 49.334, 43.489, 39.538, 37.700, 45.790, 44.884, 67.063, 65.623, 63.970, 175.004.

This form is defined as a mixture of Forms I and Form II because of characteristic peaks in CP/MAS $^{13}$C NMR & ATR-FT-IR.

Figure 16:
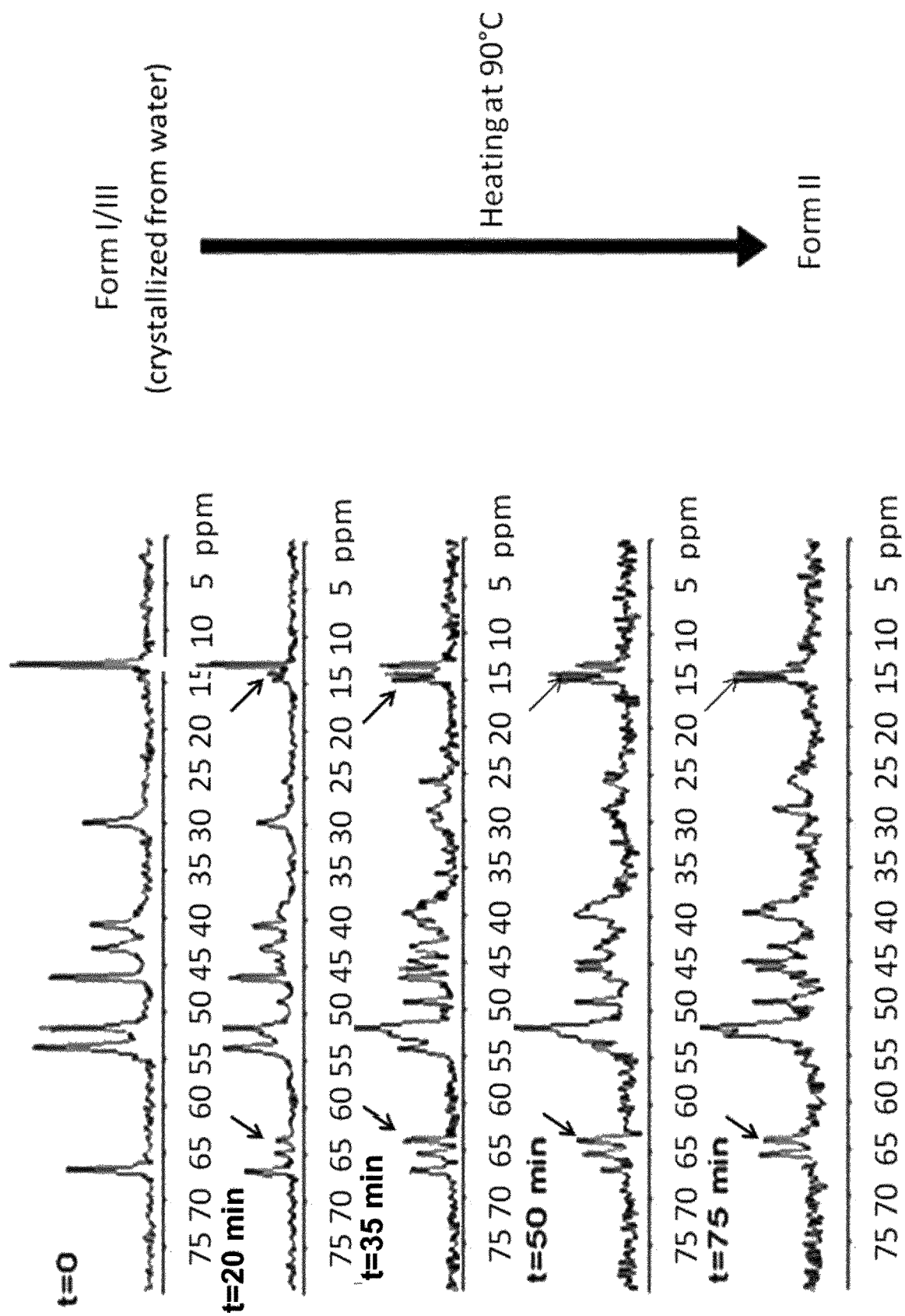
FIG. 16 represents solid-state CP/MAS $^{13}$C NMR of Compound A crystal Form I/III transformation to Form II as a function of time at 90° C. The arrow indicate diagnostic peaks of crystal Form H.

Example 18: Transformation of Form I to Form II by Heating a) During heating at 90° C. of Compound A crystal Form I (crystallized from ethyl acetate) the characteristic peaks of Form I decreased (particularly noticeable in solid-state CP/MAS $^{13}$C NMR spectrum in the regions 14-15, 26-29, 44-46 and 63-66 ppm), whereas those of Compound A crystal Form II increased [diagnostic peaks (15.4, 14.7), (29.1, 25.9), (64.0, 65.7) ppm]. Compound A crystal Form I was completely converted to Compound A crystal Form II in 4 hrs.

b) Crystalline Form I/III Compound A, crystallized from water, was heated at 90° C. for 75 min. Solid-state CP/MAS $^{13}$C NMR of the product confirmed that crystalline Form I/III was transformed to crystalline Form II (re FIG. 16).

c) Crystalline Form II Compound A was heated at 70° C. for 10 h, then left at room temperature overnight. Solid-state CP/MAS $^{13}$C NMR of the product confirmed that crystalline Form II was unchanged.

Example 19: Transformation of Form I to Form II by Melting a) Crystalline Form I/III Compound A (crystallized from water) was heated to 160° C., then the molten material was left at room temperature for crystallization. Solid-state CP/MAS $^{13}$C NMR of the product confirmed that crystalline Form II was obtained.

b) Crystalline Form II Compound A (crystallized from acetonitrile) was heated to 160° C., then the molten material was left at room temperature for crystallization. Solid-state CP/MAS $^{13}$C NMR of the product confirmed that crystalline Form II was obtained.

Example 20: Transformation of Form II to Form I or to a Mixture of Form I and III, Respectively, Under Ambient Conditions a) Crystalline Form II Compound A was left at room temperature for 90 days. It was confirmed by solid-state CP-MAS $^{13}$C NMR that crystalline Form II was transformed to crystalline Form I.

b) The API Form II transforms to Form I after exposure at 90% relative humidity for 3 hours as evidenced by modular DSC (MDSC). Thus Form II (MDSC=134.4° C.) converts to Form I (MDSC=104.0° C. and 133.8° C.).

c) The API Form II transforms to a mixture of Form I and III when exposed to ambient humidity at room temperature for four months as evidenced by MDSC (isotherms: 62.2° C., 104.2° C. and 134.1° C.).

Example 21: Crystal Form I does not Convert to Form III in High Humidity

Crystalline Form I Compound A (0.4149 g, crystallized from ethyl acetate) was placed in a desiccator at 95% relative humidity (saturated solution of Na$_2$HPO$_4$) at room temperature for one week. Analysis of the crystalline material by X-ray powder diffraction, ATR FT-IR, CP-MAS solid-state $^{13}$C NMR, DSC and TGA confirmed that the material was still crystalline Form I and it did not transform to Form III. This is another indication that Form I and Form III are different crystal forms.

Example 22: Transformation in Slurry

Acetonitrile (2 ml) was added to a mixture of crystalline Forms I and III of Compound A (0.15 g; crystallized from water) and the resulting slurry was stirred at room temperature for 6 hours, then the remaining solid was filtered. It was confirmed by solid-state CP-MAS $^{13}$C NMR that the mixture of crystalline Forms I and III was transformed to crystalline Form H.

Example 23: Phase Equilibration of Mixtures a) A pre-determined quantity of anhydrous crystalline and monohydrate crystalline forms of Compound A were individually mixed with a pre-determined quantity of either anhydrous or monohydrate forms of Compound A, and then equilibrated in acetone and monitored by XRPD. Substantially pure anhydrous crystalline form (Form II) was obtained from both experiments.

b) A pre-determined quantity of anhydrous crystalline and monohydrate crystalline forms of Compound A were individually mixed with a pre-determined quantity of either anhydrous or monohydrate forms of Compound A, and then equilibrated in water and monitored by XRPD. The solids were completely converted to substantially pure monohydrate Form III within 2 hours.

Example 24: The Physical Properties of Compound A Monohydrate Crystalline Form III The physical properties of Compound A monohydrate crystalline Form III are summarized in Tables 2, 3 and Examples 14 and 21.

TABLE 3

Physical characterization of Compound A monohydrate crystalline form (Form III).

| Sample form | Monohydrate Form |
|---|---|
| Appearance | White Powder |
| Physical description | Long rod-like crystals |
| $T_{onset}$ (° C.) | $T_{peak}$ (° C.) |

TABLE 3-continued

Physical characterization of Compound A monohydrate crystalline form (Form III).

| Sample form | Monohydrate Form | |
|---|---|---|
| DSC | 57.6 | 77.1 |
|  | 133.7 | 134.9 |
| X-ray powder diffraction | Crystalline 2 theta values: see Table 2. | |

Figure 4B:
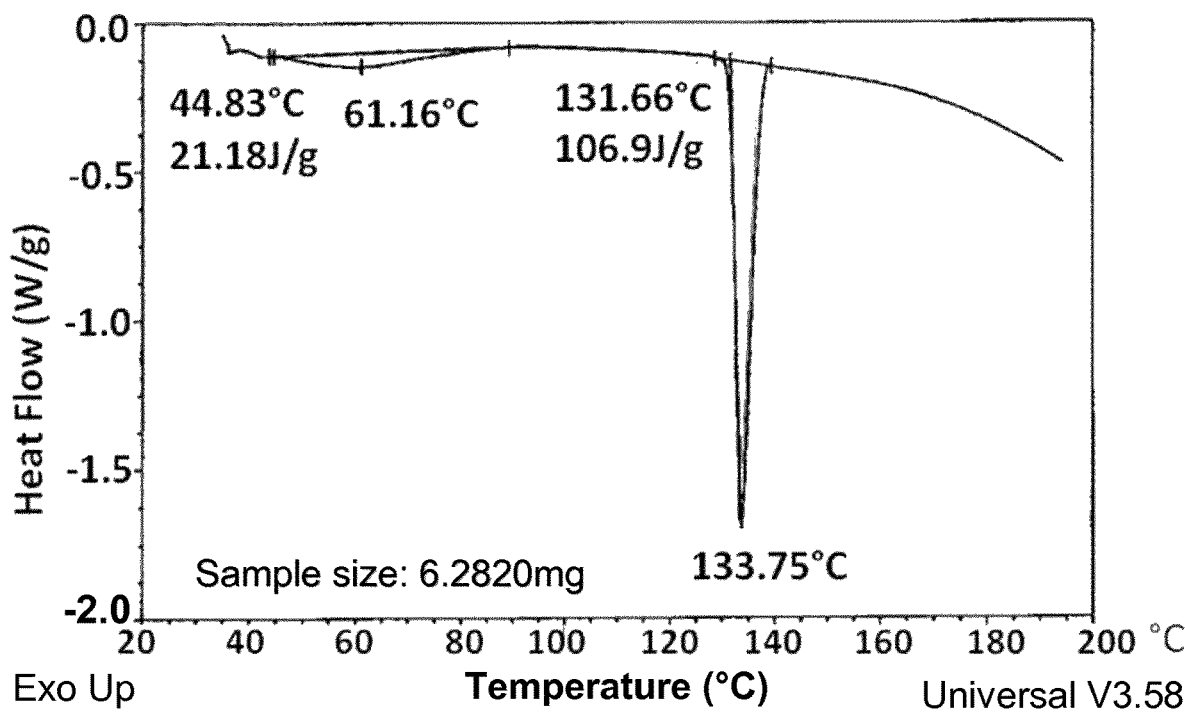

The X-ray powder diffraction pattern shows that the sample is a crystalline material (FIG. 2). DSC of this sample shows two DSC peaks, one at about 77.1° C. (broad) and the other at about 134.9° C. (FIG. 4A); and for the API 61.18° C. (broad) and 133.75° C. (FIG. 4B). TGA results (FIG. 5) show that there was 7.8% weight loss up to about 110° C., as expected from a stoichiometric monohydrate. After melting, thermal decomposition occurred immediately and the material was completely decomposed around 230° C.

The cGMP API Form III is highly stable under long-term conditions at 25° C./60% RH without change in appearance (white powder); in DSC (T=0, 64.2° C. and 133.8° C.; and T=12 months, 64.5° C. and 133.8° C. as expected from the characteristic features of Form III); in purity by HPLC (achiral), 100% and HPLC (chiral), 99.9-100%; in water content (7.6-8%). Form III does not convert to Form I. Furthermore, Form I does not convert to Form III. This is another indication that Form I and Form III are different and non-inter-convertible crystal forms.

Importantly the API Form III is physically stable and non-hygroscopic and no water was adsorbed to it from 8-90% relative humidity. As a consequence, the powder pattern also does not change. No water desorption was detected at relative humidity above 7%. At relative humidity below 7% Form III begins to dehydrate with virtually complete water loss being achieved at 2% relative humidity.

Aqueous solubility of the API (Form III)=5.3 mg/ml.

Example 25: Physical Characteristics of Compound A Anhydrous Crystalline Form (Form II)

The physical properties of Compound A anhydrous crystalline Form II are summarized in Tables 1 and 4.

TABLE 4

Physical characterization of Compound A anhydrous crystalline Form II.

| Sample form | Anhydrous form |
|---|---|
| Appearance | White Powder |
| Physical description | Needle-shaped |
| Melting point | 131.2-133.3° C. |

TABLE 4-continued

Physical characterization of Compound A anhydrous crystalline Form II.

| Sample form | Anhydrous form | |
|---|---|---|
|  | $T_{onset}$ (° C.) | $T_{peak}$ (° C.) |
| DSC | 134.2 | 135.4 |
| X-ray powder diffraction | Crystalline 2 theta values: See Table 1. | |

The X-ray powder diffraction pattern (FIG. 6; Table 1) shows the sample is crystalline with melting point of about 131.2-133.3° C. DSC shows that the crystalline material has a Tonset at about 134.2° C. and Tpeak at about 135.4° C. (FIG. 7A) and at about 134.29° C. for the API (FIG. 7B). TGA results (FIG. 8) show no significant weight loss before 110° C. After melting, thermal decomposition occurred; the material decomposed completely at about 250° C.

The API Form II is highly stable for over two years as anhydrous Form II if kept under dry atmosphere. The anhydrous Form II, when stored at ambient room temperature and humidity, begins to convert to the hydrate form. The evidence of partial conversion of the anhydrous to the hydrate is based on the increased water content observed on repeated handling. Upon equilibration of the anhydrous Form II at elevated humidity, conversion to the monohydrate Form III occurs based on the stoichiometric molar water uptake and thermal properties.

Figure 14:
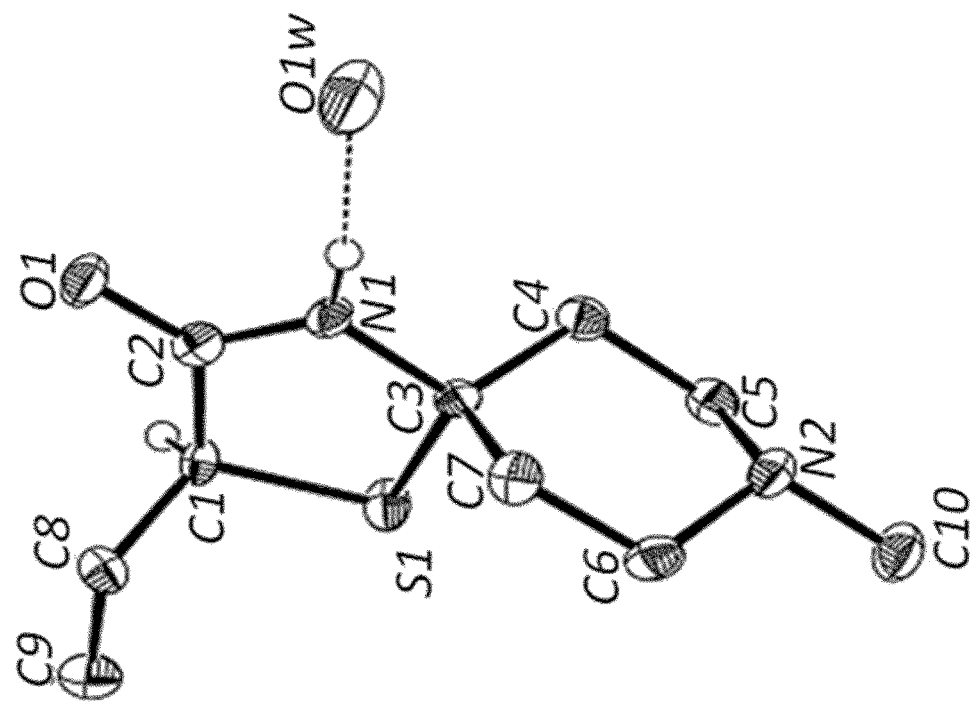
FIG. 14 presents the single crystal structure of Compound A with one molecule of water crystallized from ethyl acetate (Form I).
Figure 14:
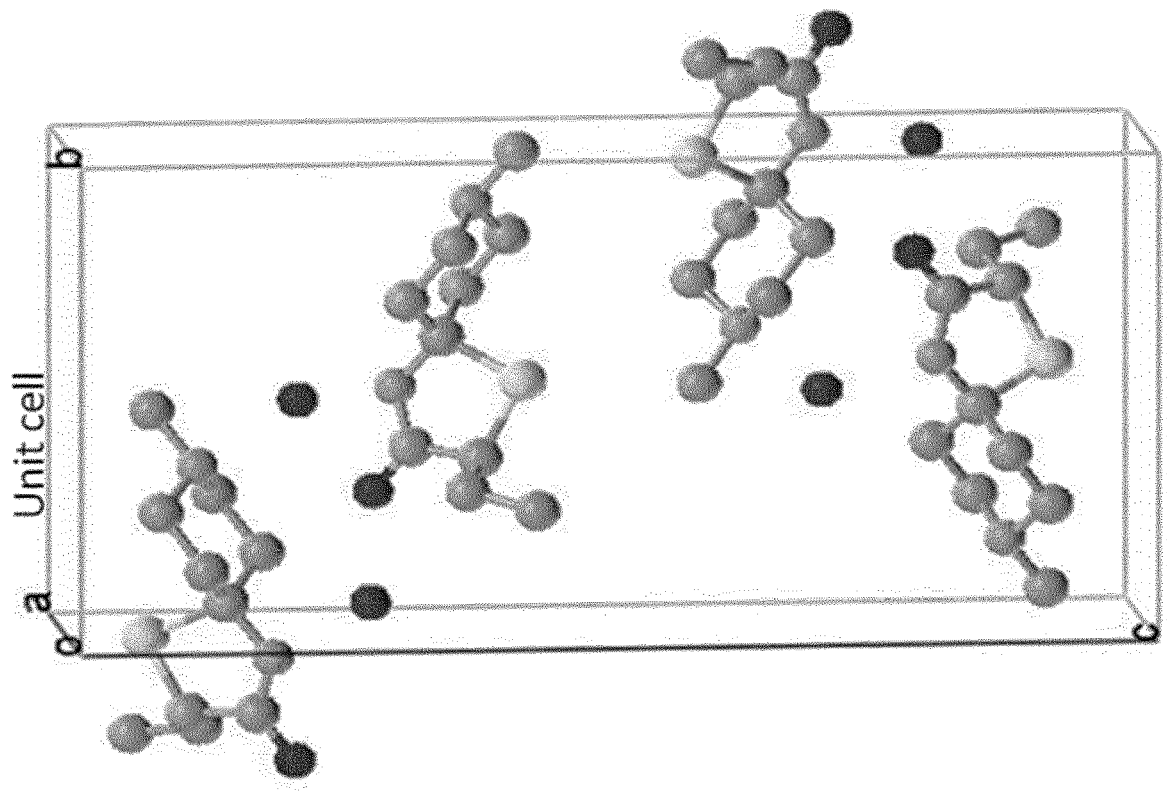

Solid-state CP/MAS $^{13}$C NMR can be used also to ascertain the number of molecules in the crystallographic asymmetric unit (Harris, *Analyst* 131 (2006), 351-373; Harris, *Solid State Sciences* 6 (2004), 1025-1037). Molecular crystals that contain more than one molecule of the same species in the asymmetric unit are in crystallographic different sites, so they have different environments. In consequence, NMR would show that they have different properties, and the analog atoms (for instance, carbons) will, in principle, differ in their chemical shifts. In general, when peaks appear as multiplets for $^{13}$C resonance, the number of components of such multiplets indicates the number of molecules in the asymmetric unit. Thus for Compound A crystal Form I (see FIG. 9B and Table 5)—one set of signals was observed, indicating that one molecule of Compound A is present in the asymmetric unit (re also Example 27; FIG. 14). On the other hand, for Compound A crystal Form II (see FIG. 9A and Table 5)—the doubling of some resonance peaks (particularly noticeable in the regions 14-15, 26-29, 44-46 and 63-66 ppm) indicates that more than one molecule of Compound A are present in the crystal unit (re also Example 25; FIG. 11). Examination of the solid-state CP/MAS $^{13}$C NMR spectrum of each form alone (Compound A crystal Form II and I, respectively) [FIG. 9A, diagnostic peaks (15.4, 14.7), (29.1, 25.9), (64.0, 65.7) ppm; FIG. 9B, diagnostic peaks 13.3, 30.2, 67.1 ppm] and the spectrum of a bona fide mixture of crystal Forms I and II [FIG. 9D, diagnostic peaks (15.4, 14.7, 13.3), (29.1, 25.9, 30.2), (64.0, 65.7, 67.1) ppm], show clearly that Compound A crystal Form II does not contain detectable amounts of crystal Form I. Furthermore, Compound A crystal Form II does not contain detectable amounts of Compound A crystal Form III (FIGS. 9C & 9D). Notably Form I and Form III have the same CP/MAS $^{13}$C NMR spectrum (FIGS. 9B and 9C).

TABLE 5

Solid-state CP/MAS $^{13}$C NMR chemical shifts ($\delta_c$ in ppm) of Compound A crystallized from various solvents.

| carbon | Solution in CDCl$_3$ | Form III* | ethyl acetate Form I | water Form I/III | acetonitrile Form II | hexane Form II | dioxane Form II |
|---|---|---|---|---|---|---|---|
| C3 | 175.37 | 174.93 | 174.36 | 174.41 | 175.01 | 174.96 | 174.97 |
| C5 | 63.41. | 67.56 | 67.09 | 67.08 | 65.29, 64.01 | 65.44, 64.09 | 65.56, 63.97 |
| C13 | 45.65. | 47.07 | 46.59 | 46.61 | 45.77, 44.97 | 45.79, 45.01 | 45.81, 44.96 |
| C7 | 52.89, | 52.65, | 52.15, | 52.16, | 52.33, | 52.29, | 52.31, |
| C9 | 52.74 | 54.60 | 54.08 | 54.14 | 49.33, | 49.35, | 49.34, |
| C2 | 48.98 | | | | 43.58, | 43.59, | 43.46, |
| C6 | 41.29, | 44.12, | 43.61, | 43.61, | 39.49, | 39.50 | 39.54 |
| C10 | 41.24 | 41.49 | 40.97 | 40.97 | 38.76 | | |
| C11 | 27.16 | 30.70 | 30.15 | 30.15 | 28.87, 26.01 | 28.99, 25.95 | 28.93, 25.96 |
| C12 | 11.46 | 13.77 | 13.27 | 13.27 | 15.37, 14.83 | 15.39, 14.83 | 15.36, 14.79 |

*Example 15

Under inverted light microscopy crystals obtained from ethyl acetate (Form I), water, and ethanol were plate-like crystals, while crystals obtained from isopropanol have flat shape crystals and crystals obtained from acetone, tetrahydrofuran and tert-butylmethyl ether have needle-like crystals. The anhydrous Form II of Compound A crystallized as needle-like crystals from acetonitrile, cyclohexane, hexane and diethyl ether.

Under scanning electron microscopy (SEM), the anhydrous Form II and monohydrate Form III of Compound A are long rod shaped crystals. However, the monohydrate lots of Form III appear to have a more uniform distribution of crystal size. The anhydrous sample appears to have a few long crystals among mostly smaller crystals. The surface texture of the anhydrous form appears smoother under the higher magnification compared to the monohydrate crystal surface.

Example 26: Single-Crystal X-Ray of Compound a Form II (Crystallized from Acetonitrile)

A single crystal of Compound A was attached to a glass fiber, with epoxy glue, and transferred to a Bruker SMART APEX CCD X-ray diffractometer equipped with a graphite-monochromator. Data were collected at 173K using MoKα radiation (λ=0.71073 Å) and the SMART software package. Immediately after collection, the raw data frames were transferred to the SAINT program package for integration and reduction. The structure was solved and refined by the SHELXTL software package. (All software by Bruker AXS GmbH, Karlsruhe, Germany). The single-crystal x-ray of Compound A anhydrous crystal data are summarized in Tables 6-11.

Figure 12A:
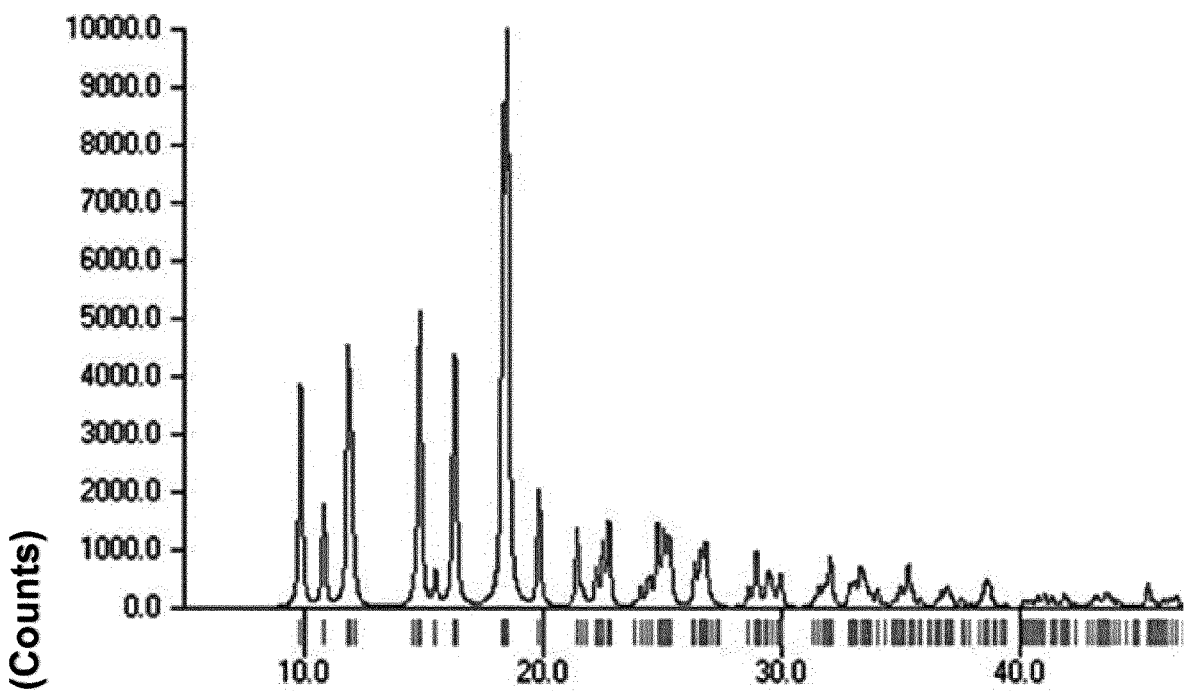
FIG. 12 presents three X-ray powder diffraction patterns for Compound A: A) simulated by using XPREP of a single crystal Form II (re FIG. 11); B) experimental XRPD pattern of the crystalline material Form II (cGMP API).
Figure 12B:
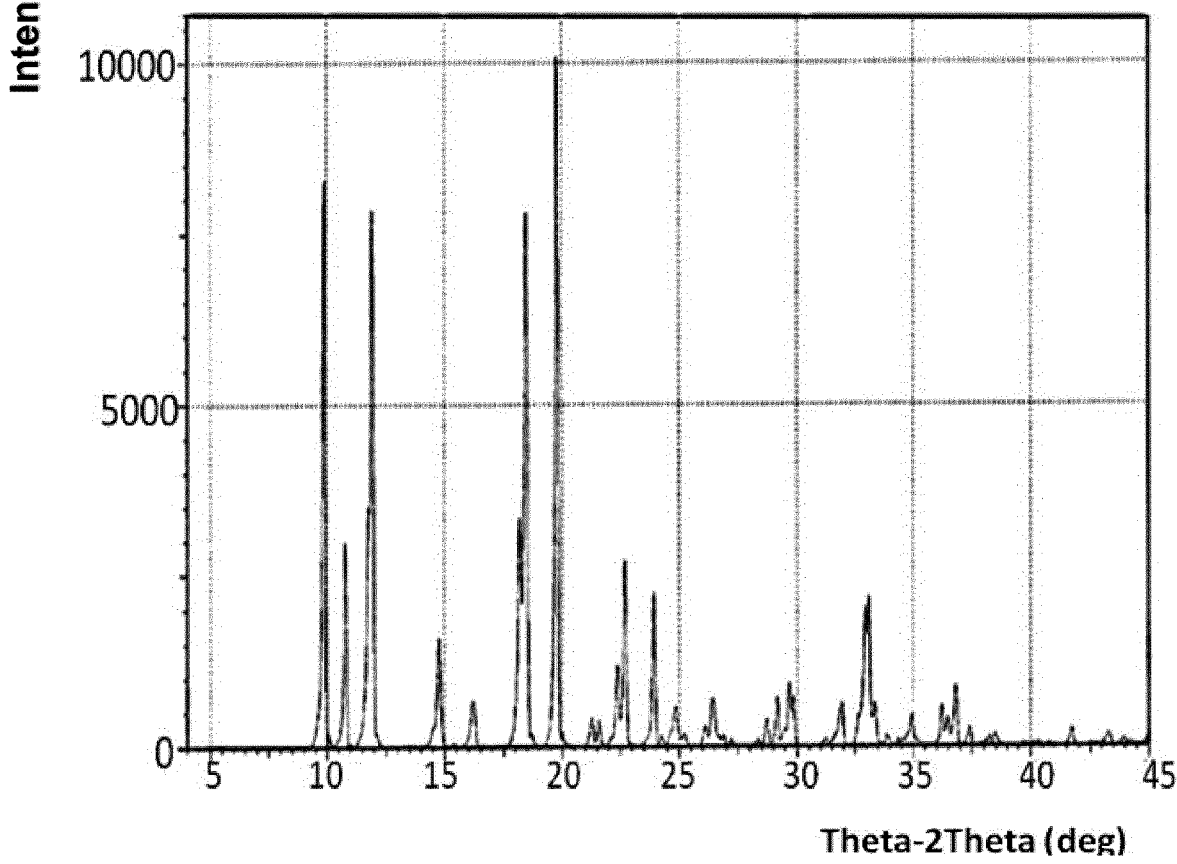

Compound A anhydrous crystal crystallized in the space group P2(1) with four molecules in the unit cell. There are two Compound A molecules in the asymmetric unit of the P2$_1$ chiral space group anhydrate crystal (as concluded also from the CP/MAS $^{13}$C NMR studies). These two molecules are conformationally different. Molecule 1 has a Twisted conformation of the five-membered ring with a pseudo-C$_2$ axis through the C=O bond. Molecule 2 has an Envelope conformation of the five-membered ring where the S-atom occupies the flap position. FIG. 11 shows the molecules and their position in the unit cell of the structure. The computer simulation of the anhydrous single crystal of Compound A and the XRPD patterns of the crystalline material Form II showed that both are the same polymorph (FIG. 12).

TABLE 6

Crystal data and structure refinement

| | |
|---|---|
| Empirical formula | C10 H18 N2 O S |
| Formula weight | 214.32 |
| Temperature | 173(1) K |
| Wavelength | 0.71073 Å |
| Crystal system | Monoclinic |
| Space group | P2(1) |
| Unit cell dimensions | a = 8.1416(13) Å  α = 90°. |
| | b = 7.9811(12) Å  β = 90.761(2)°. |
| | c = 17.878(3) Å  γ = 90°. |
| Volume | 1161.6(3) Å$^3$ |
| Z | 4 |
| Density (calculated) | 1.226 Mg/m$^3$ |
| Absorption coefficient | 0.251 mm$^{-1}$ |
| F(000) | 464 |
| Crystal size | 0.30 × 0.14 × 0.12 mm$^3$ |
| Theta range for data collection | 2.28 to 26.00°. |
| Index ranges | −10 <= h <= 10, −9 <= k <= 9, −22 <= l <= 22 |
| Reflections collected | 10907 |
| Independent reflections | 4514 [R(int) = 0.0339] |
| Completeness to theta = 26.00° | 99.8% |
| Absorption correction | None |
| Max. and min. transmission | 0.9705 and 0.9284 |
| Refinement method | Full-matrix least-squares on F$^2$ |
| Data/restraints/parameters | 4514/1/265 |
| Goodness-of-fit on F$^2$ | 1.306 |
| Final R indices [I > 2sigma(I)] | R1 = 0.0684, wR2 = 0.1467 |
| R indices (all data) | R1 = 0.0710, wR2 = 0.1478 |
| Absolute structure parameter | 0.04(11) |
| Largest diff. peak and hole | 0.560 and −0.453 e.Å$^{-3}$ |

TABLE 7

Atomic coordinates (×10$^4$) and equivalent isotropic displacement parameters (Å$^2$ × 10$^3$). U(eq) is defined as one third of the trace of the orthogonalized U$^{ij}$ tensor.

| | x | y | z | U(eq) |
|---|---|---|---|---|
| C(1) | 5771(5) | 7715(5) | 6074(2) | 23(1) |
| C(2) | 6746(5) | 8259(5) | 5395(2) | 21(1) |
| C(3) | 8368(5) | 5890(5) | 5781(2) | 20(1) |
| C(4) | 7760(5) | 4260(5) | 5419(2) | 23(1) |
| C(5) | 8163(5) | 2750(5) | 5893(2) | 23(1) |
| C(6) | 10525(5) | 4131(5) | 6431(2) | 24(1) |

TABLE 7-continued

Atomic coordinates (×10⁴) and equivalent isotropic displacement parameters (Å² × 10³). U(eq) is defined as one third of the trace of the orthogonalized $U^{ij}$ tensor.

|  | x | y | z | U(eq) |
|---|---|---|---|---|
| C(7) | 10190(5) | 5704(5) | 5980(2) | 21(1) |
| C(8) | 5135(6) | 9150(6) | 6533(3) | 34(1) |
| C(9) | 4111(7) | 8589(6) | 7191(3) | 42(1) |
| C(10) | 10335(6) | 1123(6) | 6449(2) | 36(1) |
| C(11) | 3718(5) | 8794(5) | 1315(2) | 20(1) |
| C(12) | 3084(5) | 9024(5) | 517(2) | 21(1) |
| C(13) | 1508(4) | 6554(6) | 837(2) | 21(1) |
| C(14) | −348(4) | 6333(6) | 905(2) | 22(1) |
| C(15) | −800(5) | 4843(5) | 1373(2) | 25(1) |
| C(16) | 1715(5) | 3439(6) | 1057(3) | 31(1) |
| C(17) | 2231(5) | 4902(5) | 571(2) | 23(1) |
| C(18) | 5547(5) | 8401(6) | 1345(2) | 28(1) |
| C(19) | 6231(6) | 8394(6) | 2142(2) | 34(1) |
| C(20) | −569(7) | 1870(6) | 1526(3) | 41(1) |
| N(1) | 8088(4) | 7321(5) | 5305(2) | 24(1) |
| N(2) | 9937(4) | 2649(4) | 6029(2) | 22(1) |
| N(3) | 1898(4) | 7927(4) | 338(2) | 21(1) |
| N(4) | −90(4) | 3308(4) | 1074(2) | 23(1) |
| O(1) | 6317(3) | 9427(4) | 4993(2) | 28(1) |
| O(2) | 3610(3) | 10103(4) | 106(2) | 28(1) |
| S(1) | 7158(1) | 6385(1) | 6618(1) | 26(1) |
| S(2) | 2420(1) | 7220(1) | 1742(1) | 28(1) |

TABLE 8

Bond lengths [Å] and angles [°]

| C(1)—C(8) | 1.505(6) |
|---|---|
| C(1)—C(2) | 1.521(6) |
| C(1)—S(1) | 1.822(4) |
| C(1)—H(1) | 1.0000 |
| C(2)—O(1) | 1.225(5) |
| C(2)—N(1) | 1.336(5) |
| C(3)—N(1) | 1.440(5) |
| C(3)—C(7) | 1.529(5) |
| C(3)—C(4) | 1.532(6) |
| C(3)—S(1) | 1.845(4) |
| C(4)—C(5) | 1.507(6) |
| C(4)—H(4A) | 0.9900 |
| C(4)—H(4B) | 0.9900 |
| C(5)—N(2) | 1.463(5) |
| C(5)—H(5A) | 0.9900 |
| C(5)—H(5B) | 0.9900 |
| C(6)—N(2) | 1.462(5) |
| C(6)—C(7) | 1.514(6) |
| C(6)—H(6A) | 0.9900 |
| C(6)—H(6B) | 0.9900 |
| C(7)—H(7A) | 0.9900 |
| C(7)—H(7B) | 0.9900 |
| C(8)—C(9) | 1.519(6) |
| C(8)—H(8A) | 0.9900 |
| C(8)—H(8B) | 0.9900 |
| C(9)—H(9A) | 0.9800 |
| C(9)—H(9B) | 0.9800 |
| C(9)—H(9C) | 0.9800 |
| C(10)—N(2) | 1.465(5) |
| C(10)—H(10A) | 0.9800 |
| C(10)—H(10B) | 0.9800 |
| C(10)—H(10C) | 0.9800 |
| C(11)—C(18) | 1.521(5) |
| C(11)—C(12) | 1.522(6) |
| C(11)—S(2) | 1.816(4) |
| C(11)—H(11) | 1.0000 |
| C(12)—O(2) | 1.213(5) |
| C(12)—N(3) | 1.339(5) |
| C(13)—N(3) | 1.451(5) |
| C(13)—C(17) | 1.523(6) |
| C(13)—C(14) | 1.528(5) |
| C(13)—S(2) | 1.848(4) |
| C(14)—C(15) | 1.502(6) |
| C(14)—H(14A) | 0.9900 |
| C(14)—H(14B) | 0.9900 |
| C(15)—N(4) | 1.460(5) |
| C(15)—H(15A) | 0.9900 |
| C(15)—H(15B) | 0.9900 |
| C(16)—N(4) | 1.474(5) |
| C(16)—C(17) | 1.518(6) |
| C(16)—H(16A) | 0.9900 |
| C(16)—H(16B) | 0.9900 |
| C(17)—H(17A) | 0.9900 |
| C(17)—H(17B) | 0.9900 |
| C(18)—C(19) | 1.523(6) |
| C(18)—H(18A) | 0.9900 |
| C(18)—H(18B) | 0.9900 |
| C(19)—H(19A) | 0.9800 |
| C(19)—H(19B) | 0.9800 |
| C(19)—H(19C) | 0.9800 |
| C(20)—N(4) | 1.460(5) |
| C(20)—H(20A) | 0.9800 |
| C(20)—H(20B) | 0.9800 |
| C(20)—H(20C) | 0.9800 |
| N(1)—H(1N1) | 0.84(5) |
| N(3)—H(1N3) | 0.87(4) |
| C(8)—C(1)—C(2) | 113.9(3) |
| C(8)—C(1)—S(1) | 111.5(3) |
| C(2)—C(1)—S(1) | 105.4(3) |
| C(8)—C(1)—H(1) | 108.6 |
| C(2)—C(1)—H(1) | 108.6 |
| S(1)—C(1)—H(1) | 108.6 |
| O(1)—C(2)—N(1) | 125.7(4) |
| O(1)—C(2)—C(1) | 122.5(4) |
| N(1)—C(2)—C(1) | 111.9(3) |
| N(1)—C(3)—C(7) | 111.1(3) |
| N(1)—C(3)—C(4) | 112.1(3) |
| C(7)—C(3)—C(4) | 108.9(3) |
| N(1)—C(3)—S(1) | 103.1(3) |
| C(7)—C(3)—S(1) | 111.0(3) |
| C(4)—C(3)—S(1) | 110.6(3) |
| C(5)—C(4)—C(3) | 112.0(3) |
| C(5)—C(4)—H(4A) | 109.2 |
| C(3)—C(4)—H(4A) | 109.2 |
| C(5)—C(4)—H(4B) | 109.2 |
| C(3)—C(4)—H(4B) | 109.2 |
| H(4A)—C(4)—H(4B) | 107.9 |
| N(2)—C(5)—C(4) | 110.2(3) |
| N(2)—C(5)—H(5A) | 109.6 |
| C(4)—C(5)—H(5A) | 109.6 |
| N(2)—C(5)—H(5B) | 109.6 |
| C(4)—C(5)—H(5B) | 109.6 |
| H(5A)—C(5)—H(5B) | 108.1 |
| N(2)—C(6)—C(7) | 110.8(3) |
| N(2)—C(6)—H(6A) | 109.5 |
| C(7)—C(6)—H(6A) | 109.5 |
| N(2)—C(6)—H(6B) | 109.5 |
| C(7)—C(6)—H(6B) | 109.5 |
| H(6A)—C(6)—H(6B) | 108.1 |
| C(6)—C(7)—C(3) | 111.8(3) |
| C(6)—C(7)—H(7A) | 109.2 |
| C(3)—C(7)—H(7A) | 109.2 |
| C(6)—C(7)—H(7B) | 109.2 |
| C(3)—C(7)—H(7B) | 109.2 |
| H(7A)—C(7)—H(7B) | 107.9 |
| C(1)—C(8)—C(9) | 113.3(4) |
| C(1)—C(8)—H(8A) | 108.9 |
| C(9)—C(8)—H(8A) | 108.9 |
| C(1)—C(8)—H(8B) | 108.9 |
| C(9)—C(8)—H(8B) | 108.9 |
| H(8A)—C(8)—H(8B) | 107.7 |
| C(8)—C(9)—H(9A) | 109.5 |
| C(8)—C(9)—H(9B) | 109.5 |
| H(9A)—C(9)—H(9B) | 109.5 |
| C(8)—C(9)—H(9C) | 109.5 |
| H(9A)—C(9)—H(9C) | 109.5 |
| H(9B)—C(9)—H(9C) | 109.5 |
| N(2)—C(10)—H(10A) | 109.5 |
| N(2)—C(10)—H(10B) | 109.5 |
| H(10A)—C(10)—H(10B) | 109.5 |
| N(2)—C(10)—H(10C) | 109.5 |
| H(10A)—C(10)—H(10C) | 109.5 |

TABLE 8-continued

| Bond lengths [Å] and angles [°] | |
|---|---|
| H(10B)—C(10)—H(10C) | 109.5 |
| C(18)—C(11)—C(12) | 112.2(3) |
| C(18)—C(11)—S(2) | 114.7(3) |
| C(12)—C(11)—S(2) | 106.5(3) |
| C(18)—C(11)—H(11) | 107.7 |
| C(12)—C(11)—H(11) | 107.7 |
| S(2)—C(11)—H(11) | 107.7 |
| O(2)—C(12)—N(3) | 125.3(4) |
| O(2)—C(12)—C(11) | 122.4(4) |
| N(3)—C(12)—C(11) | 112.3(3) |
| N(3)—C(13)—C(17) | 111.9(3) |
| N(3)—C(13)—C(14) | 111.2(3) |
| C(17)—C(13)—C(14) | 108.1(3) |
| N(3)—C(13)—S(2) | 103.4(3) |
| C(17)—C(13)—S(2) | 111.7(3) |
| C(14)—C(13)—S(2) | 110.5(2) |
| C(15)—C(14)—C(13) | 112.7(3) |
| C(15)—C(14)—H(14A) | 109.1 |
| C(13)—C(14)—H(14A) | 109.1 |
| C(15)—C(14)—H(14B) | 109.1 |
| C(13)—C(14)—H(14B) | 109.1 |
| H(14A)—C(14)—H(14B) | 107.8 |
| N(4)—C(15)—C(14) | 111.0(3) |
| N(4)—C(15)—H(15A) | 109.4 |
| C(14)—C(15)—H(15A) | 109.4 |
| N(4)—C(15)—H(15B) | 109.4 |
| C(14)—C(15)—H(15B) | 109.4 |
| H(15A)—C(15)—H(15B) | 108.0 |
| N(4)—C(16)—C(17) | 110.5(3) |
| N(4)—C(16)—H(16A) | 109.6 |
| C(17)—C(16)—H(16A) | 109.6 |
| N(4)—C(16)—H(16B) | 109.6 |
| C(17)—C(16)—H(16B) | 109.6 |
| H(16A)—C(16)—H(16B) | 108.1 |
| C(16)—C(17)—C(13) | 112.1(3) |
| C(16)—C(17)—H(17A) | 109.2 |
| C(13)—C(17)—H(17A) | 109.2 |
| C(16)—C(17)—H(17B) | 109.2 |
| C(13)—C(17)—H(17B) | 109.2 |
| H(17A)—C(17)—H(17B) | 107.9 |
| C(11)—C(18)—C(19) | 112.3(4) |
| C(11)—C(18)—H(18A) | 109.1 |
| C(19)—C(18)—H(18A) | 109.1 |
| C(11)—C(18)—H(18B) | 109.1 |
| C(19)—C(18)—H(18B) | 109.1 |
| H(18A)—C(18)—H(18B) | 107.9 |
| C(18)—C(19)—H(19A) | 109.5 |
| C(18)—C(19)—H(19B) | 109.5 |
| H(19A)—C(19)—H(19B) | 109.5 |
| C(18)—C(19)—H(19C) | 109.5 |
| H(19A)—C(19)—H(19C) | 109.5 |
| H(19B)—C(19)—H(19C) | 109.5 |
| N(4)—C(20)—H(20A) | 109.5 |
| N(4)—C(20)—H(20B) | 109.5 |
| H(20A)—C(20)—H(20B) | 109.5 |
| N(4)—C(20)—H(20C) | 109.5 |
| H(20A)—C(20)—H(20C) | 109.5 |
| H(20B)—C(20)—H(20C) | 109.5 |
| C(2)—N(1)—C(3) | 119.7(3) |
| C(2)—N(1)—H(1N1) | 117(4) |
| C(3)—N(1)—H(1N1) | 122(4) |
| C(6)—N(2)—C(5) | 110.6(3) |
| C(6)—N(2)—C(10) | 110.6(3) |
| C(5)—N(2)—C(10) | 110.0(3) |
| C(12)—N(3)—C(13) | 120.7(3) |
| C(12)—N(3)—H(1N3) | 121(3) |
| C(13)—N(3)—H(1N3) | 118(3) |
| C(15)—N(4)—C(20) | 110.3(3) |
| C(15)—N(4)—C(16) | 110.4(3) |
| C(20)—N(4)—C(16) | 109.9(4) |
| C(1)—S(1)—C(3) | 91.46(17) |
| C(11)—S(2)—C(13) | 93.49(19) |

Symmetry transformations used to generate equivalent atoms:

TABLE 9

Anisotropic displacement parameters (Å$^2$ × 10$^3$). The anisotropic displacement factor exponent takes the form: $-2\pi^2[h^2 a^{*2}U^{11}+\ldots+2hka^*b^*U^{12}]$

| | $U^{11}$ | $U^{22}$ | $U^{33}$ | $U^{23}$ | $U^{13}$ | $U^{12}$ |
|---|---|---|---|---|---|---|
| C(1) | 13(2) | 20(2) | 34(2) | 0(2) | 2(2) | 3(2) |
| C(2) | 16(2) | 19(2) | 28(2) | 1(2) | −1(2) | 0(2) |
| C(3) | 13(2) | 28(2) | 20(2) | 4(2) | 5(2) | 4(2) |
| C(4) | 14(2) | 30(2) | 24(2) | −2(2) | 1(2) | −1(2) |
| C(5) | 24(2) | 19(2) | 26(2) | −1(2) | 8(2) | −4(2) |
| C(6) | 19(2) | 28(2) | 24(2) | −2(2) | −5(2) | 8(2) |
| C(7) | 17(2) | 23(2) | 23(2) | −3(2) | 1(2) | 2(2) |
| C(8) | 27(2) | 23(2) | 51(3) | 3(2) | 15(2) | 3(2) |
| C(9) | 43(3) | 29(3) | 54(3) | 7(2) | 24(2) | 12(2) |
| C(10) | 50(3) | 33(3) | 26(2) | 11(2) | 12(2) | 20(2) |
| C(11) | 17(2) | 18(2) | 26(2) | 0(2) | 3(2) | −2(2) |
| C(12) | 12(2) | 20(2) | 31(2) | 2(2) | 2(2) | 8(2) |
| C(13) | 11(2) | 34(2) | 19(2) | −7(2) | −1(1) | −1(2) |
| C(14) | 13(2) | 25(2) | 28(2) | −9(2) | −1(2) | −3(2) |
| C(15) | 20(2) | 32(2) | 23(2) | −2(2) | 6(2) | −6(2) |
| C(16) | 24(2) | 31(2) | 36(2) | 3(2) | −2(2) | 8(2) |
| C(17) | 15(2) | 28(2) | 25(2) | −5(2) | 3(2) | −3(2) |
| C(18) | 13(2) | 38(2) | 34(2) | −4(2) | −2(2) | −1(2) |
| C(19) | 32(2) | 38(2) | 32(2) | −4(2) | −5(2) | 2(2) |
| C(20) | 50(3) | 38(2) | 35(2) | 12(2) | −3(2) | −16(2) |
| N(1) | 16(2) | 27(2) | 28(2) | 5(2) | 13(1) | 5(2) |
| N(2) | 23(2) | 23(2) | 19(2) | 2(1) | 5(1) | 5(1) |
| N(3) | 18(2) | 25(2) | 20(2) | 5(1) | −5(1) | −3(1) |
| N(4) | 21(2) | 21(2) | 26(2) | 0(1) | −2(1) | −5(1) |
| O(1) | 21(2) | 26(2) | 39(2) | 10(1) | 2(1) | 5(1) |
| O(2) | 22(2) | 23(2) | 40(2) | 12(1) | −2(1) | −2(1) |
| S(1) | 26(1) | 31(1) | 20(1) | 1(1) | 6(1) | 10(1) |
| S(2) | 29(1) | 37(1) | 18(1) | 2(1) | −5(1) | −18(1) |

TABLE 10

Hydrogen coordinates (×10$^4$) and isotropic displacement parameters (Å$^2$ × 10$^3$)

| | x | y | z | U(eq) |
|---|---|---|---|---|
| H(1) | 4816 | 7024 | 5898 | 27 |
| H(4A) | 6555 | 4325 | 5341 | 27 |
| H(4B) | 8271 | 4131 | 4923 | 27 |
| H(5A) | 7589 | 2832 | 6376 | 28 |
| H(5B) | 7780 | 1722 | 5635 | 28 |
| H(6A) | 11720 | 4027 | 6529 | 28 |
| H(6B) | 9968 | 4211 | 6918 | 28 |
| H(7A) | 10834 | 5669 | 5515 | 25 |
| H(7B) | 10556 | 6693 | 6273 | 25 |
| H(8A) | 4459 | 9888 | 6207 | 40 |
| H(8B) | 6079 | 9816 | 6722 | 40 |
| H(9A) | 3197 | 7894 | 7010 | 63 |
| H(9B) | 3678 | 9575 | 7450 | 63 |
| H(9C) | 4798 | 7938 | 7539 | 63 |
| H(10A) | 11527 | 1049 | 6526 | 54 |
| H(10B) | 9950 | 142 | 6167 | 54 |
| H(10C) | 9794 | 1157 | 6935 | 54 |
| H(11) | 3545 | 9872 | 1588 | 24 |
| H(14A) | −820 | 7355 | 1130 | 27 |
| H(14B) | −838 | 6201 | 398 | 27 |
| H(15A) | −400 | 5015 | 1892 | 30 |
| H(15B) | −2011 | 4734 | 1384 | 30 |
| H(16A) | 2181 | 2387 | 857 | 37 |
| H(16B) | 2150 | 3598 | 1572 | 37 |
| H(17A) | 1867 | 4693 | 49 | 27 |
| H(17B) | 3444 | 4985 | 577 | 27 |
| H(18A) | 6144 | 9246 | 1048 | 34 |
| H(18B) | 5736 | 7290 | 1115 | 34 |
| H(19A) | 6019 | 9481 | 2377 | 51 |
| H(19B) | 7417 | 8190 | 2133 | 51 |
| H(19C) | 5696 | 7507 | 2429 | 51 |
| H(20A) | −182 | 2033 | 2042 | 61 |

TABLE 10-continued

Hydrogen coordinates ($\times 10^4$) and isotropic displacement parameters ($\text{Å}^2 \times 10^3$)

| | x | y | z | U(eq) |
|---|---|---|---|---|
| H(20B) | −78 | 850 | 1321 | 61 |
| H(20C) | −1768 | 1764 | 1518 | 61 |
| H(1N1) | 8640(60) | 7490(70) | 4920(30) | 37(14) |
| H(1N3) | 1400(50) | 7970(50) | −90(20) | 10(10) |

TABLE 11

Torsion angles [°].

| | |
|---|---|
| C(8)—C(1)—C(2)—O(1) | −42.0(6) |
| S(1)—C(1)—C(2)—O(1) | −164.6(3) |
| C(8)—C(1)—C(2)—N(1) | 137.8(4) |
| S(1)—C(1)—C(2)—N(1) | 15.3(4) |
| N(1)—C(3)—C(4)—C(5) | 175.9(3) |
| C(7)—C(3)—C(4)—C(5) | 52.5(4) |
| S(1)—C(3)—C(4)—C(5) | −69.7(4) |
| C(3)—C(4)—C(5)—N(2) | −57.7(4) |
| N(2)—C(6)—C(7)—C(3) | 56.5(4) |
| N(1)—C(3)—C(7)—C(6) | −175.6(3) |
| C(4)—C(3)—C(7)—C(6) | −51.6(4) |
| S(1)—C(3)—C(7)—C(6) | 70.3(4) |
| C(2)—C(1)—C(8)—C(9) | 177.9(4) |
| S(1)—C(1)—C(8)—C(9) | −63.0(5) |
| C(18)—C(11)—C(12)—O(2) | −60.3(5) |
| S(2)—C(11)—C(12)—O(2) | 173.4(3) |
| C(18)—C(11)—C(12)—N(3) | 120.3(4) |
| S(2)—C(11)—C(12)—N(3) | −6.0(4) |
| N(3)—C(13)—C(14)—C(15) | 175.8(3) |
| C(17)—C(13)—C(14)—C(15) | 52.6(4) |
| S(2)—C(13)—C(14)—C(15) | −70.0(4) |
| C(13)—C(14)—C(15)—N(4) | −57.1(4) |
| N(4)—C(16)—C(17)—C(13) | 57.5(5) |
| N(3)—C(13)—C(17)—C(16) | −175.5(3) |
| C(14)—C(13)—C(17)—C(16) | −52.7(4) |
| S(2)—C(13)—C(17)—C(16) | 69.1(4) |
| C(12)—C(11)—C(18)—C(19) | 172.5(4) |
| S(2)—C(11)—C(18)—C(19) | −65.7(5) |
| O(1)—C(2)—N(1)—C(3) | −174.4(4) |
| C(1)—C(2)—N(1)—C(3) | 5.7(5) |
| C(7)—C(3)—N(1)—C(2) | −142.2(4) |
| C(4)—C(3)—N(1)—C(2) | 95.7(4) |
| S(1)—C(3)—N(1)—C(2) | −23.2(4) |
| C(7)—C(6)—N(2)—C(5) | −60.6(4) |
| C(7)—C(6)—N(2)—C(10) | 177.2(3) |
| C(4)—C(5)—N(2)—C(6) | 61.1(4) |
| C(4)—C(5)—N(2)—C(10) | −176.4(3) |
| O(2)—C(12)—N(3)—C(13) | 172.1(4) |
| C(11)—C(12)—N(3)—C(13) | −8.5(5) |
| C(17)—C(13)—N(3)—C(12) | −102.3(4) |
| C(14)—C(13)—N(3)—C(12) | 136.6(4) |
| S(2)—C(13)—N(3)—C(12) | 18.1(4) |
| C(14)—C(15)—N(4)—C(20) | −178.9(3) |
| C(14)—C(15)—N(4)—C(16) | 59.5(4) |
| C(17)—C(16)—N(4)—C(15) | −59.6(4) |
| C(17)—C(16)—N(4)—C(20) | 178.5(4) |
| C(8)—C(1)—S(1)—C(3) | −147.8(3) |
| C(2)—C(1)—S(1)—C(3) | −23.8(4) |
| N(1)—C(3)—S(1)—C(1) | 26.0(3) |
| C(7)—C(3)—S(1)—C(1) | 145.1(3) |
| C(4)—C(3)—S(1)—C(1) | −94.0(3) |
| C(18)—C(11)—S(2)—C(13) | −111.2(3) |
| C(12)—C(11)—S(2)—C(13) | 13.6(3) |
| N(3)—C(13)—S(2)—C(11) | −17.1(3) |
| C(17)—C(13)—S(2)—C(11) | 103.4(3) |
| C(14)—C(13)—S(2)—C(11) | −136.1(3) |

Symmetry transformations used to generate equivalent atoms:

TABLE 12

Hydrogen bonds

| D-H . . . A | d(D-H) | d(H . . . A) | d(D . . . A) | <(DHA) |
|---|---|---|---|---|
| N(3)—H(1N3) . . . N(4)#1 | 0.87(4) | 2.06(4) | 2.921(5) | 174(4) |
| N(1)—H(1N1) . . . N(2)#2 | 0.84(5) | 2.07(5) | 2.905(5) | 174(5) |

Symmetry transformations used to generate equivalent atoms:
1 −x,y+½,−z  #2 −x+2,y+½,−z+1

Example 27: Single-Crystal X-Ray of Compound A Crystal Form I (Crystallized from Ethyl Acetate)

Compound A single crystal Form I crystallized in the space group P2(1)2(1)2(1) with four molecules in the unit cell. There is one Compound A molecule in the asymmetric unit of the monohydrate crystal measured at low temperature [173(1) K]. FIG. 14 shows the molecule and its position in the unit cell of the structure. The molecule has a Twisted conformation of the five-membered ring with a pseudo-$C_2$ axis through the C═O bond. There are two strong hydrogen-bonds in Compound A crystal Form I (crystallized from ethyl acetate): amideN(1) . . . O(1w) 2.757 Ang, amideH(1) . . . O(1w) 1.947 Ang, and N(1)-H(1) . . . O(1w) 172.88 deg; and O(1w) . . . O(1)carbonyl 2.735 Ang, waterH(1w) . . . O(1w) 1.945 Ang, O(1w)-H(1w) . . . O(1) 165.38 deg. There is also one weak hydrogen-bond: piperidineN(2) . . . O(1w) 2.852 Ang, waterH(2w) . . . N(2) 2.302 Ang, O(1w)-H(2w) . . . N(2) 118.36 deg. Without wishing to be bound by theory, inventors believe that this hydrogen-bonded water molecule is the one responsible for the DSC/TGA peak at 104° C.

Figure 13:
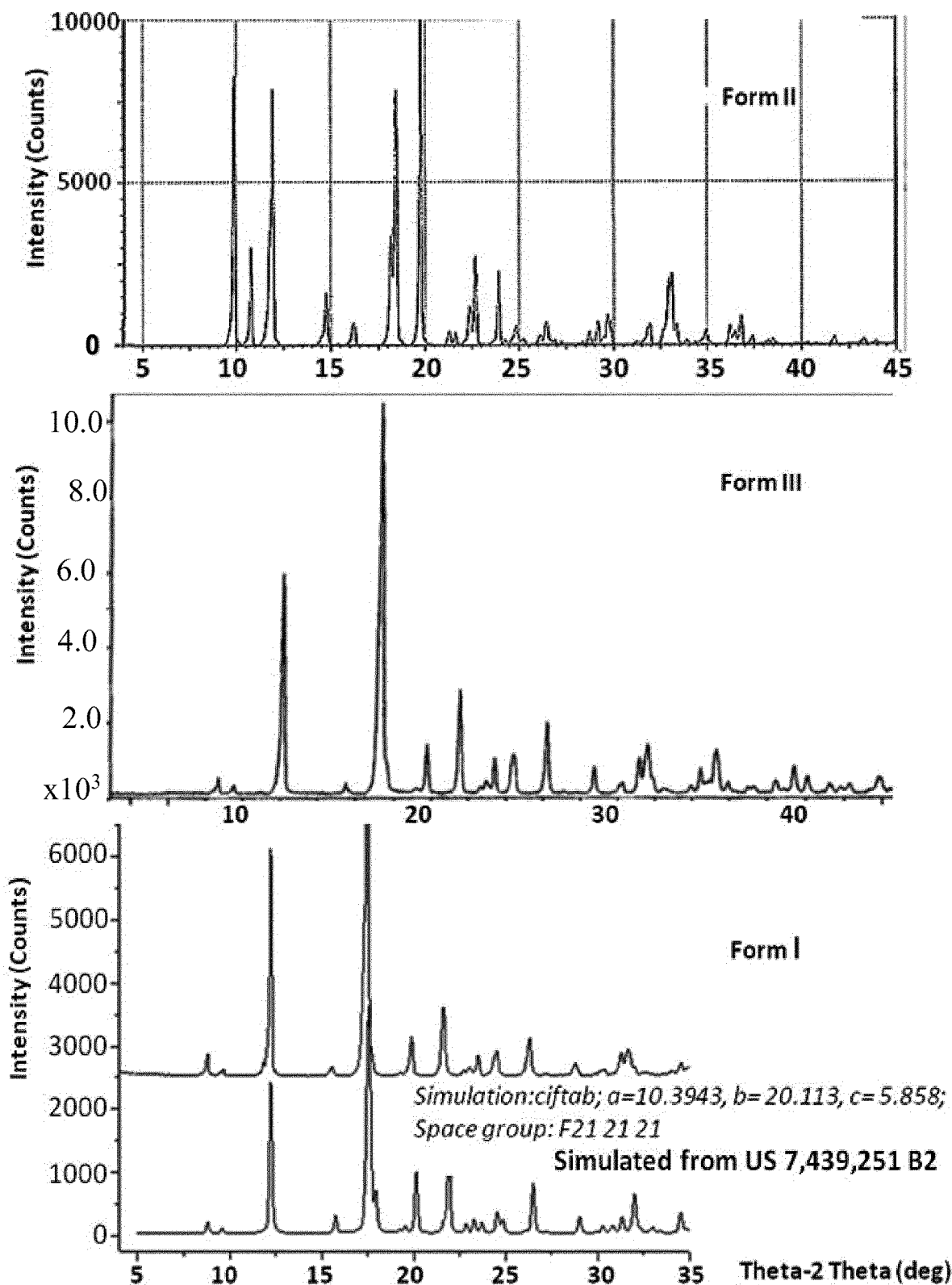
FIG. 13 presents three X-ray powder diffraction patterns for Compound A: experimental XRPD patterns of the crystalline material of Form I (crystallized from ethyl acetate); Form II (the cGMP API); Form III (the cGMP API); and simulated by using XPREP of a single crystal form as shown in U.S. Pat. No. 7,439,251 B2.

FIG. 13 presents three X-ray powder diffraction patterns for Compound A Form I, II and III, respectively, and simulated by using XPREP of a single crystal form as shown in U.S. Pat. No. 7,439,251B2. Notably, while the experimental powder diffraction patterns of Compound A crystal Form I and crystal Form III are similar, there are still several differences in diffraction angles when compared to the computer-simulated pattern (DBWS-9807 Rietveld program) drawn on the basis of single-crystal data as shown in U.S. Pat. No. 7,439,251B2 (re Table 13: peaks* of diffraction angles >+/−2 deg). Thus the XRPD of Form I and Form III are not identical to the XPREP of the single crystal of Compound A-hydrate as published in U.S. Pat. No. 7,439,251B2, which is a further confirmation that Form I and Form III are different, unpublished and novel polymorphic forms (Table 13). Furthermore, the XRPD of the polymorphic Form II is identical to the simulated XRPD of the single crystal of this Form (FIG. 12), but differs robustly from the XRPD simulation of the single crystal of Compound A-hydrate as published in U.S. Pat. No. 7,439,251B2 and also from both the XRPD of Form I or Form III (FIG. 13).

TABLE 13

| FORM I (crystallized from ethyl acetate) | | FORM III (the API) | | Computer simulation from X-ray of single crystal published in U.S. Pat. No. 7,439,251B2 | |
|---|---|---|---|---|---|
| 2Th | I/I0 | 2Th | I/I0 | 2Th | I/I0 |
| 8.8 | 5.3 | 8.8 | 3 | 8.8 | 5.7 |
| 9.6 | 1.8 | 9.7 | 1 | 9.6 | 3.2 |

TABLE 13-continued

| FORM I (crystallized from ethyl acetate) | | FORM III (the API) | | Computer simulation from X-ray of single crystal published in U.S. Pat. No. 7,439,251B2 | |
|---|---|---|---|---|---|
| 2Th | I/I0 | 2Th | I/I0 | 2Th | I/I0 |
| 12.3 | 51.9 | 12.3 | 33 | 12.3 | 66.9 |
| 15.6 | 2.2 | 15.6 | 1 | 15.8 | 8.7 |
|  |  | 17.3 | 28 |  |  |
| 17.5 | 100 | 17.5 | 100 | 17.6 | 100 |
|  |  |  |  | 17.9* | 20.4 |
| 19.3 | 0.6 | 19.3 | 1 | 19.3 | 2.6 |
| 19.9 | 9.3 | 19.9 | 10 | 19.5* | 4.1 |
| 21.6 | 16.0 | 21.6 | 19 | 20.1 | 28.4 |
| 22.7 | 1.8 | 22.7 | 1 | 21.9* | 38.2 |
| 23.0 | 2.4 | 23.1 | 2 | 22.9 | 4.9 |
| 23.5 | 5.1 | 23.5 | 5 | 23.3 | 7.3 |
|  |  | 24.4 | 5 | 23.7 | 5.8 |
| 24.5 | 5.8 | 24.6 | 6 | 24.6 | 10.3 |
|  |  |  |  | 24.9* | 6.8 |
| 26.3 | 9.1 | 26.3 | 12 | 26.5 | 22.6 |
| 28.8 | 3.0 | 28.8 | 4 |  |  |
|  |  |  |  | 29.3* | 8.1 |
| 30.3 | 1.1 | 30.4 | 2 | 30.3 | 4.3 |
|  |  |  |  | 30.8* | 4.3 |
| 31.3 | 5.4 | 31.3 | 5 | 31.3 | 8.1 |
| 31.6 | 5.9 | 31.6 | 7 |  |  |
|  |  | 31.8 | 6 | 32.0 | 18.4 |
| 32.5 | 3.0 | 32.5 | 1 | 32.3 | 3.1 |
|  |  | 32.9 | 1 | 33.0 | 3.7 |
| 34.0 | 0.8 | 34 | 1 | 33.4* | 1.7 |
| 34.5 | 3.0 | 34.6 | 3 | 34.5 | 10.3 |

TABLE 14

Crystal data and structure refinement

| | |
|---|---|
| Empirical formula | C10 H20 N2 O2 S |
| Formula weight | 232.34 |
| Temperature | 173(1) K |
| Wavelength | 0.71073 Å |
| Crystal system | Orthorhombic |
| Space group | P2(1)2(1)2(1) |
| Unit cell dimensions | a = 5.8864(9) Å   α = 90°. |
|  | b = 10.3774(15) Å   β = 90°. |
|  | c = 20.165(3) Å   γ = 90°. |
| Volume | 1231.8(3) Å$^3$ |
| Z | 4 |
| Density (calculated) | 1.253 Mg/m$^3$ |
| Absorption coefficient | 0.248 mm$^{-1}$ |
| F(000) | 504 |
| Crystal size | 0.30 × 0.15 × 0.09 mm$^3$ |
| Theta range for data collection | 2.02 to 25.99°. |
| Index ranges | −7 <= h <= 7, −12 <= k <= 12, −24 <= l <= 24 |
| Reflections collected | 12354 |
| Independent reflections | 2425 [R(int) = 0.0421] |
| Completeness to theta = 25.99° | 100.0% |
| Absorption correction | none |
| Max. and min. transmission | 0.9780 and 0.9293 |
| Refinement method | Full-matrix least-squares on F$^2$ |
| Data/restraints/parameters | 2425/0/150 |
| Goodness-of-fit on F$^2$ | 1.247 |
| Final R indices [I > 2sigma(I)] | R1 = 0.0583, wR2 = 0.1259 |
| R indices (all data) | R1 = 0.0599, wR2 = 0.1267 |
| Absolute structure parameter | 0.05(14) |
| Largest diff. peak and hole | 0.563 and −0.317 e.Å$^{-3}$ |

TABLE 15

Atomic coordinates (×10$^4$) and equivalent isotropic displacement parameters (Å$^2$ × 10$^3$). U(eq) is defined as one third of the trace of the orthogonalized U$^{ij}$ tensor.

| | x | y | z | U(eq) |
|---|---|---|---|---|
| C(1) | 9248(6) | 6570(3) | 8882(2) | 18(1) |
| C(2) | 7705(5) | 6459(3) | 8281(2) | 21(1) |
| C(3) | 7798(5) | 4191(3) | 8565(1) | 16(1) |
| C(4) | 5801(6) | 3385(3) | 8805(2) | 22(1) |
| C(5) | 6586(5) | 2238(3) | 9209(2) | 22(1) |
| C(6) | 10115(5) | 2165(3) | 8611(2) | 25(1) |
| C(7) | 9444(6) | 3315(3) | 8191(2) | 23(1) |
| C(8) | 11606(5) | 7045(3) | 8694(2) | 22(1) |
| C(9) | 13089(6) | 7329(4) | 9297(2) | 30(1) |
| C(10) | 8863(7) | 322(3) | 9230(2) | 33(1) |
| N(1) | 7063(5) | 5265(2) | 8156(1) | 20(1) |
| N(2) | 8143(5) | 1425(2) | 8828(1) | 22(1) |
| O(1) | 7172(4) | 7399(2) | 7948(1) | 26(1) |
| O(1W) | 4547(8) | 4847(3) | 7023(2) | 70(1) |
| S(1) | 9210(2) | 4989(1) | 9277(1) | 26(1) |

TABLE 16

Bond lengths [Å] and angles [°]

| | |
|---|---|
| C(1)—C(2) | 1.518(4) |
| C(1)—C(8) | 1.521(4) |
| C(1)—S(1) | 1.825(3) |
| C(1)—H(1) | 1.0000 |
| C(2)—O(1) | 1.226(4) |
| C(2)—N(1) | 1.320(4) |
| C(3)—N(1) | 1.452(4) |
| C(3)—C(4) | 1.522(4) |
| C(3)—C(7) | 1.528(4) |
| C(3)—S(1) | 1.854(3) |
| C(4)—C(5) | 1.515(4) |
| C(4)—H(4A) | 0.9900 |
| C(4)—H(4B) | 0.9900 |
| C(5)—N(2) | 1.463(4) |
| C(5)—H(5A) | 0.9900 |
| C(5)—H(5B) | 0.9900 |
| C(6)—N(2) | 1.459(4) |
| C(6)—C(7) | 1.517(4) |
| C(6)—H(6A) | 0.9900 |
| C(6)—H(6B) | 0.9900 |
| C(7)—H(7A) | 0.9900 |
| C(7)—H(7B) | 0.9900 |
| C(8)—C(9) | 1.526(5) |
| C(8)—H(8A) | 0.9900 |
| C(8)—H(8B) | 0.9900 |
| C(9)—H(9A) | 0.9800 |
| C(9)—H(9B) | 0.9800 |
| C(9)—H(9C) | 0.9800 |
| C(10)—N(2) | 1.464(4) |
| C(10)—H(10A) | 0.9800 |
| C(10)—H(10B) | 0.9800 |
| C(10)—H(10C) | 0.9800 |
| N(1)—H(1N1) | 0.82(4) |
| O(1W)—H(1N1) | 1.95(4) |
| O(1W)—H(1W) | 0.80(5) |
| O(1W)—H(2W) | 0.91(7) |
| C(2)—C(1)—C(8) | 111.8(2) |
| C(2)—C(1)—S(1) | 105.8(2) |
| C(8)—C(1)—S(1) | 114.3(2) |
| C(2)—C(1)—H(1) | 108.2 |
| C(8)—C(1)—H(1) | 108.2 |
| S(1)—C(1)—H(1) | 108.2 |
| O(1)—C(2)—N(1) | 124.7(3) |
| O(1)—C(2)—C(1) | 122.0(3) |
| N(1)—C(2)—C(1) | 113.3(3) |
| N(1)—C(3)—C(4) | 111.8(2) |
| N(1)—C(3)—C(7) | 111.4(2) |
| C(4)—C(3)—C(7) | 108.6(3) |
| N(1)—C(3)—S(1) | 103.4(2) |
| C(4)—C(3)—S(1) | 110.2(2) |
| C(7)—C(3)—S(1) | 111.3(2) |

TABLE 16-continued

| Bond lengths [Å] and angles [°] | |
|---|---|
| C(5)—C(4)—C(3) | 111.5(3) |
| C(5)—C(4)—H(4A) | 109.3 |
| C(3)—C(4)—H(4A) | 109.3 |
| C(5)—C(4)—H(4B) | 109.3 |
| C(3)—C(4)—H(4B) | 109.3 |
| H(4A)—C(4)—H(4B) | 108.0 |
| N(2)—C(5)—C(4) | 111.2(3) |
| N(2)—C(5)—H(5A) | 109.4 |
| C(4)—C(5)—H(5A) | 109.4 |
| N(2)—C(5)—H(5B) | 109.4 |
| C(4)—C(5)—H(5B) | 109.4 |
| H(5A)—C(5)—H(5B) | 108.0 |
| N(2)—C(6)—C(7) | 112.0(3) |
| N(2)—C(6)—H(6A) | 109.2 |
| C(7)—C(6)—H(6A) | 109.2 |
| N(2)—C(6)—H(6B) | 109.2 |
| C(7)—C(6)—H(6B) | 109.2 |
| H(6A)—C(6)—H(6B) | 107.9 |
| C(6)—C(7)—C(3) | 111.0(3) |
| C(6)—C(7)—H(7A) | 109.5 |
| C(3)—C(7)—H(7A) | 109.4 |
| C(6)—C(7)—H(7B) | 109.4 |
| C(3)—C(7)—H(7B) | 109.5 |
| H(7A)—C(7)—H(7B) | 108.0 |
| C(1)—C(8)—C(9) | 112.7(3) |
| C(1)—C(8)—H(8A) | 109.1 |
| C(9)—C(8)—H(8A) | 109.1 |
| C(1)—C(8)—H(8B) | 109.1 |
| C(9)—C(8)—H(8B) | 109.1 |
| H(8A)—C(8)—H(8B) | 107.8 |
| C(8)—C(9)—H(9A) | 109.5 |
| C(8)—C(9)—H(9B) | 109.5 |
| H(9A)—C(9)—H(9B) | 109.5 |
| C(8)—C(9)—H(9C) | 109.5 |
| H(9A)—C(9)—H(9C) | 109.5 |
| H(9B)—C(9)—H(9C) | 109.5 |
| N(2)—C(10)—H(10A) | 109.5 |
| N(2)—C(10)—H(10B) | 109.5 |
| H(10A)—C(10)—H(10B) | 109.5 |
| N(2)—C(10)—H(10C) | 109.5 |
| H(10A)—C(10)—H(10C) | 109.5 |
| H(10B)—C(10)—H(10C) | 109.5 |
| C(2)—N(1)—C(3) | 121.7(3) |
| C(2)—N(1)—H(1N1) | 122(3) |
| C(3)—N(1)—H(1N1) | 116(3) |
| C(6)—N(2)—C(5) | 110.6(2) |
| C(6)—N(2)—C(10) | 110.3(3) |
| C(5)—N(2)—C(10) | 110.0(3) |
| H(1N1)—O(1W)—H(1W) | 117(4) |
| H(1N1)—O(1W)—H(2W) | 104(4) |
| H(1W)—O(1W)—H(2W) | 103(5) |
| C(1)—S(1)—C(3) | 93.89(14) |

Symmetry transformations used to generate equivalent atoms:

TABLE 17

Anisotropic displacement parameters (Å$^2$ × 10$^3$). The anisotropic displacement factor exponent takes the form: $-2\pi^2[h^2a^{*2}U^{11}+\ldots+2hka^*b^*U^{12}]$

|  | U$^{11}$ | U$^{22}$ | U$^{33}$ | U$^{23}$ | U$^{13}$ | U$^{12}$ |
|---|---|---|---|---|---|---|
| C(1) | 24(2) | 13(1) | 17(1) | 0(1) | 2(1) | 1(1) |
| C(2) | 19(2) | 25(2) | 18(2) | 3(1) | 6(1) | 3(1) |
| C(3) | 18(2) | 19(2) | 12(1) | 2(1) | −4(1) | −1(1) |
| C(4) | 19(1) | 25(2) | 22(2) | 0(1) | 2(1) | −1(1) |
| C(5) | 22(2) | 27(2) | 18(2) | 2(1) | 2(1) | −4(1) |
| C(6) | 20(2) | 28(2) | 26(2) | 1(1) | 2(1) | 5(1) |
| C(7) | 27(2) | 24(2) | 18(2) | 1(1) | 4(1) | 0(1) |
| C(8) | 22(2) | 23(2) | 22(2) | 0(1) | 2(1) | −4(1) |
| C(9) | 25(2) | 37(2) | 30(2) | −1(2) | −4(2) | 0(2) |
| C(10) | 46(2) | 21(2) | 32(2) | 5(1) | −13(2) | 0(1) |
| N(1) | 23(1) | 19(2) | 19(1) | 2(1) | −9(1) | 1(1) |
| N(2) | 29(1) | 17(1) | 19(1) | 0(1) | −4(1) | 3(1) |

TABLE 17-continued

Anisotropic displacement parameters (Å$^2$ × 10$^3$). The anisotropic displacement factor exponent takes the form: $-2\pi^2[h^2a^{*2}U^{11}+\ldots+2hka^*b^*U^{12}]$

|  | U$^{11}$ | U$^{22}$ | U$^{33}$ | U$^{23}$ | U$^{13}$ | U$^{12}$ |
|---|---|---|---|---|---|---|
| O(1) | 33(1) | 20(1) | 26(1) | 7(1) | −3(1) | 2(1) |
| O(1W) | 110(3) | 26(2) | 75(2) | 6(2) | −73(2) | −17(2) |
| S(1) | 39(1) | 22(1) | 17(1) | 3(1) | −10(1) | −7(1) |

TABLE 18

Hydrogen coordinates (×10$^4$) and isotropic displacement parameters (Å$^2$ × 10$^3$)

|  | x | y | z | U(eq) |
|---|---|---|---|---|
| H(1) | 8561 | 7207 | 9195 | 22 |
| H(4A) | 4785 | 3928 | 9079 | 26 |
| H(4B) | 4921 | 3077 | 8417 | 26 |
| H(5A) | 7360 | 2546 | 9615 | 27 |
| H(5B) | 5251 | 1723 | 9346 | 27 |
| H(6A) | 11135 | 1599 | 8351 | 29 |
| H(6B) | 10964 | 2469 | 9005 | 29 |
| H(7A) | 8718 | 3011 | 7777 | 27 |
| H(7B) | 10821 | 3809 | 8069 | 27 |
| H(8A) | 11459 | 7838 | 8424 | 27 |
| H(8B) | 12361 | 6384 | 8417 | 27 |
| H(9A) | 12326 | 7962 | 9581 | 46 |
| H(9B) | 14553 | 7676 | 9150 | 46 |
| H(9C) | 13338 | 6532 | 9547 | 46 |
| H(10A) | 9843 | −240 | 8964 | 49 |
| H(10B) | 7523 | −161 | 9376 | 49 |
| H(10C) | 9704 | 630 | 9618 | 49 |
| H(1N1) | 6290(60) | 5080(30) | 7834(18) | 21(9) |
| H(1W) | 4010(90) | 4140(50) | 6960(20) | 51(15) |
| H(2W) | 3300(110) | 5360(60) | 7080(30) | 80(20) |

TABLE 19

| Torsion angles [°] | |
|---|---|
| C(8)—C(1)—C(2)—O(1) | −63.0(4) |
| S(1)—C(1)—C(2)—O(1) | 172.0(2) |
| C(8)—C(1)—C(2)—N(1) | 115.7(3) |
| S(1)—C(1)—C(2)—N(1) | −9.3(3) |
| N(1)—C(3)—C(4)—C(5) | 177.8(2) |
| C(7)—C(3)—C(4)—C(5) | 54.4(3) |
| S(1)—C(3)—C(4)—C(5) | −67.8(3) |
| C(3)—C(4)—C(5)—N(2) | −57.5(3) |
| N(2)—C(6)—C(7)—C(3) | 56.9(4) |
| N(1)—C(3)—C(7)—C(6) | −177.4(3) |
| C(4)—C(3)—C(7)—C(6) | −53.7(3) |
| S(1)—C(3)—C(7)—C(6) | 67.8(3) |
| C(2)—C(1)—C(8)—C(9) | 172.6(3) |
| S(1)—C(1)—C(8)—C(9) | −67.2(3) |
| O(1)—C(2)—N(1)—C(3) | 178.7(3) |
| C(1)—C(2)—N(1)—C(3) | 0.1(4) |
| C(4)—C(3)—N(1)—C(2) | 127.5(3) |
| C(7)—C(3)—N(1)—C(2) | −110.7(3) |
| S(1)—C(3)—N(1)—C(2) | 8.9(3) |
| C(7)—C(6)—N(2)—C(5) | −58.3(3) |
| C(7)—C(6)—N(2)—C(10) | 179.8(3) |
| C(4)—C(5)—N(2)—C(6) | 58.2(3) |
| C(4)—C(5)—N(2)—C(10) | −179.7(3) |
| C(2)—C(1)—S(1)—C(3) | 12.1(2) |
| C(8)—C(1)—S(1)—C(3) | −111.4(2) |
| N(1)—C(3)—S(1)—C(1) | −11.7(2) |
| C(4)—C(3)—S(1)—C(1) | −131.4(2) |
| C(7)—C(3)—S(1)—C(1) | 108.0(2) |

Symmetry transformations used to generate equivalent atoms:

TABLE 20

| Hydrogen bonds [Å and °]. | | | | |
|---|---|---|---|---|
| D-H...A | d(D-H) | d(H...A) | d(D...A) | <(DHA) |
| O(1W)—H(2W)...N(2)#1 | 0.91(7) | 2.30(7) | 2.852(4) | 119(5) |
| O(1W)—H(1W)...O(1)#2 | 0.80(5) | 1.95(5) | 2.735(4) | 166(5) |
| N(1)—H(1N1)...O(1W) | 0.82(4) | 1.95(4) | 2.757(4) | 173(4) |

Symmetry transformations used to generate equivalent atoms:
1 −x+1,y+½,−z+3/2  #2 −x+1,y−½,−z+3/2

Example 28: Formulation of Form II and Form III, Respectively, in Vials for Reconstitution as Oral Solution Compound A Form II and Form III powder, respectively, is filled in 8 ml amber glass (Type I) vials (120 mg/vial) and the vials are closed with a teflon/rubber screw cap. Upon addition of approx. 5 ml of distilled water and complete dissolution of the crystal powder, an oral solution results that can be used, inter alia, to treat diseases as described above.

Example 29: Formulation of Form III in Oral Capsules

Compound A Form III powder is mixed with one or more excipient(s) (pregelatinized starch, microcrystalline cellulose, colloidal silicon dioxide, and stearic acid) and the mixture is filled in size 4, white opaque, hard gelatin, two-piece capsules to provide 5 mg or 10 mg Compound A Form III per capsule. The capsules can be used as an oral formulation for immediate release in the gastrointestinal tract.

Example 30: Formulation of Form II in Oral Tablets

Compound A Form II powder is mixed with one or more anhydrous excipient(s) (e.g., anhydrous dibasic calcium phosphate) and compressed directly into tablets that contain 5 mg, 10 mg, or 20 mg of the active agent per tablet.

Example 31: Long-Term Conditions and Accelerated Conditions Stability in Bulk for the API, Compound A Monohydrate (Form III)

Highly Stabile API: Compound A (NGX267) clinical batch (cGMP) met specification under long-term conditions at the 0, 3, 6, 9, 12, 18 and 24 month time point when stored at 25° C./60% RH without change in appearance (white powder); in DSC (T=0, 64.2 and 133.8° C.; and T=12 months, 64.5 and 133.8° C.); in purity by HPLC (achiral) =100% and HPLC (chiral) (99.9-100%); in water content (7.2-8%).

Highly Stabile API in formulation: Compound A (NGX267) 5 mg strength capsule drug product and Compound A (NGX267) 10 mg strength capsule drug product met specification for up to 18 months when stored at 25° C./60% RH and for up to 6 months when stored at 40° C./75% RH.

Example 32: Pharmacokinetics of Form II in Man

In the first Phase I clinical study, the API administered orally was prepared according to Example 29 but with additional higher and lower dosing. A total of 34 subjects were randomized to receive a single dose either of the of study drug (1, 2.5, 5, 10, 15, 25, 35, or 45 mg of Compound A Form II which had been designated NGX267; n=3 for each dose) or matched placebo (n=10). The maximum tolerated dose (35 mg) was reached by 10 individuals, with 8 subjects (80%) reporting a total of 31 adverse events and 2 subjects (20%) reporting no adverse events. Treatment-emergent adverse events reported by more than one subject treated with this dose were salivary hypersecretion (four subjects, 40%), hyperhidrosis (four subjects, 40%), cold sweat (four subjects, 40%), abdominal discomfort (two subjects, 20%), and dysgeusia (two subjects, 20%). In a separate Phase I study that randomized healthy elderly subjects (age 65-80 years) of both sexes (20 received NGX267 and 6 received placebo), the maximum tolerated oral dose was determined to be 20 mg.

In a double-blind, placebo-controlled, multiple-dose, sequential cohort study that randomized 60 healthy male volunteers (age 18-54 years), 48 received Compound A Form II (NGX267; 10, 20, 30, 35 mg once daily for 4 days) and 12 received placebo. Plasma concentrations of NGX267 and its active desmethyl metabolite (NGX292) increased dose-proportionally. Steady-state conditions were attained on the third day of dosing. The apparent elimination half-life of NGX267 was similar across dose levels, with mean estimates of t½ ranging from 7.06 to 7.57 h on Day 0 and 6.58 to 7.14 h on Day 3. Mean estimates of CL/F ranged from 299.9 to 342.9 ml/min on Day 0 and 335.4 to 373.5 ml/min on Day 3. The mean fraction of the administered dose of NGX267 recovered in urine (as NGX267 or NGX292) over 24 h post-dose ranged from 0.4001 to 0.4605 across all dose levels.

Example 33: Safety and Preliminary Efficacy of Form III in Sjögren Syndrome

A Phase II clinical trial was conducted to evaluate the tolerability, safety and efficacy of Compound A Form III (NGX267) at single doses of 10 mg, 15 mg and 20 mg (as capsules according to Example 30) compared with placebo when given to patients with xerostomia associated with primary or secondary Sjögren's syndrome. A total of 26 patients were recruited, and randomized to four treatment groups in four treatment periods at three study centers. All completed the study and were used in the analysis. On each study day, whole mouth salivary flow rates were measured as a primary parameter. As a secondary study parameter, subjective measurements of salivary gland dysfunction were assessed 2, 4, 6, 12, 14, and 24 hours post-dose using an 8-item visual analog scale. As an additional exploratory parameter, a standard Schirmer test was conducted bilaterally at baseline and 2, 12, 14, and 24 hours post-dose to assess tear production.

All three NGX267 doses were safe, well tolerated, and effective with respect to xerostomia. Between 6 and 24 hours post-dose, saliva production and maximum saliva flow were significantly greater than that observed with placebo treatment after administration of all three doses of NGX267, with a linear relationship between dose and saliva production in the first 6 hours and in the first 24 hours. In subjective measures, there was a significant improvement compared with placebo for all 8 items assessed by the visual analog scale for the 15 mg and 20 mg doses. Although the 15 mg dose increased tear production significantly over placebo, there was no overall treatment effect in this exploratory parameter.

Throughout the present description and claims, terms which are defined as they are introduced retain those definitions throughout the description and claims.

The inventions illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

Other embodiments are set forth within the following claims.

The invention claimed is:

1. A crystalline polymorph of Compound A of the formula

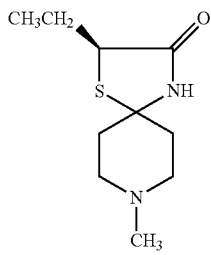

wherein said polymorph is selected from the group consisting of monohydrate Form III
(i) having an X-ray powder diffraction pattern containing at least one of the following 2-theta values (±0.2) as measured using CuK$_\alpha$ radiation: 12.3, 17.3, 17.5, 19.9, 21.6, 24.6, 26.3, and 35.4, and substantially free of peaks having 2-theta values in the range of 10.8-11.9;
(ii) wherein the $^{13}$C solid-state NMR of the crystalline form contains at least one resonance having one of the following chemical shift values as expressed in ppm relative to TMS: 67.56, 54.60, 47.07, 41.49, 30.70 and 13.77;
(iii) wherein the $^{13}$C solid-state NMR of the crystalline form contains a difference in chemical shift between the resonance having the largest chemical shift and another resonance of 107.3, 120.3, 127.9, 133.4, 144.2 or 161.1;
(iv) wherein the ZnSe ATR-FT-IR absorption spectrum of the crystalline form contains at least one absorption peak having a value selected from 1039, 1353, 1369, 1388, 2918, 2974 and 3088 cm$^{-1}$; and/or
(v) wherein the crystalline form exhibits a very broad endothermic peak at 58-94° C. and an endothermic peak with an onset at 133.7° C. and a peak at 134.9° C. as measured by differential scanning calorimetry (DSC), anhydrous Form II
(i) that exhibits a single crystal X-ray characterized by the following single crystal X-ray data: P2(1) a=8.1416(13), (α=90°), b=7.9811(12) (β= 90.761(2)°, c=17.878(3), (γ=90°), Å, T=173(1)K;
(ii) having an X-ray powder diffraction pattern containing at least one of the following 2-theta values (±0.2) as measured using CuK$_\alpha$ radiation: 9.9, 10.8, 11.8, 11.9, 14.8, 16.2, 18.2, 18.5, 19.8, 21.3, 22.4, 23.9, 29.2, 29.7 and 33.1;
(iii) wherein the ZnSe ATR-FT-IR absorption spectrum of the crystalline form contains at least one absorption peak having a value selected from 1906, 1340, 1447, 2869, 2901, 2951, and 3006-3012 cm$^{-1}$;
(iv) wherein the $^{13}$C solid-state NMR of the crystalline form contains at least one resonance having one of the following chemical shift values as expressed in ppm relative to TMS: 175.0; 65.3, 64.0; 45.8, 45.0; 49.3, 43.6; 39.5, 38.8; 28.9, 26.0; 15.4, 14.8;
(v) wherein the $^{13}$C solid-state NMR of the crystalline form contains a difference in chemical shift between the resonance having the largest chemical shift and another resonance of 109.7 or 111; 129.2 or 130.0; 122.7; 125.7; 131.4; 135.5; 136.2; 146.1 or 149.0; and 159.6 or 160.2; and/or
(vi) wherein the crystalline form has an endothermic peak with an onset at 134.2° C. and peak at 135.4° C.±0.2° C. and substantially no endothermic peak between 106° C. and 110° C., lacking an endotherm peak in the range of about 50° C. to about 120° C., as measured by DSC, monohydrate Form I
(i) having an X-ray powder diffraction pattern containing at least one of the following 2-theta values (±0.2) as measured using CuK$_\alpha$ radiation: 8.8, 12.3, 17.5, 19.9, 21.6 23.5, 24.5, 26.3, 28.8, 31.6, but lacks at least one of the following 2-theta values 17.3, 17.9, 21.9, 24.9, 29.3, 30.8 and 33.4 and is substantially free of peaks having 2-theta values in the range of 10.8-11.9;
(ii) wherein the ZnSe ATR-FT-IR absorption spectrum of the crystalline form contains at least one absorption peak having a value selected from 1352, 1369 and 1387 cm$^{-1}$; and/or
(iii) wherein the crystalline form exhibits an endothermic peak at 107.1° C. (onset at 104.85° C.) and 136.17° C. (onset at 133.41° C.) as measured by differential scanning calorimetry (DSC); and optionally
(iv) wherein the $^{13}$C solid-state NMR of the crystalline form contains at least one resonance having one of the following chemical shift values as expressed in ppm relative to TMS: 67.09, 54.08, 46.59, 40.97, 30.15 and 13.27; and/or
(v) wherein the $^{13}$C solid-state NMR of the crystalline form contains a difference in chemical shift between the resonance having the largest chemical shift and another resonance of 107.3, 120.3, 127.8, 133.4, 144.2 or 161.1.

2. The crystalline polymorph of claim 1, wherein the polymorph is the polymorph Form II.

3. The crystalline polymorph of claim 2, wherein
(a) the crystalline form is further characterized by the following data: Volume=1161.6 (3) Å 3, Z=4, F(000)= 464, Calculated density, Dc=1.226 Mg/m$^3$, Absorption coefficient, μ=0.251 mm$^{-1}$;

(b) the X-ray powder diffraction pattern contains at least two, three, four, five, six, seven, eight, nine, ten, eleven or all of the following 2-theta values as measured using CuK$_\alpha$ radiation: 9.9, 10.8, 11.8, 11.9, 14.8, 16.2, 18.2, 18.5, 19.8, 21.3, 22.4, 23.9, 29.2 and 29.7, 33.0, 33.1;

(c) the X-ray powder diffraction pattern comprises at least one additional peak at a diffraction angle 2θ selected from the group consisting of 14.8° and 19.8° and/or selected from the group consisting of 18.2° and 18.5°;

(d) the ZnSe ATR-FT-IR absorption spectrum of the crystalline form contains at least two, three, four, five, six or all absorption peaks having a value selected from 906, 1340, 1447, 2869, 2901, 2951, and 3006-3012 cm$^{-1}$;

(e) the $^{13}$C solid-state NMR of the crystalline form contains resonances having at least two, three, four, five, six, seven or all of the following chemical shift values as expressed in ppm relative to TMS: 175.0; 65.3, 64.0; 45.8, 45.0; 49.3, 43.6, 39.5; 38.8; 28.9, 26.0; 15.4, 14.8;

(f) the X-ray powder diffraction pattern contains the following 2-theta values: 9.9, 10.8, 18.5, 19.8±0.2; and wherein the $^{13}$C solid-state NMR of the crystalline form contains resonance having the following chemical shift values as expressed in ppm relative to TMS: 14.8, 15.4, 26.0, 28.9, 64.0, 65.3; and wherein the ZnSe ATR-FT-IR absorption spectrum of the crystalline form contains absorption peak having a value selected in the range of from 1340-1362 cm-1±5 cm$^{-1}$; and/or (g) the polymorph form exhibits less than 1% weight loss as determined by thermogravimetric analysis (TGA) up to a temperature of about 110° C. at a heating rate of about 3° C. per minute.

4. The crystalline polymorph of claim 1, wherein the polymorph is the polymorph Form III.

5. The crystalline polymorph of claim 4, wherein
(a) the X-ray powder diffraction pattern contains at least two, three or all of the following 2-theta values as measured using CuK$_\alpha$ radiation: 8.8, 12.30, 17.30, 17.50, 17.80 and 23.0;

(b) the X-ray powder diffraction pattern also contains at least one of the following 2-theta values as measured using CuK$_\alpha$ radiation: 12.3 19.9, 21.6, 24.5, 26.3 and 31.6;

(c) the X-ray powder diffraction pattern is substantially free of peaks having 2-theta values in the range of from 10.8-11.8;

(d) the X-ray powder diffraction pattern contains at least one of the following 2-theta values as measured using CuK$_\alpha$ radiation: 12.2, 17.3, 19.9, 21.6, 24.5, 26.3 and 31.6, and wherein said X-ray powder diffraction is substantially free of peaks having 2-theta values in the range of from 10.8-11.8;

(e) the X-ray powder diffraction pattern contains at least two, three, four, five or all of the following 2-theta values as measured using CuK$_\alpha$ radiation 12.2, 17.3, 17.5, 19.9, 21.6, 24.5, 26.3 and 31.2;

(f) the $^{13}$C solid-state NMR of the crystalline form contains resonances having at least two, three, four or all of the following chemical shift values as expressed in ppm relative to TMS: 67.56, 54.60, 41.49, 30.70 and 13.77;

(g) the $^{13}$C solid-state NMR of the crystalline form contains at least two, three, four or all differences in chemical shift between the resonance having the largest chemical shift and other resonances selected from 107.3, 120.3, 133.4, 144.2 and 161.1; and/or (h) the ZnSe ATR-FT-IR absorption spectrum of the crystalline form contains at least two, three, four, five, six or all absorption peaks having a value selected from 1039, 1353, 1369, 1388, 2918, 2974 and 3088 cm$^{-1}$.

6. A crystalline monohydrate form of the compound (S)-2-ethyl-8-methyl-1-thia-4,8-diazaspiro[4.5]decan-3-one having an X-ray powder diffraction pattern containing the following 2-theta values: 12.3, 17.3, 17.5, 19.9, 21.6±0.2; and wherein the $^{13}$C solid-state NMR of the crystalline form contains resonance having the following chemical shift values as expressed in ppm relative to TMS: 13.6, 30.6, 67.5; and wherein the ZnSe ATR-FT-IR absorption spectrum of the crystalline form contains an absorption peak having a value selected from 1353, 1369 and 1388±5 cm$^{-1}$; and wherein the crystalline form shows a very broad endotherm at 58-94° C. and an endotherm having an onset at 133.9° C.

7. A process for preparing the crystalline polymorph Form of Compound A of claim 1:

comprising the steps of:
(a) dissolving Compound A in appropriate solvent;
(b) if necessary, cooling the resulting solution;
(c) waiting sufficient time for the crystalline form to crystallize, until Form II crystals precipitate; and
(d) filtering said crystalline form; wherein
(i) the crystalline form is polymorph Form II and the solvent is selected from the group consisting of acetone, acetonitrile, cyclohexane, hexane, dioxane and mixed solvents of ethanol and acetonitrile;
(ii) the crystalline form is polymorph Form III and obtained by adding 1.3 moles of de-ionized water to the solution of Compound A in acetone, or by a re-slurry of Compound A and/or polymorph Form II in de-ionized water and filtration;
(iii) the crystalline form is polymorph Form I and obtained by crystallization from water-miscible organic solvents that contain traces of water, water or slow evaporation of a solution of the compound dissolved either in water or ethyl acetate; or
(iv) the crystalline form is a mixture of the crystalline polymorph Forms I and II and the solvent is selected from the group consisting of toluene, dichloromethane, 1-butanol, or diethyl ether.

8. A process for converting polymorph Form II of claim 2 into polymorph Form III, comprising maintaining the crystalline polymorph Form II at room temperature and at least 95% relative humidity for a time sufficient for conversion to a crystalline polymorph Form III.

9. A process for converting polymorph Form I of claim 1 into polymorph Form II comprising one of the following:
(a) maintaining a crystalline Form I at an elevated temperature below the melting point of the crystalline form for a sufficient time to convert the crystalline Form I into said crystalline polymorph Form II;

(b) suspending a crystalline polymorph Form I in a solvent selected from the group consisting of acetonitrile, cyclohexane, hexane, dioxane and mixed solvents of ethanol and acetonitrile, waiting sufficient time for the crystalline form of Form II to crystallize, and filtering said crystalline form; and (c) heating the crystalline polymorph Form I above its melting point to form a molten mass and cooling the molten mass.

10. The process of claim 7, wherein the resultant crystalline polymorph Form I, II or III is selected by identifying the polymorph according its X-ray powder diffraction pattern of 2-theta values as measured using $CuK_\alpha$ radiation, ZnSe ATR-FT-IR absorption spectrum endothermic peaks as measured by DSC, TGA and/or resonance as measured by $^{13}C$ solid-state NMR.

11. A process for stably maintaining a crystalline polymorph Form II of claim 2 comprising maintaining said crystalline at room temperature in a dry atmosphere.

12. A pharmaceutical composition comprising a crystalline polymorph of claim 1 and at least one pharmaceutically acceptable excipient or carrier.

13. A process for preparing a medicament based on a formulation of crystalline polymorph of Compound A of claim 1, wherein
(a) the crystalline polymorph is polymorph Form II, which is suitable for oral administration, and wherein the formulation is directly compressed into tablets; or
(b) the crystalline polymorph is polymorph Form III, which is suitable for oral administration, wherein it is mixed with one or more excipient(s) selected from the group consisting of pregelatinized starch, microcrystalline cellulose, colloidal silicon dioxide, and stearic acid, and the mixture is filled in size 4, white opaque, hard gelatin, two-piece capsules to provide 5 mg or 10 mg polymorph Form III per capsule, which can be used as an oral formulation for immediate release in the gastrointestinal tract.

14. A method of treating or ameliorating a disease or medical condition with a muscarinic receptor agonist in a subject, the method comprising administering a crystalline polymorph Form of claim 1 to the subject, wherein the disease or medical condition is selected from the group consisting of senile dementia of Alzheimer's type; Alzheimer's disease (AD); mild cognitive impairment (MCI) conducive to AD; schizophrenia; and cognitive disorders due to drug abuse or drug withdrawal.

15. The pharmaceutical composition of claim 12, further comprising at least one additional pharmacologically active compound.

16. The process of claim 8, wherein the resultant crystalline polymorph Form III is selected by identifying the polymorph according its X-ray powder diffraction pattern of 2-theta values as measured using $CuK_\alpha$ radiation, ZnSe ATR-FT-IR absorption spectrum endothermic peaks as measured by DSC, TGA and/or resonance as measured by $^{13}C$ solid-state NMR.

17. The process of claim 9, wherein the resultant crystalline polymorph Form II is selected by identifying the polymorph according its X-ray powder diffraction pattern of 2-theta values as measured using $CuK_\alpha$ radiation, ZnSe ATR-FT-IR absorption spectrum endothermic peaks as measured by DSC, TGA and/or resonance as measured by $^{13}C$ solid-state NMR.

18. The method of claim 14, wherein the daily dose is about 10 mg to about 50 mg.

19. The method of claim 14, wherein the disease or condition is associated with (i) impaired cholinergic function, (ii) an imbalance in cholinergic function, (iii) impaired activity of acetylcholine receptors, or (iv) impaired activity of M1 receptors.

20. The pharmaceutical composition according to claim 12, wherein the polymorph Form II or III is present in an amount of between 10 mg and 0.50 mg in the formulation.

21. The pharmaceutical composition according to claim 12, wherein the formulation is granulated.

22. The pharmaceutical composition of claim 12, wherein the polymorph Form II or III is present in an amount of between 1 mg and 100 mg in the formulation.

23. The pharmaceutical composition of claim 15, wherein the at least one additional pharmacologically active compound is selected from the group consisting of: cholinesterase inhibitors, nicotinic agonists, cholinergic precursors and cholinergic enhancers, nootropics, peripheral antimuscarinic drugs, M2 muscarinic antagonists, M4 antagonists, benzodiazepine inverse agonists, sigma-1 agonists, antidepressants, tricyclic antidepressants or antimuscarinic drugs used in treatment of Parkinson's disease (PD) or depression, antipsychotic and antischizophrenic agents, glutamate antagonists and modulators, metabotropic glutamate receptor agonists, NMDA antagonists, AMPA agonists, acetyl-L-carnitine, MAO-B inhibitors, peptides and growth factors, cholesterol-lowering agents, antioxidants, GSK-3 beta inhibitors, Wnt- ligands, PKC-activators, beta- or gamma-secretase inhibitors, beta-amyloid degrading agents, activators of enzymes involved in degradation of beta-amyloid such as activators of neprilysin, insulin degrading enzyme or endothelin converting enzyme, beta-amyloid anti-aggregation agents, chelating agents, antibodies and immunotherapeutic compounds against beta-amyloids, tau protein pathology and/or alpha-synuclein pathology, compounds that bind to amyloids, cyclooxygenase (COX)-2 inhibitors, non-steroidal antiinflammatory drugs, estrogenic agents, estrogenic receptor modulators, steroidal neuroprotectants, and spin trapping pharmaceuticals.

24. The process of claim 7, wherein the solvent of part (d)(iii) is selected from the group consisting of ethanol, ethyl acetate, isopropanol, tert-butylmethylether, and tetrahydrofuran.

* * * * *